US006239270B1

(12) United States Patent
Akerström et al.

(10) Patent No.: US 6,239,270 B1
(45) Date of Patent: *May 29, 2001

(54) NUCLEIC ACIDS ENCODING HUMAN CALCIUM SENSOR PROTEIN

(75) Inventors: Göran Akerström; Claes Juhlin; Lars Rask; Göran Hjälm, all of Uppsala (SE); Clarence C. Morse, Royersford, PA (US); Edward M. Murray, Drexel Hill, PA (US); Gregg R. Crumley, Philadelphia, PA (US)

(73) Assignee: Rhone-Poulenc Rorer S.A., Antony (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/476,515

(22) Filed: Jun. 7, 1995

Related U.S. Application Data

(63) Continuation-in-part of application No. 08/344,836, filed on Nov. 23, 1994, now abandoned, which is a continuation-in-part of application No. PCT/SE94/00483, filed on May 24, 1994.

(30) Foreign Application Priority Data

May 24, 1993 (SE) ................................................ 9301764

(51) Int. Cl.⁷ ................... A61K 31/7105; A61K 31/711; C07H 21/04
(52) U.S. Cl. ........................... 536/24.3; 514/44; 536/24.1
(58) Field of Search .............................. 514/44; 536/24.1, 536/24.3

(56) References Cited

PUBLICATIONS

Godson et al., *JBC*, vol. 268, pp. 11946–11950, Jun. 5, 1993.
C. Juhlin et al., "500–Kilodalton calcium sensor regulating cytoplasmic Ca2+ in cytotrophoblast cells of human placenta," *J. Biol. Chem.*, 265(14) pp. 8275–8279, 1990.
A. Saito et al., "Complete cloning and sequencing if rat gp330/"megalin," a distinctive member of the low density lipoprotein receptor gene family," *Proc. Nat'l. Acad. Sci. U.S.A.*, 91(21) pp. 9725–9729, 1994.
R. Raychowdhury et al., "Autoimmune target in Heymann nephritis is a glycoprotein with homology to the LDL receptor," *Science*, 244(4909), pp. 1163–1165, 1989.

C. Juhlin et al., "Monoclonal antibodies with exclusive reactivity against paratheyroid cells and tubule cells of the kidney," *Proc. Nat'l. Acad. Sci. U.S.A.*, 84(9), pp. 2990–2994, 1987.
S. Lundgren et al., "A protein involved in calcium sensing of the human parathyroid and placental cytotrophoblast cells belongs to the LDL–receptor protein superfamily," *Exp. Cell Res.*, 212(2), PP. 344–350, 1994.
E.M. Brown et al., "Molecular mechanisms underlying the sensing of extracellular Ca2+ by parathyroid and kidney cells," *Eur. J. Endocrinol.* 132 (5), pp. 523–31, 1995.
S.K. Moestrup, "The alpha 2–macroglobulin recepto and epithelial glycopotein–330; two giant receptors mediating endocytosis of multiple ligands," *Biochim. Biophys. Acta.*, 1197(2), pp. 197–213, 1994.
M.G. Farquhar et al., "gp330 and RAP: the Heymann nephritis antigenic complex," *Ann. N. Y. Acad. Sci.*, 737, pp. 96–113, 1994.
M.S. Kounnas et al., "An overview of the structure and function of glycoprotein 330, a receptor related to the alph 2–macroglobulin receptor," *Ann. N.Y. Acad. Sci.*, 737 pp. 114–123, 1994.
S.K. Moestrup et al., "Binding and endocytosis of proteins mediated by epithelial gp330," *Ann N Y Acad. Sci.*, 737, pp. 124–137, 1994.

*Primary Examiner*—Gary L. Kunz
*Assistant Examiner*—Stephen Gucker
(74) *Attorney, Agent, or Firm*—Finnegan, Henderson, Farabow, Garrett & Dunner L.L.P.

(57) ABSTRACT

The present invention relates to the isolation of a cDNA clone encoding the calcium sensor in human placenta and subsequent Northern blots confirming the mRNA expression also in human parathyroid and kidney tubule cells. Close sequence similarity is demonstrated with the rat Heymann nephritis antigen, a glycoprotein of the kidney tubule brush border with calcium binding ability. Immunohistochemistry substantiates a tissue distribution of the calcium sensor protein similar to that previously described for the Heymann antigen. It is proposed that the identified calcium sensor protein constitutes a universal sensor for recognition of variation in extracellular calcium, and that it plays a key role for calcium regulation via different organ systems. The calcium sensor protein belongs to the LDL-superfamily of glycoproteins, claimed to function primarily as protein receptors, but with functionally important calcium binding capacity.

4 Claims, 68 Drawing Sheets

```
AAA TAC GTA ATG CAG CCA GAT GGA ATA GCA GTG GAC TGG GTT GGA AGG CAT ATT
 K   Y   V   M   Q   P   D   G   I   A   V   D   W   V   G   R   H   I    56

27

TAC TGG TCA GAT GTC AAG AAT AAA CGC ATT GAG GTG GCT AAA CTT GAT GGA AGG
 Y   W   S   D   V   K   N   K   R   I   E   V   A   K   L   D   G   R   108

81

TAC AGA AAG TGG CTG ATT TCC ACT GAC CTG GAC CAA CCA GCT GCT ATT GCT GTG
 Y   R   K   W   L   I   S   T   D   L   D   Q   P   A   A   I   A   V   162

135

AAT CCC AAA CTA GGG CTT ATG TTC TGG ACT GAC TGG GGA AAG GAA CCT AAA ATC
 N   P   K   L   G   L   M   F   W   T   D   W   G   K   E   P   K   I   216

189

GAG TCT GCC TGG ATG AAT GGA GAG GAC CGC AAC ATC CTG GTT TTC GAG GAC CTT
 E   S   A   W   M   N   G   E   D   R   N   I   L   V   F   E   D   L   270

243

GGT TGG CAA ACT GGC CTT TCT ATC GAT TAT TTG AAC AAT GAC CGA ATC TAC TGG
 G   W   Q   T   G   L   S   I   D   Y   L   N   N   D   R   I   Y   W   324

```
AGT GAC TTC AAG GAG GAC GTT ATT GAA ACC ATA AAA TAT GAT GGG ACT GAT AGG 378
 S   D   F   K   E   D   V   I   E   T   I   K   Y   D   G   T   D   R

351
AGA GTC ATT GCA AAG GAA GCA ATG AAC CCT TAC AGC CTG GAC ATC TTT GAA GAC 432
 R   V   I   A   K   E   A   M   N   P   Y   S   L   D   I   F   E   D

405
CAG TTA TAC TGG ATA TCT AAG GAA GGA GAA GTA TGG AAA CAA AAT AAA TTT    486
 Q   L   Y   W   I   S   K   E   G   E   V   W   K   Q   N   K   F

459
GGG CAA GGA AAG AAA GAG AAA ACG CTG GTA GTG AAC CCT TGG CTC ACT CAA GTT 540
 G   Q   G   K   K   E   K   T   L   V   V   N   P   W   L   T   Q   V

513
CGA ATC TTT CAT CAA CTC AGA TAC AAT AAG TCA GTG CCC AAC CTT TGC AAA CAG 594
 R   I   F   H   Q   L   R   Y   N   K   S   V   P   N   L   C   K   Q

567
ATC TGC AGC CAC CTC TGC CTT CTG AGA CCT GGA GGA TAC AGC TGT GCC TGT CCC 648
 I   C   S   H   L   C   L   L   R   P   G   G   Y   S   C   A   C   P

```
                                              702
CAA GGC TCC AGC TTT ATA GAG GGG AGC ACC ACT GAG TGT GAT GCA GCC ATC GAA
 Q   G   S   S   F   I   E   G   S   T   T   E   C   D   A   A   I   E
                        675                            729
                                                                       756
CTG CCT ATC AAC CTG CCC CCA TGC AGG TGC ATG CAC GGA GGA AAT TGC TAT
 L   P   I   N   L   P   P   C   R   C   M   H   G   G   N   C   Y
                        783
TTT GAT GAG ACT GAC CTC CCC AAA TGC AAG TGT CCT AGC GGC TAC ACC
 F   D   E   T   D   L   P   K   C   K   C   P   S   G   Y   T
```

*FIG. 3 cont.*

```
CA-SEN    KYVMQPDGIAVDWVGRHIYWSDVKNKRIEVAKLDGRYRKWLISTDLDQPAAIAVNPKLGL
HEYMANN   XXXXX***L**********************ANSQ*****T***********T*Q**********L
LDL-RRP   TGLSN***L*******GNL**C*KGRDT***S**N*A**TV*V*SG*RE*R*LV*DVQN*Y
LDL-RC    RDIQA***L****IHSN***T*SVLGTVS**DTK*VK**T*FRENGSK*R**V*D*VH*F

CA-SEN    MFWTDWGKEPKIESAWMNGEDRNILVFEDLGWPTGLSIDYLNNDRIYWSDFKEDVIETIK
HEYMANN   ***QQ*************H*SV**S*N**W*N*******DV*S**A
LDL-RRP   LY*****DHSL*GRIG*D*SS*SVI*DTKITW*NTLVTE-****A*ARYFAS
LDL-RC    *Y***TPAKKGGL**V*IYS**T*NIQW*N*ITL*L*SG-*L**V*S*LHS*SS*D

FIG. 6

```
                    *         10*            20*            30*            40*
CAA  GGC  TGT  GAG  AGG  ACA  TGC  CAT  CCT  GTG  GGG  GAT  TTC  CGC  TGT
GTT  CCG  ACA  CTC  TCC  TGT  ACG  GTA  GGA  CAC  CCC  CTA  AAG  GCG  ACA
 Q    G    C    E    R    T    C    H    P    V    G    D    F    R    C

50*            60*            70*            80*            90*
AAA  ACT  CAC  TGC  ATC  CCT  CTT  CGT  GGA  TGG  GGG  CCT  GTG  TTC  AAG
TTT  TGA  GTG  ACG  TAG  GGA  GAA  GCA  CCT  ACC  CCC  GGA  CAC  AAG  TTC
 K    T    H    C    I    P    L    R    G    W    G    P    V    F    K

100*           110*           120*           130*           140*
GAC  TGT  GGA  GAT  AAC  TCA  GAT  GAG  CTT  CGT  GCT  AAT  CAG  TGT  CAG  GGG
CTG  ACA  CCT  CTA  TTG  AGT  CTA  CTC  GAA  GCA  CGA  TTA  GTC  ACA  GTC  CCC
 D    C    G    D    N    S    D    E    L    R    A    N    Q    C    Q    G

150*           160*           170*           180*           190*
ACA  GAG  AGC  GAG  TTT  AAA  TAC  CAT  GTC  AAT  CGA  GCT  TCG  GAG  TGC  CCC
TGT  CTC  TCG  CTC  AAA  TTT  ATG  GTA  CAG  TTA  GCT  CGA  AGC  CTC  ACG  GGG
 T    E    S    E    F    K    Y    H    V    N    R    A    S    E    C    P

200*           210*           220*           230*           240*
TGG  ATC  TGT  GAC  CAT  TAC  AAC  TGT  GGG  GAC  AAC  TCA  ATT  CGG  GAA  CGA
ACC  TAG  ACA  CTG  GTA  ATG  TTG  ACA  CCC  CTG  TTG  AGT  TAA  GCC  CTT  GCT
 W    I    C    D    H    Y    N    C    G    D    N    S    I    R    E    R

CGG  GCT  GCC
GCC  CGA  CGG
 R    A    R
```

```
          250       260       270       280
       *    *    *    *    *    *    *    *
    GAC TGT GAG ATG AGG ACC TGC CAT CCT GAA TAT TTT CAG TGT ACA AGT
    CTG ACA CTC TAC TCC TGG ACG GTA GGA CTT ATA AAA GTC ACA TGT TCA
     D   C   E   M   R   T   C   H   P   E   Y   F   Q   C   T   S 290       300       310       320       330
       *    *    *    *    *    *    *    *    *    *
    GGA CAT TGT GTA CAC AGT GAA CTG AAA TGC ACG TCC GAT GGA GCT GAC TGT
    CCT GTA ACA CAT GTG TCA CTT GAC TTT ACG TGC AGG CTA CCT CGA CTG ACA
     G   H   C   V   H   S   E   L   K   C   T   S   D   G   A   D   C 340       350       360       370       380
       *    *    *    *    *    *    *    *    *    *
    TTG GAT GCG TCT GAT GAA CTT GCT CCA GAT TGT ACA CCC GAA TGC CGC TTT CCT GAT GGT
    AAC CTA CGC AGA CTA CTT GAA CGA GGT CTA ACA TGT GGG CTT ACG GCG AAA GGA CTA CCA
     L   D   A   S   D   E   L   A   P   D   C   T   P   E   C   R   F   P   D   G 390       400       410       420       430
       *    *    *    *    *    *    *    *    *    *
    TAC TGC CAG GCT ACT ATG TTC GAA CTT ATG AAA TTT AAC CAT GTT TGT ATC
    ATG ACG GTC CGA TGA TAC AAG CTT GAA TAC TTT AAA TTG GTA CAA ACA TAG
     Y   C   Q   A   T   M   F   E   L   M   K   F   N   H   V   C   I 440       450       460       470       480
       *    *    *    *    *    *    *    *    *    *
    CCA TAT TGG AAA TGT GAT GGC GAT GAC TGT GGC GAT TCA
    GGT ATA ACC TTT ACA CTA CCG CTA CTG ACA CCG CTA AGT
     P   Y   W   K   C   D   G   D   D   C   G   D   S
```

```
                                              760                                                          
         730         740         750         *                                                              
         *           *           *           AAT GAT GAA TCC TGG GAC TGT                                    
    GAC TGT GGT GAC TCC GAT GAA CTG GGT TGC AAA GGA AAA GAA
    CTG ACA CCA CTG AGG CTA CTT GAC CCA ACG TTT CCT TTT CTT
    D   C   G   D   S   D   E   L   G   C   N   K   G   K   E 770         780         790         800         810
    *           *           *           *           *
    AGA ACA TGT GCT GAA ATA TAT TGC GAG CAA AAT TGT ACC CAA TTA AAT
    TCT TGT ACA CGA CTT TAT ATA ACG CTC GTT TTA ACA TGG GTT AAT TTA
    R   T   C   A   E   I   Y   C   E   Q   N   C   T   Q   L   N 820         830         840         850         860
                 *           *           *           *           *
    GAG GAG GAT TTA TCT GCT CCT GTA CAG CTG GGT TCG ATG TTT
    CTC CTC CTA AAT AGA CGA GGA CAT GTC GAC CCA AGC TAC AAA
    E   E   D   L   S   A   P   V   Q   L   G   S   M   F 870         880         890         900         910
            *           *           *           *           *
    TTT GAC AGA ACC TCC TGT CTA GAT ATC AAT GAA TGT CAA CCA TTT GGG
    AAA CTG TCT TGG AGG ACA GAT CTA TAG TTA CTT ACA GTT GGT AAA CCC
    F   D   R   T   S   C   L   D   I   N   E   C   Q   P   F   G 920         930         940         950         960
    *           *           *           *           *
    TGT CCC CAG CAC TGC AGA AAT ACC AAA TAT GAA AGT GTC
    ACA GGG GTC GTG ACG TCT TTA TGG TTT ATA CTC TCA CAG
    C   P   Q   H   C   R   N   T   K   Y   E   S   V

ACT TGT TGA CGT TAT AAT GGA CCT TCA AGT CAG
    TGA ACA ACT GCA ATA TTA CCT GGA AGT TCA GTC
    T   C   *
```

*FIG. 6 cont.*

```
         970*                 980*                 990*                1000*
    * GCT GAT GGC TTC ACG ATG AGT GAC CGC CCT GGA AAA CGA TGT
TGT ACA CGA CTA CCG AAG TGC TCA TCA CTG GCG GGA CCT TTT GCT ACA
    *   A   D   G   F   T   M   S   D   R   P   G   K   R   C
1010*                1020*                1030*                1040*
GCA GCT GAG CTC AGC GGT AGC TCT CCT TTG CTA CTG CCT CTT GAC CGA
CGT CGA CTC GAG TCG CCA TCG AGA GGA AAC GAT GAC GGA GAA CTG GCT
  A   A   E   L   S   G   S   S   P   L   L   L   P   L   D   R
1060*                1070*                1080*                1090*
ATT CGA AAA TAT AAT CTC TCA TCT GAG GTT CAA GCT TTC TCA GAG TGG
TAA GCT TTT ATA TTA GAG AGT AGA CTC AAG GTT CGA AAG AGT CTC ACC
  I   R   K   Y   N   L   S   S   E   V   Q   A   F   S   E   W
1110*                1120*                1130*                1140*
GAT GAG GAA TAT ATC CAA GCT GTT GAT TAT GAT TGG GAT TAT CTT CAA
CTA CTC CTT ATA TAG GTT CGA CAA CTA ATA CTA ACC CTA ATA GAA GTT
  D   E   E   Y   I   Q   A   V   D   Y   D   W   D   Y   L   Q
1160*                1170*                1180*                1190*                1200*
ATA GGC CTC AGT GTT GTG TAT TAC ACT GTG CGA GGG GAG GGC TCT AGG
TAT CCG GAG TCA CAA CAC ATA ATG TGA CAC GCT CCC CTC CCG AGA TCC
  I   G   L   S   V   V   Y   Y   T   V   R   G   E   G   S   R
```

FIG. 6 cont.

```
                  1210        1220        1230        1240
                    *           *           *           *
TTT GGT GCT ATC AAA CGT GCC TAC ATC CCC AAC TTT GAA TCC GGC CGC
AAA CCA CGA TAG TTT GCA GGG ATG TAG GGG TTG AAA CTT AGG CCG GC
                                                              *

1250        1260        1270        1280        1290
    *           *           *           *           *
AAT AAT CTT GTG CAG GAA GTT GAC CTG AAA TAC GTA ATG CAG
TTA TTA GAA CAC GTC CTT CAA CTG GAC TTT ATG CAT TAC GT
                                                      *

1300        1310        1320        1330        1340
    *           *           *           *           *
CCA GAT GGA ATA GCA GTG GAC TGG GTT GGA CAT ATT TAC TGG TCA
GGT CTA CCT TAT CGT CAC CTG ACC CAA CCT GTA TAA ATG ACC AGT
  P   D   G   I   A   V   D   W   V   G   H   I   Y   W   S 1350        1360        1370        1380        1390
                *           *           *           *           *
GAT GTC AAG AAT AAA CGC ATT GAG GTG GCT AAA CTT GAT GGA AGG TAC
CTA CAG TTC TTA TTT GCG TAA CTC CAC CGA TTT GAA CTA CCT TCC ATG
  D   V   K   N   K   R   I   E   V   A   K   L   D   G   R   Y 1400        1410        1420        1430        1440
    *           *           *           *           *
AGA AAG TGG CTG ATT TCC ACT GAC CAA CCA GCT GCT ATT GCT
TCT TTC ACC GAC TAA AGG TGA CTG GTT GGT CGA CGA TAA CGA
  R   K   W   L   I   S   T   D   Q   P   A   A   I   A
```

```
                1450       *       1460       *       1470       *       1480       *
         *        *         *        *         *        *         *        *
        GTG AAT CCC AAA CTA GGG CTT ATG TTC TGG ACT GAC TGG GGA AAG GAA
        CAC TTA GGG TTT GAT CCC GAA TAC AAG ACC TGA CTG ACC CCT TTC CTT
         V   N   P   K   L   G   L   M   F   W   T   D   W   G   K   E

1490       *       1500       *       1510       *       1520       *       1530       *
   *        *         *        *         *        *         *        *         *
  CCT AAA ATC GAG TCT GCC TGG ATG AAT GGA GAG GAC CTC AAC ATC CTG
  GGA TTT TAG CTC AGA CGG ACC TAC TTA CCT CTC CTG GAG TTG TAG GAC
   P   K   I   E   S   A   W   M   N   G   E   D   L   N   I   L

1540       *       1550       *       1560       *       1570       *       1580       *
   *        *         *        *         *        *         *        *         *
  GTT TTC GAG GAC CTT GGT TGG CCA ACT GGC CTT TCT ATC GAT TAT TTG
  CAA AAG CTC CTG GAA CCA ACC GGT TGA CCG GAA AGA TAG CTA ATA AAC
   V   F   E   D   L   G   W   P   T   G   L   S   I   D   Y   L

1590       *       1600       *       1610       *       1620       *       1630       *
   *        *         *        *         *        *         *        *         *
  AAC GAC CGA ATC TAC TGG AGT GAC TTC AAG GAG GAC CTG GTT ATT GAA ACC
  TTG CTG GCT TAG ATG ACC TCA CTG AAG TTC CTC CTG GAC CAA TAA CTT TGG
   N   D   R   I   Y   W   S   D   F   K   E   D   L   V   I   E   T

1640       *       1650       *       1660       *       1670       *       1680       *
   *        *         *        *         *        *         *        *         *
  ATA AAA TAT GAT GGG ACT GAT AGG AGA GTC ATT GCA AAG GAA ATG
  TAT TTT ATA CTA CCC TGA CTA TCC TCT CAG TAA CGT TTC CTT TAC
   I   K   Y   D   G   T   D   R   R   V   I   A   K   E   M
```

FIG. 6 cont.

```
      1690         1700          1710         1720
       *            *             *            *
AAC CCT TAC AGC CTG GAC ATC TTT GAA CAG TAC TGG ATA TCT
TTG GGA ATG TCG GAC CTG TAG AAA CTT GTC ATG ACC TAT AGA
 N   P   Y   S   L   D   I   F   E   Q   Y   W   I   S 1730         1740         1750         1760         1770
     *            *            *            *            *
AAG GAA AAG GGA GAA CTT TTT AAA CAA GTT TTA AAT GGG CAA TGC AAG
TTC CTT TTC CCT CTT GAA AAA TTT GTT CAA AAT TTA CCC GTT ACG TTC
 K   E   K   G   E   L   F   K   Q   V   L   N   G   Q   C   K 1780         1790         1800         1810         1820
     *            *            *            *            *
AAA ACG CTG GTA AAC CTT GTG CAC CCT TGG ACT CTC AAC CAA GTT CGA ATC
TTT TGC GAC CAT TTG GAA CAC GTG GGA ACC TGA GAG TTG GTT CAA GCT TAG
 K   T   L   V   N   L   V   H   P   W   T   L   N   Q   V   R   I 1830         1840         1850         1860         1870
     *            *            *            *            *
GAG CTC AGA TAC AAT AAG TCA GTG CCC GGG AAC CTT TGC AAA CAG
CTC GAG TCT ATG TTA TTC AGT CAC GGG CCC TTG GAA ACG TTT GTC
 E   L   R   Y   N   K   S   V   P   G   N   L   C   K   Q 1880         1890         1900         1910         1920
     *            *            *            *            *
TTT CAT CAA CTC TGC CTT CTG AGA CCT GGA GGA TAC AGC TGT GCC
AAA GTA GTT GAG ACG GAA GAC TCT GGA CCT CCT ATG TCG ACA CGG
 F   H   Q   L   C   L   L   R   P   G   G   Y   S   C   A

ATC TGC AGC CAC CAA GTT ATG
TAG ACG TCG GTG GTT CAA TAC
 I   C   S   H   Q   V   M
```

*FIG. 6 cont.*

```
            1930*           1940*           1950*           1960*
TGT CCC CAA GGC TCC AGC TTT ATA GAG GGG AGC ACC ACT GAG TGT GAT
ACA GGG GTT CCG AGG TCG AAA TAT CTC CCC TCG TGG TGA CTC ACA CTA
 C   P   Q   G   S   S   F   I   E   G   S   T   T   E   C   D
1970*           1980*           1990*           2000*
GCA GCC ATC GAA CTG CCT ATC AAC CTG CCC CCC CCA GGG AGC
CGT CGG TAG CTT GAC GGA TAG TTG GAC GGG GGG GGT TCC TCG                    *
 A   A   I   E   L   P   I   N   L   P   P   P   G   S                    *
                                                                       2010*
                                                                TGC AGG TGC ATG
                                                                ACG TCC ACG TAC
                                                                 C   R   C   M
2020*           2030*           2040*           2050*
CAC GGA AAT TGC TAT TTT GAT GAG ACT CCC AAA TGC AAG
GTG CCT TTA ACG ATA AAA CTA CTC TGA GGG TTT ACG TTC                        *
 H   G   N   C   Y   F   D   E   T   P   K   C   K                        *
                                                                       2060*
                                                            TTT TCA AAA
                                                            AAA AGT TTT
                                                             F   S   K
2070*           2080*           2090*           2100*
TGT CCT AGC GGC TAC ACC GGA AAA TAT TGT GAA CTC CCC ATG GCG ATC CTC
ACA GGA TCG CCG ATG TGG CCT TTT ATA ACA CTT GAG GGG TAC CGC TAG GAG
 C   P   S   G   Y   T   G   K   Y   C   E   L   P   M   A   I   L
                                                                       2110*
2120*           2130*           2140*           2150*           2160*
GGC ATC TCT CCA ACA GGA GCA GTA ACC GCT GTG CTG TTG ACA ATC CTC
CCG TAG AGA GGT TGT CCT CGT CAT TGG CGA CAC GAC AAC TGT TAG GAG
 G   I   S   P   T   G   A   V   T   A   V   L   L   T   I   L
```

*FIG. 6 cont.*

```
      2170        2180        2190        2200
      *           *           *           *
TTG ATC GTC GTA ATT GGA GCT CTG GCA ATT TTC TTC CAC TAT
AAC TAG CAG CAT TAA CCT CGA GAC CGT TAA AAG AAG GTG ATA
 L   I   V   V   I   G   A   L   A   I   F   F   H   Y 2210        2220        2230        2240        2250
      *           *           *           *           *
AGA AGG ACC GGC TCC AAG CTT CCT GCT CTG GAC CCC AAG GGA TTC CCA AGC TTA
TCT TCC TGG CCG AGG TTC GAA GGA CGA GAC CTG GGG TTC CCT AAG GGT TCG AAT
 R   R   T   G   S   K   L   P   A   L   D   P   K   G   F   P   S   L 2260        2270        2280        2290        2300
      *           *           *           *           *
AGC AGT CTC GTC GAT CTT GAA ATG AAC CCC GGG AAT GGG GTG ACC TTC AGA
TCG TCA GAG CAG CTA GAA CTT TAC TTG GGG CCC TTA CCC CAC TGG AAG TCT
 S   S   L   V   D   L   E   M   N   P   G   N   G   V   T   F   R 2310        2320        2330        2340        2350
      *           *           *           *           *
TCA GGG GCA GAT CTT GAA ATG GAT ATT TAA CCT GTG TCT GGT TTT GGA CCT
AGT CCC CGT CTA GAA CTT TAC CTA TAA ATT GGA CAC AGA CCA AAA CCT GGA
 S   G   A   D   L   E   M   D   I   *   G   V   S   G   F   G   P 2360        2370        2380        2390        2400
      *           *           *           *           *
GAG ACT GCT ATT GAC AGG TCA AAC ATG GCA ATG AGT GAA GAC TTT GTC ATG
CTC TGA CGA TAA CTG TCC AGT TTG TAC CGT TAC TCA CTT CTG AAA CAG TAC
 E   T   A   I   D   R   S   N   M   A   M   S   E   D   F   V   M
```

*FIG. 6 cont.*

```
        *        2410           *        2420           *        2430           *        2440           *
GAA  ATG  GGG  AAG  CAG  CCC  ATA  ATA  TTT  GAA  AAC  CCA  ATG  TAC  TCA  GCC
 E    M    G    K    Q    P    I    I    F    E    N    P    M    Y    S    A

*        2450           *        2460           *        2470           *        2480           *        2490           *
AGA  GAC  ACT  GCT  GTC  AAA  GTG  GTT  CAG  CCA  ATC  AGT  CAG  ACT  GTA  TCT
 R    D    T    A    V    K    V    V    Q    P    I    S    Q    T    V    S

*        2500           *        2510           *        2520           *        2530           *        2540           *
GAA  AAT  GTG  GAT  AAT  AAG  GTG  CAC  CAA  AGT  TAT  ATA  CCC  GGG  TAT  CAT
 E    N    V    D    N    K    V    H    Q    S    Y    I    P    G    Y    H

*        2550           *        2560           *        2570           *        2580           *        2590           *
ATA  GTT  CCA  GAG  CTC  TTC  ACT  TAT  CCC  ATA  GCT  TCT  TCT  GAG  ACT  CAG
 I    V    P    E    L    F    T    Y    P    I    A    S    S    E    T    Q

*        2600           *        2610           *        2620           *        2630           *        2640           *
GTG  ACA  AAA  TGG  AAT  CTC  TTC  AAA  CGA  AAA  TCT  AAA  CAA  ACT  ACC  AAC
 V    T    K    W    N    L    F    K    R    K    S    K    Q    T    T    N
```

*FIG. 6 cont.*

```
       2650        2660        2670        2680
          *           *           *           *
TTT GAA AAT CCA ATC TAT GCA CAG ATG GAG AAC GAG CAA AAG AAG GAA AGT
AAA CTT TTA GGT TAG ATA CGT GTC TAC CTC TTG CTC GTT TTC CTT TCA
 F   E   N   P   I   Y   A   Q   M   E   N   E   Q   K   K   E   S 2690        2700        2710        2720        2730
          *           *           *           *           *
GTT GCT GCG ACA CCA CCT CCA CCT TCA TCG CTC CCT GCT AAG CCT AAG
CAA CGA CGC TGT GGT GGA GGT GGA AGT AGC GAG GGA CGA TTC GGA TTC
 V   A   A   T   P   P   P   P   S   S   L   P   A   K   P   K 2740        2750        2760        2770        2780
          *           *           *           *           *
CCT CCT TCG AGA AGA GAC CTG CCA ACT CCA GGT TAT TCT GCA ACA GAC GAA GAC
GGA GGA AGC TCT TCT CTG GAC GGT TGA GGT CCA ATA AGA CGT TGT CTG CTT CTG
 P   P   S   R   R   D   L   P   T   P   G   Y   S   A   T   D   E   D 2790        2800        2810        2820        2830
          *           *           *           *           *
ACT TTT AAA GAC AAT ACC GCA AAT CTT GTT AAA GAA GAC TCT GAA GTA TAG
TGA AAA TTT CTG TTA TGG CGT TTA GAA CAA TTT CTT CTG AGA CTT CAT ATC
 T   F   K   D   N   T   A   N   L   V   K   E   D   S   E   V   *
```

*FIG. 6 cont.*

CAS RECEPTOR (GP330)
CYTOPLASMIC SEQUENCES
(~200aa)

RRTGSLLPALPKLPLPSLSSLVKPSENGNGVTFRSGADLNMDIGVSGFGPETAID
RSMAMSEDFVMEMGKQPIIFENPMYSARDSAVKVVQPIQVTVSENVDNKN
YGSPINPSEIVPETNPTSPAADGTQVTKWNLFKRKSKQTTNFENPIYAQMENE
QKESVAATPPPSPSLPAKPKPPSRRDPTPTYSATEDTFKDTANLVKEDSEV

SEQUENCE ALIGNMENT OF SH3-BINDING MOTIFS

Table 5. Sequence Alignment of SH3-Binding Motifs

| SH3-Binding Motif | $P_{-5}$ | $P_{-4}$ | $P_{-3}$ | $P_{-2}$ | $P_{-1}$ | $P_0$ | $P_1$ | $P_2$ | $P_3$ | $P_4$ | $P_5$ |
|---|---|---|---|---|---|---|---|---|---|---|---|
| PI3K library consensus | | | R | X | L | P | P | R | P | X | X |
| Src library consensus | | | R | X | L | P | P | L | P | R | Φ |
| Murine 38P1 (267-277) | P | T | M | P | P | P | P | P | P | V | P |
| Murine 38P2-40 (2-12) | P | A | Y | P | P | P | P | P | P | V | P |
| Mouse Sos1 (1146-1156) | E | V | P | V | P | P | L | V | P | P | R |
| Mouse Sos1 (1174-1184) | H | L | D | (S) | P | P | P | I | P | P | R |
| Mouse Sos1 (1285-1295) | H | S | I | (A) | G | P | (A) | V | P | P | R |
| Human dynamin (785-795) | A | P | A | V | P | P | P | R | P | G | S |
| Human dynamin (811-821) | G | A | (P) | P | V | P | S | R | P | G | A |

FIG. 7

Table 5. Sequence Alignment of SH3-Binding Motifs

| SH3-Binding Motif | P_-5 | P_-4 | P_-3 | P_-2 | P_-1 | P_0 | P_1 | P_2 | P_3 | P_4 | P_5 |
|---|---|---|---|---|---|---|---|---|---|---|---|
| Human PI3K p85 (91-101) | P | P | R | P | L | P | V | A | P | G | S |
| Human PI3K p85 (303-313) | P | A | P | A | L | P | P | K | P | P | K |
| Human GTPase-activated protein CDC42 (250-260) | A | P | K | P | M | P | P | R | P | P | L |
| Mouse formin (873-883) | A | P | T | P | P | P | L | P | P | P | L |
| Rat muscarinic acetylcholine receptor (277-287) | P | A | L | P | P | P | P | P | P | V | P |
| v-Fgr (12-22) | R | P | R | P | P | P | P | R | P | P | T |
| Human HK2 (63-103) | G | V | R | P | L | P | P | L | P | D | P |
| Human proacrosin (333-343) | P | P | R | P | L | P | P | R | P | P | A |
| | | | | | | | | | | | |
| SH3-binding site consensus | | | x | p | Φ | P | p | x | P | | |

Capital letters represent amino acid residues in the SH3-binding motifs. X represents nonconserved residues. Φ represents hydrophobic residues and p represents residues that tend to be proline. Amino acids that are completely conserved are boxed. In the case of 3BP1, the amino acid position numbers count from the beginning of the partial cDNA sequence reported by Ciochetti et al. (1992)

| | | | | | | | | SH3 CONSENSUS |
|---|---|---|---|---|---|---|---|---|
| x | p | Φ | p | p | x | P | - | CAS - PEP 1 |
| p | s | l | p | a | k | l | P - | CAS - PEP 2 |
| s | l | L | P | a | | l | P - | CAS - PEP 3 |
| p | a | L | P | k | | l | P - | |

FIG. 7 cont.

CAS-CYP-SH3BR + SH3s

CAS RECEPTOR (GP330) CYTOPLASMIC SEQUENCES (~200aa)

RRTGSLLPALPKLPLPSLSSLVKPSENGNGVTFRSGADLNMDIGVSGFGPETAID
RSMAMSEDFVMEMGKQPIIFENPMYSARDSAVKVVQPIQVTVSENVDNKN
YGSPINPSEIVPETNPTSPAADGTQVTKWNLFKRKSKQTTNFENPIYAQMENE
QKESVAATPPPSPSLPAKPKPPSRRDPTPTYSATEDTFKDTANLVKEDSEV pTyr PEPTIDE SPECIFICITY OF SH2 DOMAINS OF p85 C-TERMINAL SH2

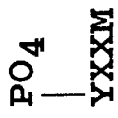

$$\overset{PO_4}{\underset{YXXM}{|}}$$

| Binding Sites in Proteins | | |
|---|---|---|
| Sequence | Protein | Tyr Location |
| Known binding sites | | |
| ESDGGYMDMSKDESVDYVPMLD | Human PDGF receptor B | (Y740, Y751) |
| EEEEEYMPMEDLYLD/LP | Mouse polyoma MT | (Y315) |
| QGVDTYVEMRP | Mouse colony-stimulating factor 1 receptor | (Y721) |
| DSTNEYMDMKP | Human c-Kit | (Y721) |

FIG. 9

Binding Sites in Proteins

| Sequence | Protein | Tyr Location |
|---|---|---|
| Possible sites on proteins known to bind p85 | | |
| GPGGDYAAMGACPASEQGYEEMRA | Human ErbB3 | (Y1257, Y1270) |
| TPDEDYEYMNRQRDGGGPGGDYAAMGA | Human ErbB3 | (Y1241, Y1257) |
| CTDVYMVMVK | Human ErbB3 | (Y922) |
| SPSSGYMPMNQ | Human ErbB3 | (Y1,035) |
| DEDEEYEYMNR | Human ErbB3 | (Y1,178) |
| LEELGYEYMDV | Human ErbB3 | (Y1,203) |
| EELSNYICMGG | Rat insulin receptor substrate 1 | (Y460) |
| VSIEEYTEMMP | Rat insulin receptor substrate 1 | (Y546) |
| HTDDGYMPMSP | Rat insulin receptor substrate 1 | (Y608) |
| KGNGDYMPMSP | Rat insulin receptor substrate 1 | (Y628) |
| VDPNGYMMMSP | Rat insulin receptor substrate 1 | (Y658) |
| PCTGDYMNMSP | Rat insulin receptor substrate 1 | (Y727) |
| TGSEEYMNMDL | Rat insulin receptor substrate 1 | (Y939) |
| NSRGDYMTMQI | Rat insulin receptor substrate 1 | (Y987) |
| VAPVSYADMRT | Rat insulin receptor substrate 1 | (Y1,010) |
| ERENEYMPMAPQIHLYSQ/RE | Hamster polyoma MT | (298) |
| LSNPTYSVMRS | Mouse polyoma MT | (Y250) |
| CPEKVYELMRA | Mouse v-Abl oncoprotein | (Y355) |

| Binding Sites in Proteins | | |
|---|---|---|
| Sequence | Protein | Tyr Location |
| Other possible sites | | |
| NTTV<u>D</u>YVYMSHG<u>D</u>NG<u>D</u>YVYMN | Human papaloma virus 11 E5b | (Y59, Y70) |
| NCN<u>D</u>DYTMHYTT<u>D</u>G<u>D</u>YIYMN | Human papaloma type 6b E5b | (Y57, y68) |
| YVN<u>D</u>IYLYMRHLER<u>E</u>FKVRT<u>D</u>YMAMQE | Starfish G2 cyclin B | (Y149, Y165) |
| NQE<u>E</u>AYVTMSS | Human IL-7 receptor | (Y449) |
| FIASKYEDMYP | Human G2 cyclin b | (Y255) |
| LGSQSYEDMRG | Mouse B cell CD 19 | (Y493) |
| E<u>D</u>ADSYENMDK | Mouse B cell CD 19 | (Y522) |
| ELQ<u>D</u>DYEDMME | Human red cell band 3 | (Y8) |
| AACVVYEDMSH | Human T cell CD7 | (Y222) |
| APP<u>EE</u>YVPMVK | Chick pp125 | (Y926) |
| I<u>D</u>SCTYEAMYN | Human c-cbl proto-oncogene | (Y731) |
| VAVA<u>E</u>YEIMEQ | Chicken dystrophin | (Y974) |
| MSV<u>ES</u>YEEMKM | Aspergillus kinesin-like Bimc | (Y462) |
| HQTR<u>E</u>YESMIE | C. elegans kinesin-like Unc-104 | (Y633) |
| TLQN<u>E</u>YELMRE | Human Rb-associated protein 110 | (Y692) |
| GG<u>EE</u>IYVVMLG | Rat s-myc proto-oncogene | (Y247) |
| LEG<u>E</u>HYINMAV | Avian E8 virus sea oncop otein | (Y331) |
| <u>E</u>IT<u>E</u>QYIYMVM | Mouse Esk STY kinase | (Y596) |
| T<u>E</u>QYIYMVMEC | Mouse Esk STY kinase | (Y598) |

```
TTGCAGACCT AAAGGAGCGT TCGCTAGCAG AGGCGCTGCC GGTGCGGTGT GCTACGCGCG                60

CCCACCTCCC GGGGAAGGAA CGGCGAGGCC GGGGACCGTC GCGGAG ATG GAT CGC               115
                                                 Met Asp Arg
                                                  1

GGG CCG GCA GTG GCG TGC ACG CTG CTC CTG GCT CTC GTC GCC TGC                   163
Gly Pro Ala Val Ala Cys Thr Leu Leu Leu Ala Leu Val Ala Cys
 5                  10                  15

CTA GCG CCG GCC AGT GGC CAA GAA TGT GAC AGT GCG CAT TTT CGC TGT               211
Leu Ala Pro Ala Ser Gly Gln Glu Cys Asp Ser Ala His Phe Arg Cys
 20              25                  30                  35

GGA AGT GGG CAT TGC ATC CCT GCA GAC TGG ATT GGC GAT GCG TGT GAT GGG ACC AAA   259
Gly Ser Gly His Cys Ile Pro Ala Asp Trp Ile Gly Asp Ala Cys Asp Gly Thr Lys
             40              45              60                      50

GAC TGT TCA GAT GAC CAT TGC CAG GAT GAA AGT GAG GGA GGA CAA GGA TGC GTG ACC TGC  307
Asp Cys Ser Asp Asp His Cys Gln Asp Glu Ser Glu Gly Gly Gln Gly Ala Val Thr Cys
             55              75                      65

CAG CAG GGC TAT TTC AAG TGC CAG GGA GGA CAA GGA TGC ATC CCC AGC               355
Gln Gln Gly Tyr Phe Lys Cys Gln Gly Gly Gln Gly Cys Ile Pro Ser
 70              75              80

TCC TGG GTG TGT GAC CAA GAT CAA GAT GAT TGT GAT GGC TCA GAT GAA              403
Ser Trp Val Cys Asp Gln Asp Gln Asp Asp Cys Asp Gly Ser Asp Glu
 85              90              95
```

FIG. 10

| | | | | | | | | | | |
|---|---|---|---|---|---|---|---|---|---|---|
| CGT Arg 100 | CAA Gln | GAT Asp | TGC Cys | TCA Ser | CAA Gln 105 | AGT Ser | ACA Thr | TCA Ser 110 | CAT His | CAG Gln | ATA Ile | ACA Thr | TGC Cys 115 | 451 |
| TCC Ser | ATT Ile | GGT Gly | CAG Gln | TGT Cys 120 | ATC Ile | CCA Pro | AGT Ser | TAC Tyr 125 | GAA Glu | TGC Cys | AGG Arg | TGC Cys | GAC Asp | CAC His | GTC Val 130 | AGA Arg | 499 |
| GAC Asp | TGC Cys | GAT Asp 135 | GGA Gly | GCT Ala | GAT Asp | GAG Glu | AAT Asn 140 | GAC Asp | TGC Cys | CAG Gln | TAC Tyr | CCA Pro 145 | ACA Thr | TGT Cys | 547 |
| GAG Glu | CAG Gln | CTT Leu 150 | CCC Pro | GGG Gly | AAT Asn 155 | GAT Asp | TGT Cys | GCC Ala | TGC Cys | TAT Tyr | AAC Asn | ACC Thr 160 | AGT Ser | CAG Gln | AAG Lys | 595 |
| TGT Cys | GAT Asp 165 | TGG Trp | AAA Lys | GTT Val | GAT Asp | TGC Cys | CGC Arg 170 | GAC Asp | TCC Ser | TCA Ser | GAT Asp 175 | GGC Gly | ATC Ile | AAC Asn | TGC Cys | 643 |
| ACT Thr 180 | ATA Ile | TGC Cys | TTG Leu | CAC His 185 | AAT Asn | GAG Glu | TTT Phe | TCA Ser | AAT Asn 190 | GGA Gly | GAG Glu | TGT Cys 195 | 691 |
| ATC Ile | CCT Pro | CGT Arg | GCT Ala | TAT Tyr 200 | GTC Val | TGT Cys | GAC Asp | CAT His | GAC Asp 205 | TGC Cys | CAA Gln | GAC Asp | TGC Cys | GGC Gly | 739 |

FIG. 10 cont.

| | | | | | | | | | | | | | | | | |
|---|---|---|---|---|---|---|---|---|---|---|---|---|---|---|---|---|
| AGT Ser | GAT Asp | GAA Glu | CAT His | GCT Ala | TGC Cys | AAC Asn | TAT Tyr | CCG Pro | ACC Thr | TGC Cys | GGT Gly | GGT Gly | TAC Tyr 225 | CAG Gln | TTC Phe | 787 |
| ACT Thr | TGC Cys | CCC Pro 230 | AGT Ser | GGC Gly | CGA Arg | TGC Cys | ATT Ile 235 | TAT Tyr | CAA Gln | AAC Asn | TGG Trp | GTT Val 240 | TGT Cys | GAT Asp | GGA Gly | 835 |
| GAA Glu | GAT Asp 245 | GAC Asp | TGT Cys | AAA Lys | GAT Asp | AAT Asn 250 | GGA Gly | GAT Asp | GAA Glu | GGA Gly | TGT Cys 255 | AGC Ser | GGT Gly | | | 883 |
| CCT Pro 260 | CAT His | GAT Asp | GTT Val | CAT His | AAA Lys | TGT Cys 265 | TCC Ser | CCA Pro | AGA Arg | GAA Glu | GAA Glu 270 | TCT Ser | TGC Cys | CCA Pro | GAG Glu 275 | 931 |
| TCG Ser | GGA Gly | CGA Arg | TGC Cys | ATC Ile | TAT Tyr | ATT Ile | AAA Lys | GTT Val 285 | TGT Cys | GAT Asp | GGG Gly | GAT Asp | ATT Ile | TTA Leu 290 | GAT Asp | 979 |
| TGC Cys | CCA Pro | GGA Gly | AGA Arg 295 | TGC Cys | ATC Ile | GAA Glu | GAT Asp | GAA Glu | AAC Asn | AAC Asn 300 | AGT Ser | ACC Thr | ACC Thr | GGA Gly | AAA Lys 305 | 1027 |
| AGT Ser | ATG Met | ACT Thr | CTG Leu 310 | TGC Cys | TCT Ser | GCC Ala | TTG Leu | AAC Asn 315 | TGC Cys | CAG Gln | TAC Tyr | CAG Gln 320 | TAC Tyr | CAT His | GAG Glu | 1075 |

```
ACG CCG TAT GGA GGA GCG TGT TTT TGT CCC CCA GGT TAT ATC ATC AAC          1123
Thr Pro Tyr Gly Gly Ala Cys Phe Cys Pro Pro Gly Tyr Ile Ile Asn
    325                     330             335

CAC AAT GAC AGC CGT ACC TGT GTT GAG TTT GAT TGC CAG ATA TGG              1171
His Asn Asp Ser Arg Thr Cys Val Glu Phe Asp Cys Gln Ile Trp
340             345             350                 355

GGA ATT TGT GAC CAG AAG TGT GAA AGC CGA GAT TGC CAC CTG AAA GCT          1219
Gly Ile Cys Asp Gln Lys Cys Glu Ser Arg Asp Cys His Leu Lys Ala
            360             365                 370

CAC TGT GAC CAG GAA GAA GAG CCT GGC CGT CGT TAT TGC CAG TAT TGC          1267
His Cys Asp Gln Glu Glu Glu Pro Gly Arg Arg Tyr Cys Gln Tyr Cys
                375                 380             385

AAT GAT TCC TTT GGG GAG TAT ATC TTG GAG CGT CAG GGA GGT CGG GAT          1315
Asn Asp Ser Phe Gly Glu Tyr Ile Leu Glu Arg Gln Gly Gly Arg Asp
        390                 395             400

TTG TTA ATT GGT GAT ATT CAT GAG GCC ATT ATC TTC TCC AGC TTC CGG AGC     1363
Leu Leu Ile Gly Asp Ile His Glu Ala Ile Ile Phe Ser Arg Ser
    405                 410             415

TCT CAG AAT CGT GGA GTG GTG GCC GTG GCT GTG GGT GAG CAC TAT CTG         1411
Ser Gln Asn Arg Gly Val Val Ala Val Ala Val Gly Glu His Tyr Leu
420                 425             430             435
```

```
CAA AGA GTT TTT TGG ACA GAC ACC GTG CAA AAT AAG GTT TTT TCA GTT    1459
Gln Arg Val Phe Trp Thr Asp Thr Val Gln Asn Lys Val Phe Ser Val
                440                     445                 450

GAC ATT AAT GGT TTA AAT ATC CAA GAG CTC AAT GTT TCT GTT GAA        1507
Asp Ile Asn Gly Leu Asn Ile Gln Glu Leu Asn Val Ser Val Glu
                455                 460                 465

ACC CCA GAG AAC CTG GCT GTG GAC TGG GTT AAT AAT AAA                1555
Thr Pro Glu Asn Leu Ala Val Asp Trp Val Asn Asn Lys
                470                 475                 480

GTG GAA ACC GTC AAC CGC ATA GAT ATG GTA AAT TTG GAT GGA AGC        1603
Val Glu Thr Val Asn Arg Ile Asp Met Val Asn Leu Asp Gly Ser
                485                 490                 495

TAT CGG GTT GAC CTT ATA ACT GAA AAC TTG GGG CAT CCT AGA GGA ATT    1651
Tyr Arg Val Asp Leu Ile Thr Glu Asn Leu Gly His Pro Arg Gly Ile
                500                 505                 510  515

GCC GTG GAC CCA ACT GTT GGT TAT TTA TTT TCA GAT TGG GAG AGC        1699
Ala Val Asp Pro Thr Val Gly Tyr Leu Phe Ser Asp Trp Glu Ser
                520                 525                 530

CTT TCT GGG GAA CCT AAG CTG GAA AGG GCA TTC ATG GAT GGC AGC AAC    1747
Leu Ser Gly Glu Pro Lys Leu Glu Arg Ala Phe Met Asp Gly Ser Asn
                535                 540                 545
```

*FIG. 10 cont.*

| | | | | | | | | | | |
|---|---|---|---|---|---|---|---|---|---|---|
| CGT Arg | AAA Lys | GAC Asp | TTG Leu | GTG Val | AAA Lys | ACA Thr | AAG Lys 555 | CTG Leu | GGA Gly | TGG Trp | CCT Pro | GCT Ala 560 | GGG Gly | GTA Val | ACT Thr | 1795 |

Row by row:

CGT AAA GAC TTG GTG AAA ACA AAG CTG GGA TGG CCT GCT GGG GTA ACT    1795
Arg Lys Asp Leu Val Lys Thr Lys Leu Gly Trp Pro Ala Gly Val Thr
           550                 555                 560

CTG GAT ATG ATA TCG AAG CGT AAG CTG TAC TGG GTT GAC TCT CGG TTT GAT    1843
Leu Asp Met Ile Ser Lys Arg Lys Leu Tyr Trp Val Asp Ser Arg Phe Asp
       565                 570                 575

TAC ATT GAA ACT GTA ACT TAT GAT GGA ATT CAA AGG AAG ACT GTA GTT    1891
Tyr Ile Glu Thr Val Thr Tyr Asp Gly Ile Gln Arg Lys Thr Val Val
 580                 585                 590                 595

CAT GGA TCC CTC ATT CCT CAT CCC TTT GGA GTA AGC TTA TTT GAA    1939
His Gly Ser Leu Ile Pro His Pro Phe Gly Val Ser Leu Phe Glu
               600                 605                 610

GGT CAG GTG TTT ACA GAT TGG ACA CAA GTG GCC ATG CTG CTG GCA    1987
Gly Gln Val Phe Thr Asp Trp Thr Gln Val Ala Met Val Leu Ala
       615                 620                 625

AAC AAG TTC ACA GAG ACC AAC CCA TAC TAC TAC CAG GCT TCC CTG    2035
Asn Lys Phe Thr Glu Thr Asn Pro Tyr Tyr Tyr Gln Ala Ser Leu
           630                 635                 640

AGG CCC TAT GGA GTG ACT GTT TAC CAT TCC CTC AGA CAG CCC TAT GCT    2083
Arg Pro Tyr Gly Val Thr Val Tyr His Ser Leu Arg Gln Pro Tyr Ala
 645                 650                 655

FIG. 10 cont.

```
ACC AAT CCG TGT AAA GAT AAC AAT GGG GGC TGT GAG CAG GTC TGT GTT    2131
Thr Asn Pro Cys Lys Asp Asn Asn Gly Gly Cys Glu Gln Val Cys Val
660             665             670             675

CTC AGC CAC AGA ACA GAT AAT GAT GGT TTG TTC CGT TGC AAG TGC        2179
Leu Ser His Arg Thr Asp Asn Asp Gly Leu Phe Arg Cys Lys Cys
        680             685             690

ACA TTC GGC TTC CAA CTG GAT ACA GAT GAG CGC TGC ATT GCT GTT        2227
Thr Phe Gly Phe Gln Leu Asp Thr Asp Glu Arg Cys Ile Ala Val
        695             700             705

CAG AAT TTC CTC ATT TTT TCA TCC CAA GTT GCT ATT CGT GGG ATC CCG    2275
Gln Asn Phe Leu Ile Phe Ser Ser Gln Val Ala Ile Arg Gly Ile Pro
        710             715             720

TTC ACC TTG TCT ACC CAG GAA GAT GTC ATG GTT CCA GTT TCG GGG AAT    2323
Phe Thr Leu Ser Thr Gln Glu Asp Val Met Val Pro Val Ser Gly Asn
725             730             735

CCT TCT TTT GTC GGG GTT TTT GAT TTT GAT GCC CAG GAC AGC ACT ATC    2371
Pro Ser Phe Val Gly Val Phe Asp Phe Asp Ala Gln Asp Ser Thr Ile
740             745             750             755

TTT TTT TCA GAT ATG TCA AAA CAC ATG ATT TTT AAG CAA AAG ATT GAT    2419
Phe Phe Ser Asp Met Ser Lys His Met Ile Phe Lys Gln Lys Ile Asp
        760             765             770
```

FIG. 10 cont.

| | | | | | | | | | |
|---|---|---|---|---|---|---|---|---|---|
| GGC Gly | ACA Thr | GGA Gly Arg 775 | AGA | GAA Glu | ATT Ile | CTC Leu | GCA Ala 780 | AAC Asn | AGG Arg | GTG Val | GAA Glu | AAT Asn 785 | GTT Val | GAA Glu | 2467 |
| AGT Ser | TTG Leu | GCT Ala 790 | TTT Phe | GAT Asp | TGG Trp | ATT Ile | TCA Ser 795 | AAT Asn | CTC Leu | TAT Tyr | TGG Trp 800 | ACA Thr | GAC Asp | TCT Ser | 2515 |
| CAT His | TAC Tyr 805 | AAG Lys | AGT Ser | ATC Ile | AGT Ser | GTC Val 810 | ATG Met | AGG Arg | CTA Leu | GCT Ala | GAT Asp 815 | AAA Lys | ACG Thr | AGA Arg | CGC Arg | 2563 |
| ACA Thr 820 | GTA Val | GTT Val | CAG Gln | TAT Tyr | TTA Leu 825 | AAT Asn | CCA Pro | CGG Arg | TCG Ser | GTG Val 830 | GTA Val | CAT His | CCT Pro 835 | 2611 |
| TTT Phe | GCC Ala | GGG Gly | TAT Tyr | CTA Leu 840 | TTC Phe | TTC Phe | GAT Asp | TGG Trp | TGG Trp 845 | TTC Phe | CGT Arg | CCT Pro | GCT Ala | AAA Lys 850 | ATT Ile | 2659 |
| ATG Met | AGA Arg | GCA Ala | TGG Trp 855 | AGT Ser | GAC Asp | GGA Gly | TCT Ser | CAC His 860 | TTG Leu | CCT Pro | GTA Val | ATA Ile 865 | AAC Asn | ACT Thr | 2707 |
| ACT Thr | CTT Leu | GGA Gly Trp 870 | TGG | CCC Pro | AAT Asn | GGC Gly | TTG Leu 875 | GCC Ala | ATC Ile | GAT Asp | TGG Trp | GCT Ala 880 | TCA Ser | CGA Arg | 2755 |

FIG. 10 cont.

| TTG Leu | TAC Tyr 885 | TGG Trp | GTA Val | GAT Asp | GCC Ala | TAT Tyr 890 | TTT Phe | GAT Asp | AAA Lys | ATT Ile | GAG Glu 895 | CAC His | AGC Ser | ACC Thr | TTT Phe | 2803 |
| GAT Asp | GGT Gly 900 | TTA Leu | GAC Asp | AGA Arg | AGA Arg | AGA Arg 905 | CTG Leu | GGC Gly | CAT His | ATA Ile 910 | GAG Glu | CAG Gln | ATG Met | ACA Thr | CAT His 915 | 2851 |
| CCG Pro | TTT Phe | GGA Gly | CTT Leu | GCC Ala 920 | ATC Ile | TTT Phe | GGA Gly | GAG Glu | CAT His 925 | TTA Leu | TTT Phe | TTT Phe | ACT Thr | GAC Asp 930 | TGG Trp | 2899 |
| AGA Arg | CTG Leu | GGT Gly | GCC Ala 935 | ATT Ile | ATT Ile | CGA Arg | GTC Val | AGG Arg | AAA Lys | GCA Ala | GAT Asp 940 | GGT Gly | GGA Gly 945 | GAA Glu | ATG Met | 2947 |
| ACA Thr | GTT Val | ATC Ile | CGA Arg | AGT Ser | GGC Gly 950 | ATT Ile | GCT Ala | TAC Tyr 955 | ATA Ile | CTG Leu | CAT His | TTG Leu 960 | AAA Lys | TCG Ser | TAT Tyr | 2995 |
| GAT Asp | GTC Val 965 | AAC Asn | ATC Ile | CAG Gln | ACT Thr | GGT Gly 970 | TCT Ser | AAC Asn | GCC Ala | TGT Cys | AAT Asn 975 | CAA Gln | CCC Pro | ACG Thr | CAT His | 3043 |
| CCT Pro | AAC Asn 980 | GGT Gly | GAC Asp | TGC Cys | AGC Ser 985 | CAC His | TTC Phe | TGC Cys | TTC Phe | CCG Pro 990 | GTG Val | CCA Pro | AAT Asn | TTC Phe | CAG Gln 995 | 3091 |

FIG. 10 cont.

```
CGA GTG TGT GGG TGC CCT TAT GGA ATG AGG CTG GTC TCC AAT CAC TTG      3139
Arg Val Cys Gly Cys Pro Tyr Gly Met Arg Leu Val Ser Asn His Leu
            1000                    1005                    1010

ACA TGC GAG GGG GAC CCA AAT GAA CCA CCC ACG GAG CAG TGT GGC          3187
Thr Cys Glu Gly Asp Pro Asn Glu Pro Pro Thr Glu Gln Cys Gly
            1015                    1020                    1025

TTA TTT TCC TTC CCC TGT AAA AAT GGC AGA TGT GTG CCC AAT TAC TAT      3235
Leu Phe Ser Phe Pro Cys Lys Asn Gly Arg Cys Val Pro Asn Tyr Tyr
            1030                    1035                    1040

CTC TGT GAT GGA GTC GAT GAT TGT CAT GAT AAC AGT GAT GAG CAA CTA      3283
Leu Cys Asp Gly Val Asp Asp Cys His Asp Asn Ser Asp Glu Gln Leu
            1045                    1050                    1055

TGT GGC ACA CTT AAT AAT ACC TGT TCA TCT TCG GCG TTC ACC TGT GGC      3331
Cys Gly Thr Leu Asn Asn Thr Cys Ser Ser Ser Ala Phe Thr Cys Gly
1060                    1065                    1070                    1075

CAT GGG GAG TGC ATT CCT GCA CAC TGG CGC TGT GAC AAA CGC AAC GAC      3379
His Gly Glu Cys Ile Pro Ala His Trp Arg Cys Asp Lys Arg Asn Asp
            1080                    1085                    1090

TGT GTG GAT GGC AGT GAT GAG CAC AAC TGC CCC ACC CAC GCA CCT GCT      3427
Cys Val Asp Gly Ser Asp Glu His Asn Cys Pro Thr His Ala Pro Ala
            1095                    1100                    1105
```

FIG. 10 cont.

```
TCC TGC CTT GAC ACC CAA TAC ACC TGT GAT AAT CAC CAG TGT ATC TCA    3475
Ser Cys Leu Asp Thr Gln Tyr Thr Cys Asp Asn His Gln Cys Ile Ser
        1110            1115            1120

AAG AAC TGG GTC TGT GAC AAT GAC ACA GAG ACA TGT GGG GAT GGA TCT GAT    3523
Lys Asn Trp Val Cys Asp Asn Asp Thr Glu Thr Cys Gly Asp Gly Ser Asp
        1125            1130            1135

GAA AAG TGC AAT TCG ACA GAG ACA TGC CAA CCT AGT CAG TTT AAT            3571
Glu Lys Cys Asn Ser Thr Glu Thr Cys Gln Pro Ser Gln Phe Asn
        1140            1145            1150            1155

TGC CCC AAT CAT CGA TGT ATT GAC CTA TCG TTT GTC TGT GAT GGT GAC        3619
Cys Pro Asn His Arg Cys Ile Asp Leu Ser Phe Val Cys Asp Gly Asp
            1160            1165            1170

AAG GAT TGT GTT GAT GGA TCT GAT GAG GTT GGT TGT GTA TTA AAC TGT       3667
Lys Asp Cys Val Asp Gly Ser Asp Glu Val Gly Cys Val Leu Asn Cys
        1175            1180            1185

ACT GCT TCT CAA TTC AAG TGT GCC AGT GGG GAT AAA TGT ATT GGC GTC       3715
Thr Ala Ser Gln Phe Lys Cys Ala Ser Gly Asp Lys Cys Ile Gly Val
        1190            1195            1200

ACA AAT CGT TGT GAT GGT GTT TTT GAT TGC AGT GAC AAC TCG GAT GAA       3763
Thr Asn Arg Cys Asp Gly Val Phe Asp Cys Ser Asp Asn Ser Asp Glu
        1205            1210            1215
```

*FIG. 10 cont.*

```
GCG GGC TGT CCA ACC AGG CCT GGT ATG TGC CAC TCA GAT GAA TTT   3811
Ala Gly Cys Pro Thr Arg Pro Gly Met Cys His Ser Asp Glu Phe
1220                1225                1230                1235

CAG TGC CAA GAA GAT GGT ATC CCG AAC TTC TGG GAA TGT GAT       3859
Gln Cys Gln Glu Asp Gly Ile Pro Asn Phe Trp Glu Cys Asp
            1240                1245                1250

GGG CAT CCA GAC TGC CTC TAT GGA TCT GAT GAG CAC AAT GCC TGT GTC  3907
Gly His Pro Asp Cys Leu Tyr Gly Ser Asp Glu His Asn Ala Cys Val
        1255                1260                1265

CCC AAG ACT TGC CCT TCA TCA TAT TTC CAC TGT GAC AAC TGC       3955
Pro Lys Thr Cys Pro Ser Ser Tyr Phe His Cys Asp Asn Cys
1270                1275                1280

ATC CAC AGG GCA TGG CTC TGT GAT CGG GAC AAT GAC TGC GGG GAT ATG  4003
Ile His Arg Ala Trp Leu Cys Asp Arg Asp Asn Asp Cys Gly Asp Met
        1285                1290                1295

AGT GAT GAG AAG GAC TGC CCT ACT CAG CCC TTT CGC TGT CCT AGT TGG  4051
Ser Asp Glu Lys Asp Cys Pro Thr Gln Pro Phe Arg Cys Pro Ser Trp
1300                1305                1310                1315

CAA TGG CAG TGT CTT GGC CAT AAC ATC TGT GTG AAT CTG AGT GTA GTG  4099
Gln Trp Gln Cys Leu Gly His Asn Ile Cys Val Asn Leu Ser Val Val
        1320                1325                1330
```

*FIG. 10 cont.*

| | | | | | | | | | | | | | | | |
|---|---|---|---|---|---|---|---|---|---|---|---|---|---|---|---|
| TGT | GAT | GGC | ATC | TTT | GAC | TGC | CCC | AAT | GGG | ACA | GAT | GAG | TCC | CCA | CTT |
| Cys | Asp | Gly | Ile | Phe | Asp | Cys | Pro | Asn | Gly | Thr | Asp | Glu | Ser | Pro | Leu |
| | | 1335 | | | | | | 1340 | | | | | 1345 | | |

4147

| TGC | AAT | GGG | AAC | AGC | TGC | TCA | GAT | TTC | AAT | GGT | GGT | TGT | ACT | CAC | GAG |
|---|---|---|---|---|---|---|---|---|---|---|---|---|---|---|---|
| Cys | Asn | Gly | Asn | Ser | Cys | Ser | Asp | Phe | Asn | Gly | Gly | Cys | Thr | His | Glu |
| | | 1350 | | | | | 1355 | | | | | 1360 | | | |

4195

| TGT | GTT | CAA | GAG | CCC | TTT | GGG | GCT | AAA | TGC | CTA | TGT | CCA | TTG | GGA | TTC |
|---|---|---|---|---|---|---|---|---|---|---|---|---|---|---|---|
| Cys | Val | Gln | Glu | Pro | Phe | Gly | Ala | Lys | Cys | Leu | Cys | Pro | Leu | Gly | Phe |
| | 1365 | | | | | 1370 | | | | | 1375 | | | | |

4243

| TTA | CTT | GCC | AAT | GAT | TCT | AAG | ACC | TGT | GAA | GAC | ATA | GAT | GAA | TGT | GAT |
|---|---|---|---|---|---|---|---|---|---|---|---|---|---|---|---|
| Leu | Leu | Ala | Asn | Asp | Ser | Lys | Thr | Cys | Glu | Asp | Ile | Asp | Glu | Cys | Asp |
| 1380 | | | | | 1385 | | | | | 1390 | | | | | 1395 |

4291

| ATT | CTA | GGC | TCT | TGT | AGC | CAG | CAC | TGT | TAC | AAT | ATG | AGA | GGT | TCT | TTC |
|---|---|---|---|---|---|---|---|---|---|---|---|---|---|---|---|
| Ile | Leu | Gly | Ser | Cys | Ser | Gln | His | Cys | Tyr | Asn | Met | Arg | Gly | Ser | Phe |
| | | | 1400 | | | | | 1405 | | | | | 1410 | | |

4339

| CGG | TGC | TCG | TGT | GAT | ACA | GGC | TAC | ATG | TTA | GAA | AGT | GAT | GGG | AGG | ACT |
|---|---|---|---|---|---|---|---|---|---|---|---|---|---|---|---|
| Arg | Cys | Ser | Cys | Asp | Thr | Gly | Tyr | Met | Leu | Glu | Ser | Asp | Gly | Arg | Thr |
| | 1415 | | | | | 1420 | | | | | 1425 | | | | |

4387

| TGC | AAA | GTT | ACA | GCA | TCT | GAG | AGT | CTG | CTG | TTA | CTT | GTG | GCA | AGT | CAG |
|---|---|---|---|---|---|---|---|---|---|---|---|---|---|---|---|
| Cys | Lys | Val | Thr | Ala | Ser | Glu | Ser | Leu | Leu | Leu | Leu | Val | Ala | Ser | Gln |
| | 1430 | | | | | 1435 | | | | | 1440 | | | | |

```
AAC AAA ATT ATT GCC GAC AGT GTC ACC TCC CAG GTC CAC AAT ATC TAT   4483
Asn Lys Ile Ile Ala Asp Ser Val Thr Ser Gln Val His Asn Ile Tyr
    1445            1450            1455

TCA TTG GTC GAG AAT GGT AGT TAC ATT GTA GCT GTT GAT TTT GAT TCA   4531
Ser Leu Val Glu Asn Gly Ser Tyr Ile Val Ala Val Asp Phe Asp Ser
1460            1465            1470            1475

ATT AGT GGT CGT ATC TTT TGG TCT GAT GCA ACT CAG GGT AAA ACC TGG   4579
Ile Ser Gly Arg Ile Phe Trp Ser Asp Ala Thr Gln Gly Lys Thr Trp
        1480            1485            1490

AGT GCG TTT CAA AAT GGA ACG GAC AGA GTG AGA TTT GAC AGT AGC       4627
Ser Ala Phe Gln Asn Gly Thr Asp Arg Val Arg Phe Asp Ser Ser
    1495            1500            1505

ATC ATC TTG ACT GAA ACT ATT GCA ATA GAT TGG GTA GGT CGT AAT CTT   4675
Ile Ile Leu Thr Glu Thr Ile Ala Ile Asp Trp Val Gly Arg Asn Leu
1510            1515            1520

TAC TGG ACA GAC TAT GCT CTG GAA ACA ATT GAA GTC AAA TCC AAA ATT GAT   4723
Tyr Trp Thr Asp Tyr Ala Leu Glu Thr Ile Glu Val Lys Ser Lys Ile Asp
        1525            1530            1535

GGG AGC CAC AGG ACT GTG CTG ATT AGT AAA AAC CTA ACA AAT CCA AGA   4771
Gly Ser His Arg Thr Val Leu Ile Ser Lys Asn Leu Thr Asn Pro Arg
1540            1545            1550            1555
```

*FIG. 10 cont.*

```
GGA CTA GCA TTA GAT CCC AGA ATG AAT GAG CAT CTA CTG TTC TGG TCT    4819
Gly Leu Ala Leu Asp Pro Arg Met Asn Glu His Leu Leu Phe Trp Ser
            1560                    1565                    1570

GAC TGG GGC CAC CCT CGC ATC GAG CGA GCC AGC ATG GAC GGC AGC        4867
Asp Trp Gly His Pro Arg Ile Glu Arg Ala Ser Met Asp Gly Ser
        1575                    1580                    1585

ATG CGC ACT GTC ATT GTC CAG GAC AAG ATC TTC TGG CCC ATG GAC TCC    4915
Met Arg Thr Val Ile Val Gln Asp Lys Ile Phe Trp Pro Met Asp
        1590                    1595                    1600

ACT ATT GAC TAC CCC AAC AGA CTG CTC TAC TTC ATG GAC TCC TAT CTT    4963
Thr Ile Asp Tyr Pro Asn Arg Leu Leu Tyr Phe Met Asp Ser Tyr Leu
            1605                    1610                    1615

GAT TAC ATG GAC TTT TGC GAT TAT AAT GGA CAC CAT CGG AGA CAG GTG    5011
Asp Tyr Met Asp Phe Cys Asp Tyr Asn Gly His His Arg Arg Gln Val
            1620                    1625                    1630                1635

ATA GCC AGT GAT TTG ATT ATA CGG CAC CCC TAT GCC CTA ACT CTC TTT    5059
Ile Ala Ser Asp Leu Ile Ile Arg His Pro Tyr Ala Leu Thr Leu Phe
            1640                    1645                    1650

GAA GAC TCT GTG TAC TGG ACT GAC GCT ACT CGT CGG GTT ATG CGA        5107
Glu Asp Ser Val Tyr Trp Thr Asp Ala Thr Arg Arg Val Met Arg
        1655                    1660                    1665
```

*FIG. 10 cont.*

```
GCC AAC AAG TGG CAT GGA GGG AAC CAG TCA GTT GTA ATG TAT AAT ATT    5155
Ala Asn Lys Trp His Gly Gly Asn Gln Ser Val Val Met Tyr Asn Ile
         1670                1675                1680

CAA TGG CCC CTT GGG ATT GTT CAT CCT TCG AAA CAA CCA AAT            5203
Gln Trp Pro Leu Gly Ile Val His Pro Ser Lys Gln Pro Asn
    1685                1690                1695

TCC GTG AAT CCA TGT GCC TTT TCC CGC TGC AGC CAT CTC TGC CTG CTT    5251
Ser Val Asn Pro Cys Ala Phe Ser Arg Cys Ser His Leu Cys Leu Leu
1700                1705                1710                1715

TCC TCA CAG GGG CCT CAT TTT TAC TCC TGT GTT TGT CCT TCA GGA TGG    5299
Ser Ser Gln Gly Pro His Phe Tyr Ser Cys Val Cys Pro Ser Gly Trp
         1720                1725                1730

AGT CTG TCT CCT GAT CTC CTG AAT TGC TTG AGA GAT GAT CAA CCT TTC    5347
Ser Leu Ser Pro Asp Leu Leu Asn Cys Leu Arg Asp Asp Gln Pro Phe
    1735                1740                1745

TTA ATA ACT GTA AGG CAA CAT ATA ATT TTT GGA ATC TCC CTT AAT CCT    5395
Leu Ile Thr Val Arg Gln His Ile Ile Phe Gly Ile Ser Leu Asn Pro
1750                1755                1760

GAG GTG AAG AGC AAT GAT GCT ATG GTC CCC ATA GCA GGG ATA CAG AAT    5443
Glu Val Lys Ser Asn Asp Ala Met Val Pro Ile Ala Gly Ile Gln Asn
         1765                1770                1775
```

FIG. 10 cont.

```
GGT TTA GAT GTT GAA TTT GAT GAT GCT GAG CAA TAC ATC TAT TGG GTT      5491
Gly Leu Asp Val Glu Phe Asp Asp Ala Glu Gln Tyr Ile Tyr Trp Val
1780                    1785                1790                1795

GAA AAT CCA GGT GAA ATT CAC AGA GTG AAG ACA GAT GGC ACC AAC AGG      5539
Glu Asn Pro Gly Glu Ile His Arg Val Lys Thr Asp Gly Thr Asn Arg
        1800                    1805                    1810

ACA GTA TTT GCT TCT ATA TCT ATG GTG GGG CCT TCT ATG AAC CTG GCC      5587
Thr Val Phe Ala Ser Ile Ser Met Val Gly Pro Ser Met Asn Leu Ala
            1815                1820                    1825

TTA GAT TGG ATT TCA AGA AAC CTT TAT TCT ACC AAT CCT AGA ACT CAG      5635
Leu Asp Trp Ile Ser Arg Asn Leu Tyr Ser Thr Asn Pro Arg Thr Gln
        1830                    1835                    1840

TCA ATC GAG GTT GTT ACA CTC CAC GGA GAT ATC AGA TAC AGA AAA ACA      5683
Ser Ile Glu Val Val Thr Leu His Gly Asp Ile Arg Tyr Arg Lys Thr
    1845                    1850                    1855

TTG ATT GCC AAT GAT GGG ACA GCT CTT GGA GTT GGC TTT CCA ATT GGC      5731
Leu Ile Ala Asn Asp Gly Thr Ala Leu Gly Val Gly Phe Pro Ily Gly
1860                    1865                    1870            1875

ATA ACT GTT GAT CCT GCT CGT GGG AAG CTG TAC TGG TCA GAC CAA GGA      5779
Ile Thr Val Asp Pro Ala Arg Gly Lys Leu Tyr Trp Ser Asp Gln Gly
            1880                    1885                    1890
```

*FIG. 10 cont.*

```
ACT GAC AGT GGG GTT CCT GCC AAG ATC GCC AGT GCT AAC ATG GAT GGC   5827
Thr Asp Ser Gly Val Pro Ala Lys Ile Ala Ser Ala Asn Met Asp Gly
        1895                    1900                1905

ACA TCT GTG AAA ACT CTC TTT ACT GGG AAC CTC GAA CAC CTG GAG TGT   5875
Thr Ser Val Lys Thr Leu Phe Thr Gly Asn Leu Glu His Leu Glu Cys
        1910                    1915                1920

GTC ACT CTT GAC ATC GAA GAG CAG AAA CTC TAC TGG GCA GTC ACT GGA   5923
Val Thr Leu Asp Ile Glu Glu Gln Lys Leu Tyr Trp Ala Val Thr Gly
        1925                    1930                1935

AGA GGA GTG ATT GAA AGA AAC GTG GAT GGA ACA GAT CGG ATG ATC       5971
Arg Gly Val Ile Glu Arg Gly Asn Val Asp Gly Thr Asp Arg Met Ile
        1940            1945                1950                1955

CTG GTA CAC CAG CTT TCC CAC CCC TGG GGA ATT GCA GTC CAT GAT TCT   6019
Leu Val His Gln Leu Ser His Pro Trp Gly Ile Ala Val His Asp Ser
        1960                    1965                1970

TTC CTT TAT TAT ACT GAT GAA CAG TAT GAG GTC ATT GAA AGA GTT GAT   6067
Phe Leu Tyr Tyr Thr Asp Glu Gln Tyr Glu Val Ile Glu Arg Val Asp
        1975                    1980                1985

AAG GCC ACT GGG GCC AAC AAA ATA GTC TTG AGA GAT AAT GTT CCA AAT   6115
Lys Ala Thr Gly Ala Asn Lys Ile Val Leu Arg Asp Asn Val Pro Asn
        1990                    1995                2000
```

FIG. 10 cont.

```
CTG AGG GGT CTT CAA GTT TAT CAC AGA CGC AAT GCC GCC GAA TCC TCA    6163
Leu Arg Gly Leu Gln Val Tyr His Arg Arg Asn Ala Ala Glu Ser Ser
    2005                    2010                    2015

AAT GGC TGT AGC AAC AAC ATG AAT GCC TGT CAG ATT TGC CTG CCT        6211
Asn Gly Cys Ser Asn Asn Met Asn Ala Cys Gln Ile Cys Leu Pro
2020                    2025                    2030            2035

GTA CCA GGA TTG TTT TCC TGC GCC TGT GCC ACT GGA TTT AAA CTC        6259
Val Pro Gly Leu Phe Ser Cys Ala Cys Ala Thr Gly Phe Lys Leu
        2040                    2045                    2050

AAT CCT GAT AAT CGG TCC TGC TCT CCA TAT AAC TCT TTC ATT GTT GTT    6307
Asn Pro Asp Asn Arg Ser Cys Ser Pro Tyr Asn Ser Phe Ile Val Val
            2055                    2060                    2065

TCA ATG CTG TCT GCA ATC AGA GGC TTT AGC TTG GAA TTG TCA GAT CAT    6355
Ser Met Leu Ser Ala Ile Arg Gly Phe Ser Leu Glu Leu Ser Asp His
        2070                    2075                    2080

TCA GAA ACC ATG GTG CCG GTG GCA GGC CAA GGA CGA AAC GCA CTG CAT    6403
Ser Glu Thr Met Val Pro Val Ala Gly Gln Gly Arg Asn Ala Leu His
            2085                    2090                    2095

GTG GAT GTG GAT GTG TCC TCT GGC TTT ATT TAT TGG TGT GAT TTT AGC    6451
Val Asp Val Asp Val Ser Ser Gly Phe Ile Tyr Trp Cys Asp Phe Ser
2100                    2105                    2110                2115
```

*FIG. 10 cont.*

```
AGC TCA GTG GCA TCT GAT AAT GCG ATC CGT AGA ATT AAA CCA GAT GGA    6499
Ser Ser Val Ala Ser Asp Asn Ala Ile Arg Arg Ile Lys Pro Asp Gly
            2120                2125                2130

TCT TCT CTG ATG AAC ATT GTG ACA CAT GGA ATA GGA GAA AAT GGA GTC    6547
Ser Ser Leu Met Asn Ile Val Thr His Gly Ile Gly Glu Asn Gly Val
            2135                2140                2145

CGG GGT ATT GCA GTG GAT TGG GTA GCA GGA AAT CTT TAT TTC ACC AAT    6595
Arg Gly Ile Ala Val Asp Trp Val Ala Gly Asn Leu Tyr Phe Thr Asn
            2150                2155                2160

GCC TTT GTT TCT GAA ACA CTG ATA GAA GTT CTG CGG ATC AAT ACT ACT    6643
Ala Phe Val Ser Glu Thr Leu Ile Glu Val Leu Arg Ile Asn Thr Thr
            2165                2170                2175

TAC CGC CGT GTT CTT CTT AAA GTC ACA GTG GAC ATG CCT AGG CAT ATT    6691
Tyr Arg Arg Val Leu Leu Lys Val Thr Val Asp Met Pro Arg His Ile
            2180                2185                2190        2195

GTT GTA GAT CCC AAG AAC AGA TAC CTC TTC TGG GCT GAC TAT GGG CAG    6739
Val Val Asp Pro Lys Asn Arg Tyr Leu Phe Trp Ala Asp Tyr Gly Gln
            2200                2205                2210

AGA CCA AAG ATT GAG CGT TCT TTC CTT GAC TGT ACC AAT CGA ACA GTG    6787
Arg Pro Lys Ile Glu Arg Ser Phe Leu Asp Cys Thr Asn Arg Thr Val
            2215                2220                2225
```

*FIG. 10 cont.*

```
CTT GTG TCA GAG GGC ATT GTC ACA CCA CGG GGC TTG GCA GTG GAC CGA    6835
Leu Val Ser Glu Gly Ile Val Thr Pro Arg Gly Leu Ala Val Asp Arg
        2230                    2235               2240

AGT GAT GGC TAC GTT TAT TGG GTT GAT GAT TCT TTA GAT ATA ATT GGA    6883
Ser Asp Gly Tyr Val Tyr Trp Val Asp Asp Ser Leu Asp Ile Ile Ala
        2245                    2250               2255

AGG ATT CGT ATC AAT GGA GAG AAC TCT GAA GTG ATT CGT TAT GGC AGT    6931
Arg Ile Arg Ile Asn Gly Glu Asn Ser Glu Val Ile Arg Tyr Gly Ser
        2260                    2265               2270           2275

CGT TAC CCA ACT CCT TAT GGC ATC ACT GTT TTT GAA AAT TCT ATC ATA    6979
Arg Tyr Pro Thr Pro Tyr Gly Ile Thr Val Phe Glu Asn Ser Ile Ile
        2280                    2285                               2290

TGG GTA GAT AGG AAT TTG AAA AAG ATC TTC CAA GCC AGC AAG GAA CCA    7027
Trp Val Asp Arg Asn Leu Lys Lys Ile Phe Gln Ala Ser Lys Glu Pro
        2295                    2300               2305

GAG AAC ACA GAG CCA CCC ACA GTG ATA AGA GAC AAT ATC AAC TGG CTA    7075
Glu Asn Thr Glu Pro Pro Thr Val Ile Arg Asp Asn Ile Asn Trp Leu
        2310                    2315               2320

AGA GAT GTG ACC ATC TTT GAC AAG CAA GTC CAG CCC CGG TCA CCA GCA    7123
Arg Asp Val Thr Ile Phe Asp Lys Gln Val Gln Pro Arg Ser Pro Ala
        2325                    2330               2335
```

*FIG. 10 cont.*

```
GAG GTC AAC AAC CCT TGC TTG GAA AAC AAT GGT GGG TGC TCT CAT      7171
Glu Val Asn Asn Pro Cys Leu Glu Asn Asn Gly Gly Cys Ser His
2340            2345            2350            2355

CTC TGC TTT GCT CTG CCT GGA TTG CAC ACC CCA AAA TGT GAC TGT GCC  7219
Leu Cys Phe Ala Leu Pro Gly Leu His Thr Pro Lys Cys Asp Cys Ala
       2360            2365            2370

TTT GGG ACC CTG CAA AGT GAT GGC AAG AAT TGT GCC ATT TCA ACA GAA  7267
Phe Gly Thr Leu Gln Ser Asp Gly Lys Asn Cys Ala Ile Ser Thr Glu
           2375            2380            2385

AAT TTC ATC TTT GCC CAT AGC TCT AAT TCC TTG AGA AGC TTA CAC TTG  7315
Asn Phe Ile Phe Ala His Ser Ser Asn Ser Leu Arg Ser Leu His Leu
       2390            2395            2400

GAC CCT GAA AAC CAT AGC CCA CCT TTC CAA ACA ATA AAT GTG GAA AGA  7363
Asp Pro Glu Asn His Ser Pro Pro Phe Gln Thr Ile Asn Val Glu Arg
2405            2410            2415

ACT GTC ATG TCT CTA GAC TAT GAC AGT GTA AGT GAT AGA ATC TAC TTC  7411
Thr Val Met Ser Leu Asp Tyr Asp Ser Val Ser Asp Arg Ile Tyr Phe
2420            2425            2430            2435

ACA CAA AAT TTA GCC TCT GGA GTT GGA CAG ATT TCC TAT GCC ACC CTG  7459
Thr Gln Asn Leu Ala Ser Gly Val Gly Gln Ile Ser Tyr Ala Thr Leu
       2440            2445            2450
```

FIG. 10 cont.

```
TCT TCA GGG ATC CAT ACT CCA ACT GTC ATT GCT TCA GGT ATA GGG ACT   7507
Ser Ser Gly Ile His Thr Pro Thr Val Ile Ala Ser Gly Ile Gly Thr
        2455                2460                2465

GCT GAT GGC ATT GCC TTT GAC TGG ATT ACT AGA AGA ATT TAT TAC AGT   7555
Ala Asp Gly Ile Ala Phe Asp Trp Ile Thr Arg Arg Ile Tyr Tyr Ser
        2470                2475                2480

GAC TAC CTC AAC CAG ATG ATT AAT TCC ATG GCT GAA GAT GGG TCT AAC   7603
Asp Tyr Leu Asn Gln Met Ile Asn Ser Met Ala Glu Asp Gly Ser Asn
        2485                2490                2495

CGC ACT GTG ATA GCC CGC GTT CCA AAA CCA AGA GCA ATT GTG TTA GAT   7651
Arg Thr Val Ile Ala Arg Val Pro Lys Pro Arg Ala Ile Val Leu Asp
        2500                2505                2510          2515

CCC TGC CAA GGG TAC CTG TAC TGG GCT GAC TGG GAT ACA CAT GCC AAA   7699
Pro Cys Gln Gly Tyr Leu Tyr Trp Ala Asp Trp Asp Thr His Ala Lys
        2520                2525                2530

ATC GAG AGA GCC ACA TTG GGA GGA AAC TTC CGG GTA CCC ATT GTG AAC   7747
Ile Glu Arg Ala Thr Leu Gly Gly Asn Phe Arg Val Pro Ile Val Asn
        2535                2540                2545

AGC AGT CTG GTC ATG CCC AGT GGG CTG ACT CTG GAC TAT GAA GAG GAC   7795
Ser Ser Leu Val Met Pro Ser Gly Leu Thr Leu Asp Tyr Glu Glu Asp
        2550                2555                2560
```

FIG. 10 cont.

```
CTT CTC TAC TGG GTG GAT GCT AGT CTG CAG AGG ATT GAA CGC AGC ACT   7843
Leu Leu Tyr Trp Val Asp Ala Ser Leu Gln Arg Ile Glu Arg Ser Thr
    2565                2570                2575

CTG ACG GGC GTG GAT CGT GAA GTC AAT GTC GCC GTT CAT GCT           7891
Leu Thr Gly Val Asp Arg Glu Val Asn Val Ala Val His Ala
    2580                2585                2590            2595

TTT GGC TTC ACT CTC TAT GGC CAG TAT ATT TGG ACT GAC TTG TAC       7939
Phe Gly Phe Thr Leu Tyr Gly Gln Tyr Ile Tyr Trp Thr Asp Leu Tyr
            2600                2605                2610

ACA CAA AGA ATT TAC CGA GCT AAC AAA TAT GAC GGG TCA GGT CAG ATT   7987
Thr Gln Arg Ile Tyr Arg Ala Asn Lys Tyr Asp Gly Ser Gly Gln Ile
        2615                2620                2625

GCA ATG ACC ACA AAT TTG CTC TCC CAG CCC AGG GGA ATC AAC ACT GTT   8035
Ala Met Thr Thr Asn Leu Leu Ser Gln Pro Arg Gly Ile Asn Thr Val
    2630                2635                2640

GTG AAG AAC CAG AAA CAA CAG TGT AAC CCT TGT GAA CAG TTT AAT       8083
Val Lys Asn Gln Lys Gln Gln Cys Asn Pro Cys Glu Gln Phe Asn
    2645                2650                2655

GGG GGC TGC AGC CAT ATC TGT GCA CCA GGT CCA AAT GGT GCC GAG TGC   8131
Gly Gly Cys Ser His Ile Cys Ala Pro Gly Pro Asn Gly Ala Glu Cys
    2660                2665                2670            2675
```

FIG. 10 cont.

```
CAG TGT CCA CAT GAG GGC AAC TGG TAT TTG GCC AAC AAC AGG AAG CAC          8179
Gln Cys Pro His Glu Gly Asn Trp Tyr Leu Ala Asn Asn Arg Lys His
        2680                          2685                  2690

TGC ATT GTG GAC AAT GGT GAA CGA TGT GGT GCA TCT TCC TTC ACC TGC          8227
Cys Ile Val Asp Asn Gly Glu Arg Cys Gly Ala Ser Ser Phe Thr Cys
        2695                          2700                 2705

TCC AAT GGG CGC TGC ATC TCG GAA GAG TGG AAG TGT GAT AAT GAC AAC          8275
Ser Asn Gly Arg Cys Ile Ser Glu Glu Trp Lys Cys Asp Asn Asp Asn
        2710                          2715                 2720

GAC TGT GGG GAT GGC AGT GAT GAG ATG GAA AGT GTC TGT GCA CTT CAC          8323
Asp Cys Gly Asp Gly Ser Asp Glu Met Glu Ser Val Cys Ala Leu His
        2725                          2730                 2735

ACC TGC TCA CCG ACA GCC TTC ACC TGT GCC AAT GGG CGA TGT GTC CAA          8371
Thr Cys Ser Pro Thr Ala Phe Thr Cys Ala Asn Gly Arg Cys Val Gln
        2740                          2745                 2750                 2755

TAC TCT TCA CGC TGT GAT TAC AAT GAC TGT GGT GAT GGC AGT GAT          8419
Tyr Ser Ser Arg Cys Asp Tyr Asn Asp Cys Gly Asp Gly Ser Asp
        2760                          2765                 2770

GAG GCA GGG TGC CTG TTC AGG GAC TGC AAT GCC ACC ACG GAG TTT ATG          8467
Glu Ala Gly Cys Leu Phe Arg Asp Cys Asn Ala Thr Thr Glu Phe Met
        2775                          2780                 2785
```

*FIG. 10 cont.*

| | | | | | | | | | | | | | | | | |
|---|---|---|---|---|---|---|---|---|---|---|---|---|---|---|---|---|
| TGC | AAT | AAC | AGA | AGG | TGC | ATA | CCT | CGT | GAG | TTT | ATC | TGC | AAT | GGT | GTA | 8515 |
| Cys | Asn | Asn | Arg | Arg | Cys | Ile | Pro | Arg | Glu | Phe | Ile | Cys | Asn | Gly | Val | |
| | | 2790 | | | | | 2795 | | | | | 2800 | | | | |
| GAC | AAC | TGC | CAT | GAT | AAT | AAC | ACT | TCA | GAT | GAG | AAA | AAT | TCA | CCT | GAT | 8563 |
| Asp | Asn | Cys | His | Asp | Asn | Asn | Thr | Ser | Asp | Glu | Lys | Asn | Ser | Pro | Asp | |
| | 2805 | | | | | 2810 | | | | | 2815 | | | | | |
| CGC | ACT | TGC | CAG | TCT | GGA | TAC | ACA | AAA | TGT | CAT | AAT | TCA | AAT | ATT | TGT | 8611 |
| Arg | Thr | Cys | Gln | Ser | Gly | Tyr | Thr | Lys | Cys | His | Asn | Ser | Asn | Ile | Cys | |
| 2820 | | | | | 2825 | | | | | 2830 | | | | | 2835 | |
| ATT | CCT | CGC | GTT | TAT | TTG | TGT | GAC | GGA | GAC | AAT | GAC | TGT | GGA | GAT | AAC | 8659 |
| Ile | Pro | Arg | Val | Tyr | Leu | Cys | Asp | Gly | Asp | Asn | Asp | Cys | Gly | Asp | Asn | |
| | | 2840 | | | | | 2845 | | | | | 2850 | | | | |
| AGT | GAT | GAA | AAC | CCT | GTT | TAT | TGC | ACC | ACT | CAC | ACA | TGC | AGC | AGT | 8707 |
| Ser | Asp | Glu | Asn | Pro | Val | Tyr | Cys | Thr | Thr | His | Thr | Cys | Ser | Ser | Ser | |
| | | 2855 | | | | | 2860 | | | | | 2865 | | | | |
| GAG | TTC | CAA | TGC | GCA | TCT | GGG | CGC | TGT | ATT | CCT | CAA | CAT | TGG | TAT | TGT | 8755 |
| Glu | Phe | Gln | Cys | Ala | Ser | Gly | Arg | Cys | Ile | Pro | Gln | His | Trp | Tyr | Cys | |
| | 2870 | | | | | 2875 | | | | | 2880 | | | | | |
| GAT | CAA | GAA | ACA | GAT | TGT | TTT | GAT | GCC | TCT | GAT | GAA | CCT | GCC | TCT | TGT | 8803 |
| Asp | Gln | Glu | Thr | Asp | Cys | Phe | Asp | Ala | Ser | Asp | Glu | Pro | Ala | Ser | Cys | |
| 2885 | | | | | 2890 | | | | | 2895 | | | | | | |

FIG. 10 cont.

```
GGT CAC TCT GAG CGA ACA TGC CTA GCT GAT GAG TTC AAG TGT GAT GGT      8851
Gly His Ser Glu Arg Thr Cys Leu Ala Asp Glu Phe Lys Cys Asp Gly
2900                    2905                2910                2915

GGG AGG TGC ATC CCA AGC GAA TGG ATC TGT GAC GGT GAT AAT GAC TGT      8899
Gly Arg Cys Ile Pro Ser Glu Trp Ile Cys Asp Gly Asp Asn Asp Cys
              2920                2925                    2930

GAT ATG AGT GAC GAG GAT AAA AGG CAC CAG TGT CAG AAT CAA AAC          8947
Gly Asp Met Ser Asp Glu Asp Lys Arg His Gln Cys Gln Asn Gln Asn
         2935                2940                    2945

TGC TCG GAT TCC GAG TTT CTC TGT GTA AAT GAC AGA CCT CCG GAC AGG      8995
Cys Ser Asp Ser Glu Phe Leu Cys Val Asn Asp Arg Pro Pro Asp Arg
         2950                2955                        2960

AGG TGC ATT CCC CAG TCT TGG GTC TGT GAT GGC GAT GTG GAT TGT ACT      9043
Arg Cys Ile Pro Gln Ser Trp Val Cys Asp Gly Asp Val Asp Cys Thr
    2965                    2970                    2975

GAC GGC TAC GAT GAG GAG AAT TGC CAG AAT GAG GAT GGC ACC AGG AGA ACT TGC TCT GAA      9091
Asp Gly Tyr Asp Glu Glu Asn Cys Gln Asn Glu Asp Gly Thr Arg Arg Thr Cys Ser Glu
2980                            2985                    2990                2995

AAT GAA TTC ACC TGT GGT TAC GGA CTG TGT ATC CCA AAG ATA TTC AGG      9139
Asn Glu Phe Thr Cys Gly Tyr Gly Leu Cys Ile Pro Lys Ile Phe Arg
         3000                    3005                        3010
```

*FIG. 10 cont.*

| | | | | | | | | | | | | | | | |
|---|---|---|---|---|---|---|---|---|---|---|---|---|---|---|---|
| TGT | GAC | CGG | CAC | AAT | GAC | TGT | GGT | GAC | TAT | AGC | GAC | GAG | AGG | GGC | TGC |
| Cys | Asp | Arg | His | Asn | Asp | Cys | Gly | Asp | Tyr | Ser | Asp | Glu | Arg | Gly | Cys |
| | | | 3015 | | | | | 3020 | | | | | 3025 | | 9187 |
| TTA | TAC | CAG | ACT | TGC | CAA | CAG | AAT | CAG | TTT | ACC | TGT | CAG | AAC | GGG | CGC |
| Leu | Tyr | Gln | Thr | Cys | Gln | Gln | Asn | Gln | Phe | Thr | Cys | Gln | Asn | Gly | Arg |
| | | 3030 | | | | | 3035 | | | | | 3040 | | | 9235 |

| | | | | | | | | | | | | | | | |
|---|---|---|---|---|---|---|---|---|---|---|---|---|---|---|---|
| TGC | ATT | AGT | AAA | ACC | TTC | GTC | TGT | GAT | GAG | GAT | AAT | GAC | TGT | GGA | GAC |
| Cys | Ile | Ser | Lys | Thr | Phe | Val | Cys | Asp | Glu | Asp | Asn | Asp | Cys | Gly | Asp |
| | 3045 | | | | | 3050 | | | | | 3055 | | | | 9283 |
| GGA | TCT | GAT | GAG | CTG | ATG | CAC | CTG | TGC | CAC | ACC | CCA | GAA | CCC | ACG | TGT |
| Gly | Ser | Asp | Glu | Leu | Met | His | Leu | Cys | His | Thr | Pro | Glu | Pro | Thr | Cys |
| 3060 | | | | | 3065 | | | | | 3070 | | | | | 3075 9331 |

| | | | | | | | | | | | | | | | |
|---|---|---|---|---|---|---|---|---|---|---|---|---|---|---|---|
| CCA | CCT | CAC | GAG | TTC | AAG | TGT | GAC | AAT | GGG | CGC | TGC | ATC | GAG | ATG | ATG |
| Pro | Pro | His | Glu | Phe | Lys | Cys | Asp | Asn | Gly | Arg | Cys | Ile | Glu | Met | Met |
| | | | 3080 | | | | | 3085 | | | | | 3090 | | 9379 |
| AAA | CTC | TGC | AAC | CAC | CTA | GAT | GAC | TGT | TTG | GAC | AAC | AGC | GAT | GAG | AAA |
| Lys | Leu | Cys | Asn | His | Leu | Asp | Asp | Cys | Leu | Asp | Asn | Ser | Asp | Glu | Lys |
| | | 3095 | | | | | 3100 | | | | | 3105 | | | 9427 |

| | | | | | | | | | | | | | | | |
|---|---|---|---|---|---|---|---|---|---|---|---|---|---|---|---|
| GGC | TGT | GGC | ATT | AAT | GAA | TGC | CAT | GAC | CCT | TCA | ATC | AGT | GGC | TGC | GAT |
| Gly | Cys | Gly | Ile | Asn | Glu | Cys | His | Asp | Pro | Ser | Ile | Ser | Gly | Cys | Asp |
| | 3110 | | | | | 3115 | | | | | 3120 | | | | 9475 |

FIG. 10 cont.

```
CAC AAC TGC ACA GAC ACC TTA ACC AGT TTC TAT TGT TCC TGT CGT CCT    9523
His Asn Cys Thr Asp Thr Leu Thr Ser Phe Tyr Cys Ser Cys Arg Pro
3125                    3130                3135

GGT TAC AAG CTC ATG TCT GAC AAG CGG ACT TGT GTT GAT ATT GAT GAA    9571
Gly Tyr Lys Leu Met Ser Asp Lys Arg Thr Cys Val Asp Ile Asp Glu
3140                    3145                3150            3155

TGC ACA GAG ATG CCT TTT GTC TGT AGC CAG AAG TGT GAG AAT GTA ATA    9619
Cys Thr Glu Met Pro Phe Val Cys Ser Gln Lys Cys Glu Asn Val Ile
        3160                    3165                    3170

GGC TCC TAC ATC TGT AAG TGT GCC CCA GGC TAC CTC CGA GAA CCA GAT    9667
Gly Ser Tyr Ile Cys Lys Cys Ala Pro Gly Tyr Leu Arg Glu Pro Asp
3175                    3180                    3185

GGA AAG ACC TGC CGG CAA AAC AGT AAC ATC GAA CCC TAT CTC ATT TTT    9715
Gly Lys Thr Cys Arg Gln Asn Ser Asn Ile Glu Pro Tyr Leu Ile Phe
        3190                    3195                3200

AGC AAC CGT TAC TAT TTG AGA AAT TTA ACT ATA GAT GGC TAT TTT TAC    9763
Ser Asn Arg Tyr Tyr Leu Arg Asn Leu Thr Ile Asp Gly Tyr Phe Tyr
3205                    3210                    3215

TCC CTC ATC TTG GAA GGA CTG GAC AAT GTT GTG GAC TTA GAT TTT GAC    9811
Ser Leu Ile Leu Glu Gly Leu Asp Asn Val Val Asp Leu Asp Phe Asp
        3220                3225                3230        3235
```

FIG. 10 cont.

```
CGA GTA GAG AAG AGA TTG TAT TGG ATT GAT ACA CAG AGG CAA GTC ATT      9859
Arg Val Glu Lys Arg Leu Tyr Trp Ile Asp Thr Gln Arg Gln Val Ile
3240                    3245                    3250

GAG AGA ATG TTT CTG AAT AAG ACA AAC AAG GAG ACA ATC ATA AAC CAC      9907
Glu Arg Met Phe Leu Asn Lys Thr Asn Lys Glu Thr Ile Ile Asn His
        3255                    3260                    3265

AGA CTA CCA GCT GCA GAA AGT CTG GCT GTA GAC TGG GTT TCC AGA AAG      9955
Arg Leu Pro Ala Ala Glu Ser Leu Ala Val Asp Trp Val Ser Arg Lys
3270                    3275                    3280

CTC TAC TTG GAT GCC CGC CGC ATG CTG GCC CAG CAC TGT GTC TCT GAC CTC  10003
Leu Tyr Trp Leu Asp Ala Arg Arg Met Leu Ala Gln His Cys Val Ser Asp Leu
        3285                    3290                    3295            3310

AAT GGT GGA CAC CGC CGC ATG CTG GCC CAG CAC TGT GTC TCT GAC CTC      10003
Asn Gly Gly His Arg Arg Met Leu Ala Gln His Cys Val Ser Asp Leu
3300                    3305                    3310
```



```
CGA GTA GAG AAG AGA TTG TAT TGG ATT GAT ACA CAG AGG CAA GTC ATT      9859
Arg Val Glu Lys Arg Leu Tyr Trp Ile Asp Thr Gln Arg Gln Val Ile
3240                    3245                    3250

GAG AGA ATG TTT CTG AAT AAG ACA AAC AAG GAG ACA ATC ATA AAC CAC      9907
Glu Arg Met Phe Leu Asn Lys Thr Asn Lys Glu Thr Ile Ile Asn His
        3255                    3260                    3265

AGA CTA CCA GCT GCA GAA AGT CTG GCT GTA GAC TGG GTT TCC AGA AAG      9955
Arg Leu Pro Ala Ala Glu Ser Leu Ala Val Asp Trp Val Ser Arg Lys
3270                    3275                    3280

CTC TAC TTG GAT GCC CGC CGC ATG CTG GCC CAG CAC TTT GTC TCT GAC CTC  10003
Leu Tyr Trp Leu Asp Ala Arg Arg Met Leu Ala Gln His Phe Val Ser Asp Leu
        3285                    3290                    3295

AAT GGT GGA CAC CGC CGC ATG CTG GCC CAG CAC TGT GTG GAT GCC AAC      10051
Asn Gly Gly His Arg Arg Met Leu Ala Gln His Cys Val Asp Ala Asn
3300                    3305                    3310            3315

AAC ACC TTC TGC TTT GAT AAT CCC AGA GGA CTT GCC CTT CAC CCT CAA      10099
Asn Thr Phe Cys Phe Asp Asn Pro Arg Gly Leu Ala Leu His Pro Gln
        3320                    3325                    3330

TAT GGG TAC CTC TAC TGG GCA GAC TGG GGT CAC CGC GCA TAC ATT GGG      10147
Tyr Gly Tyr Leu Tyr Trp Ala Asp Trp Gly His Arg Ala Tyr Ile Gly
3335                    3340                    3345
```

FIG. 10 cont.

```
AGA GTA GGC ATG GAT GGA ACC AAC AAG TCT GTG ATA ATC TCC ACC AAG      10195
Arg Val Gly Met Asp Gly Thr Asn Lys Ser Val Ile Ile Ser Thr Lys
         3350                3355                3360

TTA GAG TGG CCT AAT GGC ATC ACC ATT GAT TAC ACC ATT GAT CTA CTC      10243
Leu Glu Trp Pro Asn Gly Ile Thr Ile Asp Tyr Thr Ile Asp Leu Leu
         3365                3370                3375

TAC TGG GCA GAT GCC CAC CTG GGT TAC ATA GAG TAC TCT GAT TTG GAG      10291
Tyr Trp Ala Asp Ala His Leu Gly Tyr Ile Glu Tyr Ser Asp Leu Glu
         3380                3385                3390        3395

GGC CAC CAT CGA CAC ACG GTG TAT GAT GGG GCA CTG CCT CAC CCT TTC      10339
Gly His His Arg His Thr Val Tyr Asp Gly Ala Leu Pro His Pro Phe
         3395                3400                3405        3410

GCT ATT ACC ATT TTT GAA GAC ACT ATT TAT TGG ACA GAT TGG AAT ACA      10387
Ala Ile Thr Ile Phe Glu Asp Thr Ile Tyr Trp Thr Asp Trp Asn Thr
         3415                3420                3425

AGG ACA GTG GAA AAG GGA TCA GAT TAT AAA AAG AAC GGA TCA AAT AGA CAG ACA  10435
Arg Thr Val Glu Lys Gly Ser Asp Tyr Lys Lys Asn Gly Ser Asn Arg Gln Thr
         3430                3435                3440

CTG GTG AAC ACA ACA CAC AGA CCA TTT GAC ATC CAT GTG TAC CAT CCA      10483
Leu Val Asn Thr Thr His Arg Pro Phe Asp Ile His Val Tyr His Pro
         3445                3450                3455
```

FIG. 10 cont.

```
TAT AGG CAG CCC ATT GTG AGC AAT CCC TGT GGT ACC AAC AAT GGT GGC      10531
Tyr Arg Gln Pro Ile Val Ser Asn Pro Cys Gly Thr Asn Asn Gly Gly
3460            3465            3470            3475

TGT TCT CAT CTC TGC CTC ATC AAG CCA GGA GGA AAA GGG TTC ACT TGC      10579
Cys Ser His Leu Cys Leu Ile Lys Pro Gly Gly Lys Gly Phe Thr Cys
       3480            3485            3490

GAG TGT CCA GAT GAC TTC CGC ACC CTT CAA CTG AGT GGC AGC ACC TAC      10627
Glu Cys Pro Asp Asp Phe Arg Thr Leu Gln Leu Ser Gly Ser Thr Tyr
3495            3500            3505

TGC ATG CCC ATG TGC TCC AGC ACC CAG TTC CTG TGC GCT AAC AAT GAA      10675
Cys Met Pro Met Cys Ser Ser Thr Gln Phe Leu Cys Ala Asn Asn Glu
       3510            3515            3520

AAG TGC ATT CCT ATC TGG TGG AAA TGT GAT GGA CAG AAA GAC TGC TCA      10723
Lys Cys Ile Pro Ile Trp Trp Lys Cys Asp Gly Gln Lys Asp Cys Ser
3525            3530            3535

GAT GGC TCT GAT GAA CTG GCC CTT TGC CCG CAG CGC TTC TGC CGA CTG      10771
Asp Gly Ser Asp Glu Leu Ala Leu Cys Pro Gln Arg Phe Cys Arg Leu
       3540            3545            3550            3555

GGA CAG TTC CAG AGT GAC GGC AAC TGC ACC AGC CCG CAG ACT TTA          10819
Gly Gln Phe Gln Ser Asp Gly Asn Cys Thr Ser Pro Gln Thr Leu
3560            3565            3570
```

*FIG. 10 cont.*

```
TGC AAT GCT CAC CAA AAT TGC CCT GAT GGG TCT GAT GAA GAC CGT CTT    10867
Cys Asn Ala His Gln Asn Cys Pro Asp Gly Ser Asp Glu Asp Arg Leu
             3575                3580                3585

CTT TGT GAG AAT CAC CAC TGT CAC TCC AAT GAA TGG CAG TGC GCC AAC    10915
Leu Cys Glu Asn His His Cys His Ser Asn Glu Trp Gln Cys Ala Asn
             3590                3595                3600

AAA CGT TGC ATC CCA GAA TCC ATC TGG CAG TGT GAC ACA TTT AAC GAC TGT    10963
Lys Arg Cys Ile Pro Glu Ser Ile Trp Gln Cys Asp Thr Phe Asn Asp Cys
             3605                3610                3615

GAG GAT AAC TCA GAT GAA GAC GAG AGT TCC CAC TGT CYS AGC AGG ACC TGC    11011
Glu Asp Asn Ser Asp Glu Asp Glu Ser Ser His Cys Cys Ala Ser Arg Thr Cys
             3620                3625                3630                3635

CGG CCG GGC CAG TTT CGG TGT GCT AAT GGC CGC TGC ATC CCG CAG GCC    11059
Arg Pro Gly Gln Phe Arg Cys Ala Asn Gly Arg Cys Ile Pro Gln Ala
             3640                3645                3650

TGG AAG TGT GAT GTG GAT GAT GAT TGT GGA GAC CAC TCG GAT GAG CCC    11107
Trp Lys Cys Asp Val Asp Asp Asp Cys Gly Asp His Ser Asp Glu Pro
             3655                3660                3665

ATT GAA GAA TGC AGC ATG AGC TCT GCC CAT CTC TGT GAC AAC TTC ACA GAA    11155
Ile Glu Glu Cys Ser Met Ser Ser Ala His Leu Cys Asp Asn Phe Thr Glu
             3670                3675                3680
```

*FIG. 10 cont.*

| | | | | | | | | | | | | | | | |
|---|---|---|---|---|---|---|---|---|---|---|---|---|---|---|---|
| TTC | AGC | TGC | AAA | ACA | AAT | TAC | CGC | TGC | ATC | CCA | AAG | TGG | GCC | GTG | TGC |
| Phe | Ser | Cys | Lys | Thr | Asn | Tyr | Arg | Cys | Ile | Pro | Lys | Trp | Ala | Val | Cys |
| | 3685 | | | | | 3690 | | | | | 3695 | | | | |

11203

| | | | | | | | | | | | | | | | |
|---|---|---|---|---|---|---|---|---|---|---|---|---|---|---|---|
| AAT | GGT | GTA | GAT | GAC | TGC | AGG | TGC | AGT | GAT | TTC | GAG | CAA | GGC | TGT | GAG |
| Asn | Gly | Val | Asp | Asp | Cys | Arg | Cys | Ser | Asp | Phe | Glu | Gln | Gly | Cys | Glu |
| 3700 | | | | | 3705 | | | | | 3710 | | | | | 3715 |

11251

| | | | | | | | | | | | | | | | |
|---|---|---|---|---|---|---|---|---|---|---|---|---|---|---|---|
| GAG | AGG | ACA | TGC | CAT | CCT | GTG | GGG | GAT | TTC | CGC | TGT | AAA | AAT | CAC | CAC |
| Glu | Arg | Thr | Cys | His | Pro | Val | Gly | Asp | Phe | Arg | Cys | Lys | Asn | His | His |
| | | | 3720 | | | | 3725 | | | | | 3730 | | | |

11299

| | | | | | | | | | | | | | | | |
|---|---|---|---|---|---|---|---|---|---|---|---|---|---|---|---|
| TGC | ATC | CCT | CTT | CGT | TGG | CAG | TGT | GAT | GGG | CAA | AAT | GAC | TGT | GGA | GAT |
| Cys | Ile | Pro | Leu | Arg | Trp | Gln | Cys | Asp | Gly | Gln | Asn | Asp | Cys | Gly | Asp |
| | 3735 | | | | | 3740 | | | | | 3745 | | | | |

11347

| | | | | | | | | | | | | | | | |
|---|---|---|---|---|---|---|---|---|---|---|---|---|---|---|---|
| AAC | TCA | GAT | GAG | GAA | AAC | TGT | GCT | CCC | CGG | GAG | TGC | ACA | GAG | AGC | GAG |
| Asn | Ser | Asp | Glu | Glu | Asn | Cys | Ala | Pro | Arg | Glu | Cys | Thr | Glu | Ser | Glu |
| | | 3750 | | | | 3755 | | | | | 3760 | | | | |

11395

| | | | | | | | | | | | | | | | |
|---|---|---|---|---|---|---|---|---|---|---|---|---|---|---|---|
| TTT | CGA | TGT | GTC | AAT | CAG | CAG | TGC | ATT | CCC | TCG | CGA | TGG | ATC | TGT | GAC |
| Phe | Arg | Cys | Val | Asn | Gln | Gln | Cys | Ile | Pro | Ser | Arg | Trp | Ile | Cys | Asp |
| 3765 | | | | | 3770 | | | | | 3775 | | | | | |

11443

| | | | | | | | | | | | | | | | |
|---|---|---|---|---|---|---|---|---|---|---|---|---|---|---|---|
| CAT | TAC | AAC | GAC | TGT | GGG | GAC | AAC | TCA | GAT | GAA | CGG | GAC | TGT | GAG | ATG |
| His | Tyr | Asn | Asp | Cys | Gly | Asp | Asn | Ser | Asp | Glu | Arg | Asp | Cys | Glu | Met |
| 3780 | | | | | 3785 | | | | | 3790 | | | | | 3795 |

```
AGG ACC TGC CAT CCT GAA TAT TTT CAG TGT ACA AGT GGA CAT TGT GTA        11539
Arg Thr Cys His Pro Glu Tyr Phe Gln Cys Thr Ser Gly His Cys Val
                3800                3805                3810

CAC AGT GAA CTG AAA TGC GAT GGA TCC GCT GAC TGT TTG GAT GCG TCT        11587
His Ser Glu Leu Lys Cys Asp Gly Ser Ala Asp Cys Leu Asp Ala Ser
            3815                3820                3825

GAT GAA GCT GCA GAT TGT CCC TTT CCT GAT GGT GCA TAC TGC CAG            11635
Asp Glu Ala Ala Asp Cys Pro Phe Pro Asp Gly Ala Tyr Cys Gln
            3830                3835                3840

GCT ACT ATG TTC GAA TGC AAA CAT GTT TGT ATC CCG CCA TAT TGG            11683
Ala Thr Met Phe Glu Cys Lys His Val Cys Ile Pro Pro Tyr Trp
3845                3850                3855

AAA TGT GAT GGC GAT GAT GAC TGT GGT GAT GGT TCA GAT GAA GAA CTT        11731
Lys Cys Asp Gly Asp Asp Asp Cys Gly Asp Gly Ser Asp Glu Glu Leu
3860                3865            3870                3875

CAC CTG TGC TTG GAT TTG GAT CCC TGT AAT TCA CCA AAC CGT TTC CGG TGT    11779
His Leu Cys Leu Asp Leu Asp Pro Cys Asn Ser Pro Asn Arg Phe Arg Cys
                    3880                3885                3890

GAC AAT AAT CGC TGC ATT TAT AGT CAT GAG GTG TGC AAT GGT GTG GAT        11827
Asp Asn Asn Arg Cys Ile Tyr Ser His Glu Val Cys Asn Gly Val Asp
                3895                3900                3905
```

FIG. 10 cont.

```
GAC TGT GGA GAT GGA ACT GAT GAG ACA GAG GAG CAC TGT AGA AAA CCG    11875
Asp Cys Gly Asp Gly Thr Asp Glu Thr Glu Glu His Cys Arg Lys Pro
        3910                3915                3920

ACC CCT AAA CCT TGT ACA GAA TAT GAA TAT AAG TGT GGC AAT GGG CAT    11923
Thr Pro Lys Pro Cys Thr Glu Thr Glu Tyr Lys Cys Gly Asn Gly His
    3925                3930                3935

TGC ATT CCA CAT GAC AAT GTG TGT GAT GAT GCC GAT GAC TGT GGT GAC    11971
Cys Ile Pro His Asp Asn Val Cys Asp Asp Ala Asp Asp Cys Gly Asp
3940                3945                3950                3955

TGG TCC GAT GAA CTG GGT TGC AAT AAA GGA AAA GAA AGA ACA TGT GCT    12019
Trp Ser Asp Glu Leu Gly Cys Asn Lys Gly Lys Glu Arg Thr Cys Ala
                3960                3965                3970

GAA AAT ATA TGC GAG CAA AAT TGT ACC CAA TTA AAT GAA GGA GGA TTT    12067
Glu Asn Ile Cys Glu Gln Asn Cys Thr Gln Leu Asn Glu Gly Gly Phe
            3975                3980                3985

ATC TGC TCC TGT ACA GAT GGG TTC GAA ACC AAT GTT TTT GAC AGA ACC    12115
Ile Cys Ser Cys Thr Ala Gly Phe Glu Thr Asn Val Phe Asp Arg Thr
        3990                3995                4000

TCC TGT CTA GAT ATC AAT GAA TGT GAA CAA TTT GGG ACT TGT CCC CAG    12163
Ser Cys Leu Asp Ile Asn Glu Cys Glu Gln Phe Gly Thr Cys Pro Gln
    4005                4010                4015
```

FIG. 10 cont.

```
CAC TGC AGA AAT ACC AAA GGA AGT TAT GAG TGT GTC TGT GCT GAT GGC   12211
His Cys Arg Asn Thr Lys Gly Ser Tyr Glu Cys Val Cys Ala Asp Gly
4020            4025            4030            4035

TTC ACG TCT ATG AGT GAC CGC CCT GGA AAA TGT GCA GCT GAG GGT       12259
Phe Thr Ser Met Ser Asp Arg Pro Gly Lys Cys Ala Ala Glu Gly
         4040            4045            4050

AGC TCT CCT TTG CTA CTG CCT GAC AAT GTC CGA ATT CGA AAA TAT       12307
Ser Ser Pro Leu Leu Leu Pro Asp Asn Val Arg Ile Arg Lys Tyr
4055            4060            4065

AAT CTC TCA TCT GAG AGG TTC TCA GAG TAT CTT CAA GAT GAG GAA TAT   12355
Asn Leu Ser Ser Glu Arg Phe Ser Glu Tyr Leu Gln Asp Glu Glu Tyr
         4070            4075            4080

ATC CAA GCT GTT GAT TAT TGG GAT TGG GAT CCC AAG GAC ATA GGC CTC AGT   12403
Ile Gln Ala Val Asp Tyr Trp Asp Pro Lys Asp Ile Gly Leu Ser
4085            4090            4095

GTT GTG TAT TAC ACT GTG CGA GGG GAG GGC TCT AGG TTT GGT GCT ATC   12451
Val Val Tyr Tyr Thr Val Arg Gly Glu Gly Ser Arg Phe Gly Ala Ile
4100            4105            4110            4115

AAA CGT GCC TAC ATC CCC AAC TTT GAA TCC GGC CGC AAT AAT CTT GTG   12499
Lys Arg Ala Tyr Ile Pro Asn Phe Glu Ser Gly Arg Asn Asn Leu Val
         4120            4125            4130
```

FIG. 10 cont.

```
CAG GAA GTT GAC CTG AAA TAC GTA ATG CAG CCA GAT GGA ATA    12547
Gln Glu Val Asp Leu Lys Tyr Val Met Gln Pro Asp Gly Ile
            4135                4140                4145

GCA GTG GAC TGG GTT GGA AGG CAT ATT TAC TGG TCA GAT GTC AAG AAT    12595
Ala Val Asp Trp Val Gly Arg His Ile Tyr Trp Ser Asp Val Lys Asn
            4150                4155                4160

AAA CGC ATT GAG GTG GCT AAA CTT GAT GGA AGG TAC AGA AAG TGG CTG    12643
Lys Arg Ile Glu Val Ala Lys Leu Asp Gly Arg Tyr Arg Lys Trp Leu
            4165                4170                4175

ATT TCC ACT GAC CTG GAC CAA CCA GCT ATT GCT GTG AAT CCC AAA    12691
Ile Ser Thr Asp Leu Asp Gln Pro Ala Ile Ala Val Asn Pro Lys
            4180                4185                4190    4195

CTA GGG CTT ATG TTC TGG ACT GAC TGG GGA AAG GAA CCT AAA ATC GAG    12739
Leu Gly Leu Met Phe Trp Thr Asp Trp Gly Lys Glu Pro Lys Ile Glu
            4200                4205                4210

TCT GCC TGG ATG AAT GGA GAG GAC CGC AAC ATC CTG GTT TTC GAG GAC    12787
Ser Ala Trp Met Asn Gly Glu Asp Arg Asn Ile Leu Val Phe Glu Asp
            4215                4220                4225

CTT GGT TGG CCA ACT GGC CTT TCT ATC GAT TAT TTG AAC GAC CGA ATC    12835
Leu Gly Trp Pro Thr Gly Leu Ser Ile Asp Tyr Leu Asn Asp Arg Ile
            4230                4235                4240
```

*FIG. 10 cont.*

```
TAC TGG AGT GAC TTC AAG GAG GAC GTT ATT GAA ACC ATA AAA TAT GAT    12883
Tyr Trp Ser Asp Phe Lys Glu Asp Val Ile Glu Thr Ile Lys Tyr Asp
4245                                         4255

GGG ACT GAT AGG GTC ATT GCA ATT GCA ATG AAC CCT TAC AGC            12931
Gly Thr Asp Arg Val Ile Ala Ile Ala Met Asn Pro Tyr Ser
4260            4265             4270             4275

CTG GAC ATC TTT GAA GAC CAG TTA TAC TGG ATA TCT AAG GAA AAG GGA    12979
Leu Asp Ile Phe Glu Asp Gln Leu Tyr Trp Ile Ser Lys Glu Lys Gly
         4280                    4285                    4290

GAA GTA TGG AAA CAA AAT AAA TTT GGG CAA GTT CGA ATC TTT CAT CAA CTC  13027
Glu Val Trp Lys Gln Asn Lys Phe Gly Gln Val Arg Ile Phe His Gln Leu
        4295                    4300                    4305

CTG GTA GTG AAC CCT TGG CTC ACT CAA GTT CGA ATC TTT CAT CAA CTC    13075
Leu Val Val Asn Pro Trp Leu Thr Gln Val Arg Ile Phe His Gln Leu
4310                    4315                    4320

AGA TAC AAT AAG TCA GTG CCC AAC CTT TGC AAA CAG ATC TGC AGC CAC    13123
Arg Tyr Asn Lys Ser Val Pro Asn Leu Cys Lys Gln Ile Cys Ser His
4325                    4330                    4335

CTC TGC CTT CTG AGA CCT GGA GGA TAC AGC TGT GCC TGT CCC CAA GGC    13171
Leu Cys Leu Leu Arg Pro Gly Gly Tyr Ser Cys Ala Cys Pro Gln Gly
4340                    4345                    4350          4355
```

FIG. 10 cont.

```
TCC AGC TTT ATA GAG GGG AGC ACC ACT GAG TGT GAT GCA GCC ATC GAA    13219
Ser Ser Phe Ile Glu Gly Ser Thr Thr Glu Cys Asp Ala Ala Ile Glu
            4360                        4365                4370

CTG CCT ATC AAC CTG CCC CCA TGC CCC AGG TGC ATG CAC GGA GGA AAT    13267
Leu Pro Ile Asn Leu Pro Pro Cys Pro Arg Cys Met His Gly Gly Asn
            4375                        4380                4385

TGC TAT TTT GAT GAG ACT GAC CTC CCC AAA TGC AAG TGT CCT AGC GGC    13315
Cys Tyr Phe Asp Glu Thr Asp Leu Pro Lys Cys Lys Cys Pro Ser Gly
            4390                        4395                4400

TAC ACC GGA AAA TAT TGT GAA ATG GCG TTT TCA AAA GGC ATC TCT CCA    13363
Tyr Thr Gly Lys Tyr Cys Glu Met Ala Phe Ser Lys Gly Ile Ser Pro
            4405                        4410                4415

GGA ACA ACC GCA GTA GCT GTG CTG CTG ACA ATC CTC TTG ATC GTC GTA    13411
Gly Thr Thr Ala Val Ala Val Leu Leu Thr Ile Leu Leu Ile Val Val
            4420                        4425                4430                4435

ATT GGA GCT CTG CTG GCA GGA TTC CAC TAT AGA AGG ACC GGC            13459
Ile Gly Ala Leu Leu Ala Gly Phe His Tyr Arg Arg Thr Gly
            4440                        4445                4450

TCC CTT TTG CCT GCT CTG CCC AAG CTG CCA AGC TTA AGT AGT CTC GTC    13507
Ser Leu Leu Pro Ala Leu Pro Lys Leu Pro Ser Leu Ser Ser Leu Val
            4455                        4460                4465
```

FIG. 10 cont.

```
AAG CCC TCT GAA AAT GGG GTG ACC TTC AGA TCA GGG GCA GAT       13555
Lys Pro Ser Glu Asn Gly Val Thr Phe Arg Ser Gly Ala Asp
            4470            4475            4480

CTT AAC ATG GAT ATT GGA TCT GGT TTT GGA CCT GAG ACT GCT ATT   13603
Leu Asn Met Asp Ile Gly Val Ser Gly Phe Gly Pro Glu Thr Ala Ile
        4485            4490            4495

GAC AGG TCA ATG GCA ATG AGT GAA GAC TTT GTC ATG GAA ATG GGG AAG 13651
Asp Arg Ser Met Ala Met Ser Glu Asp Phe Val Met Glu Met Gly Lys
    4500            4505            4510            4515

CAG CCC ATA ATA TTT GAA AAC CCA ATG TAC TCA GCC AGA GAC AGT GCT 13699
Gln Pro Ile Ile Phe Glu Asn Pro Met Tyr Ser Ala Arg Asp Ser Ala
            4520            4525            4530

GTG GTT CAG CCA ATC CAG GTG ACT GTA TCT GAA AAT GTG GAT          13747
Val Val Gln Pro Ile Gln Val Thr Val Ser Glu Asn Val Asp
    4535            4540            4545

AAT TAT GGA AGT CCC ATA GTT CCA GAG                              13795
Asn Tyr Gly Ser Pro Ile Val Pro Glu
4550            4455            4460

ACA AAC CCA ACT TCA CCA GCT GAT GGA ACT CAG ACA AAA TGG          13843
Thr Asn Pro Thr Ser Pro Ala Asp Gly Thr Gln Val Thr Lys Trp
    4565            4570            4575
```

FIG. 10 cont.

```
AAT CTC TTC AAA CGA AAA TCT AAA CAA ACT ACC AAC TTT GAA AAT CCA    13891
Asn Leu Phe Lys Arg Lys Ser Lys Gln Thr Thr Asn Phe Glu Asn Pro
4580                4585                4590                4595

ATC TAT GCA CAG ATG GAG AAC GAG CAA AAG AGT GTT GCT GCG ACA       13939
Ile Tyr Ala Gln Met Glu Asn Glu Gln Lys Ser Val Ala Ala Thr
            4600                4605                4610

CCA CCT CCA TCA CCT TCG CTC CCT GCT AAG CCT CCT AGA               13987
Pro Pro Pro Ser Pro Ser Leu Pro Ala Lys Pro Pro Ser Arg
    4615                4620                4625

AGA GAC CCA ACT CCA ACC TAT TCT TAT GCA ACA GAA GAC ACT TTT AAA GAC   14035
Arg Asp Pro Thr Pro Thr Tyr Ser Tyr Ala Thr Glu Asp Thr Phe Lys Asp
4630                4635                4640

ACC GCA AAT CTT GTT AAA GAA GAC TCT GAA GTA TAG GATCAAGAAG        14081
Thr Ala Asn Leu Val Lys Glu Asp Ser Glu Val *
4645                4650                4655

```
                         SEQUENCE LISTING (1) GENERAL INFORMATION:

(iii) NUMBER OF SEQUENCES: 84

(2) INFORMATION FOR SEQ ID NO: 1:

(i) SEQUENCE CHARACTERISTICS:
        (A) LENGTH: 17 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO: 1:

Xaa Ala Met Asn Pro Tyr Ser Leu Asp Ile Phe Glu Asp Gln Leu Tyr
1               5                   10                  15

Trp (2) INFORMATION FOR SEQ ID NO: 2:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO: 2:

Xaa Val Met Gln Pro Asp Gly Ile Ala Xaa Asp Trp Val
1               5                   10

(2) INFORMATION FOR SEQ ID NO: 3:
```

(i) SEQUENCE CHARACTERISTICS:
    (A) LENGTH: 804 base pairs
    (B) TYPE: nucleic acid
    (C) STRANDEDNESS: double
    (D) TOPOLOGY: linear (ii) MOLECULE TYPE: cDNA (ix) FEATURE:
    (A) NAME/KEY: CDS
    (B) LOCATION: 1..804

(xi) SEQUENCE DESCRIPTION: SEQ ID NO: 3:

```
AAA TAC GTA ATG CAG CCA GAT GGA ATA GCA GTG GAC TGG GTT GGA AGG       48
Lys Tyr Val Met Gln Pro Asp Gly Ile Ala Val Asp Trp Val Gly Arg
 1               5                  10                  15

CAT ATT TAC TGG TCA GAT GTC AAG AAT AAA CGC ATT GAG GTG GCT AAA       96
His Ile Tyr Trp Ser Asp Val Lys Asn Lys Arg Ile Glu Val Ala Lys
                20                  25                  30

CTT GAT GGA AGG TAC AGA AAG TGG CTG ATT TCC ACT GAC CTG GAC CAA      144
Leu Asp Gly Arg Tyr Arg Lys Trp Leu Ile Ser Thr Asp Leu Asp Gln
         35                  40                  45

CCA GCT GCT ATT GCT GTG AAT CCC AAA CTA GGG CTT ATG TTC TGG ACT      192
Pro Ala Ala Ile Ala Val Asn Pro Lys Leu Gly Leu Met Phe Trp Thr
 50                  55                  60

GAC TGG GGA AAG GAA CCT AAA ATC GAG TCT GCC TGG ATG AAT GGA GAG      240
Asp Trp Gly Lys Glu Pro Lys Ile Glu Ser Ala Trp Met Asn Gly Glu
 65                  70                  75                  80

GAC CGC AAC ATC CTG GTT TTC GAG GAC CTT GGT TGG CCA ACT GGC CTT      288
Asp Arg Asn Ile Leu Val Phe Glu Asp Leu Gly Trp Pro Thr Gly Leu
                 85                  90                  95

TCT ATC GAT TAT TTG AAC AAT GAC CGA ATC TAC TGG AGT GAC TTC AAG      336
Ser Ile Asp Tyr Leu Asn Asn Asp Arg Ile Tyr Trp Ser Asp Phe Lys
             100                 105                 110

GAG GAC GTT ATT GAA ACC ATA AAA TAT GAT GGG ACT GAT AGG AGA GTC      384
Glu Asp Val Ile Glu Thr Ile Lys Tyr Asp Gly Thr Asp Arg Arg Val
         115                 120                 125

ATT GCA AAG GAA GCA ATG AAC CCT TAC AGC CTG GAC ATC TTT GAA GAC      432
Ile Ala Lys Glu Ala Met Asn Pro Tyr Ser Leu Asp Ile Phe Glu Asp
130                 135                 140

CAG TTA TAC TGG ATA TCT AAG GAA AAG GGA GAA GTA TGG AAA CAA AAT      480
Gln Leu Tyr Trp Ile Ser Lys Glu Lys Gly Glu Val Trp Lys Gln Asn
145                 150                 155                 160

AAA TTT GGG CAA GGA AAG AAA GAG AAA ACG CTG GTA GTG AAC CCT TGG      528
Lys Phe Gly Gln Gly Lys Lys Glu Lys Thr Leu Val Val Asn Pro Trp
                165                 170                 175

CTC ACT CAA GTT CGA ATC TTT CAT CAA CTC AGA TAC AAT AAG TCA GTG      576
Leu Thr Gln Val Arg Ile Phe His Gln Leu Arg Tyr Asn Lys Ser Val
            180                 185                 190

CCC AAC CTT TGC AAA CAG ATC TGC AGC CAC CTC TGC CTT CTG AGA CCT      624
Pro Asn Leu Cys Lys Gln Ile Cys Ser His Leu Cys Leu Leu Arg Pro
        195                 200                 205

GGA GGA TAC AGC TGT GCC TGT CCC CAA GGC TCC AGC TTT ATA GAG GGG      672
Gly Gly Tyr Ser Cys Ala Cys Pro Gln Gly Ser Ser Phe Ile Glu Gly
    210                 215                 220

AGC ACC ACT GAG TGT GAT GCA GCC ATC GAA CTG CCT ATC AAC CTG CCC      720
Ser Thr Thr Glu Cys Asp Ala Ala Ile Glu Leu Pro Ile Asn Leu Pro
225                 230                 235                 240

CCC CCA TGC AGG TGC ATG CAC GGA GGA AAT TGC TAT TTT GAT GAG ACT      768
Pro Pro Cys Arg Cys Met His Gly Gly Asn Cys Tyr Phe Asp Glu Thr
                245                 250                 255
```

```
GAC CTC CCC AAA TGC AAG TGT CCT AGC GGC TAC ACC              804
Asp Leu Pro Lys Cys Lys Cys Pro Ser Gly Tyr Thr
        260                 265
```

(2) INFORMATION FOR SEQ ID NO: 4:

(i) SEQUENCE CHARACTERISTICS:
        (A) LENGTH: 268 amino acids
        (B) TYPE: amino acid
        (D) TOPOLOGY: linear (ii) MOLECULE TYPE: protein (xi) SEQUENCE DESCRIPTION: SEQ ID NO: 4:

```
Lys Tyr Val Met Gln Pro Asp Gly Ile Ala Val Asp Trp Val Gly Arg
 1               5                  10                  15

His Ile Tyr Trp Ser Asp Val Lys Asn Lys Arg Ile Glu Val Ala Lys
             20                  25                  30

Leu Asp Gly Arg Tyr Arg Lys Trp Leu Ile Ser Thr Asp Leu Asp Gln
         35                  40                  45

Pro Ala Ala Ile Ala Val Asn Pro Lys Leu Gly Leu Met Phe Trp Thr
     50                  55                  60

Asp Trp Gly Lys Glu Pro Lys Ile Glu Ser Ala Trp Met Asn Gly Glu
 65                  70                  75                  80

Asp Arg Asn Ile Leu Val Phe Glu Asp Leu Gly Trp Pro Thr Gly Leu
                 85                  90                  95

Ser Ile Asp Tyr Leu Asn Asn Asp Arg Ile Tyr Trp Ser Asp Phe Lys
            100                 105                 110

Glu Asp Val Ile Glu Thr Ile Lys Tyr Asp Gly Thr Asp Arg Arg Val
        115                 120                 125

Ile Ala Lys Glu Ala Met Asn Pro Tyr Ser Leu Asp Ile Phe Glu Asp
130                 135                 140

Gln Leu Tyr Trp Ile Ser Lys Glu Lys Gly Glu Val Trp Lys Gln Asn
145                 150                 155                 160

Lys Phe Gly Gln Gly Lys Lys Gly Lys Thr Leu Val Val Asn Pro Trp
                165                 170                 175

Leu Thr Gln Val Arg Ile Phe His Gln Leu Arg Tyr Asn Lys Ser Val
            180                 185                 190

Pro Asn Leu Cys Lys Gln Ile Cys Ser His Leu Cys Leu Leu Arg Pro
        195                 200                 205

Gly Gly Tyr Ser Cys Ala Cys Pro Gln Gly Ser Ser Phe Ile Glu Gly
    210                 215                 220

Ser Thr Thr Glu Cys Asp Ala Ala Ile Glu Leu Pro Ile Asn Leu Pro
225                 230                 235                 240

Pro Pro Cys Arg Cys Met His Gly Gly Asn Cys Tyr Phe Asp Glu Thr
                245                 250                 255

Asp Leu Pro Lys Cys Lys Cys Pro Ser Gly Tyr Thr
            260                 265
```

(2) INFORMATION FOR SEQ ID NO: 5:

(i) SEQUENCE CHARACTERISTICS:
        (A) LENGTH: 269 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 5:

```
Xaa Xaa Xaa Xaa Xaa Pro Asp Gly Leu Ala Val Asp Trp Val Gly Arg
  1               5                  10                  15

His Ile Tyr Trp Ser Asp Ala Asn Ser Gln Arg Ile Glu Val Ala Thr
                 20                  25                  30

Leu Asp Gly Arg Tyr Arg Lys Trp Leu Ile Thr Thr Gln Leu Asp Gln
             35                  40                  45

Pro Ala Ala Ile Ala Val Asn Pro Lys Leu Gly Leu Met Phe Trp Thr
         50                  55                  60

Asp Gln Gly Lys Gln Pro Lys Ile Glu Ser Ala Trp Met Asn Gly Glu
 65                  70                  75                  80

His Arg Ser Val Leu Val Ser Glu Asn Leu Gly Trp Pro Asn Gly Leu
                 85                  90                  95

Ser Ile Asp Tyr Leu Asn Asp Arg Val Tyr Trp Ser Asp Ser Lys
                100                 105                 110

Glu Asp Val Ile Glu Ala Ile Lys Tyr Asp Gly Thr Asp Arg Arg Leu
                115                 120                 125

Ile Ile Asn Glu Ala Met Lys Pro Phe Ser Leu Asp Ile Phe Glu Asp
        130                 135                 140

Lys Leu Tyr Trp Val Ala Xaa Xaa Xaa Xaa Xaa Xaa Xaa Arg Gln
145                 150                 155                 160

Asn Lys Phe Gly Lys Glu Asn Lys Glu Lys Val Leu Val Val Asn Pro
                165                 170                 175

Trp Leu Thr Gln Val Arg Xaa Xaa Xaa Xaa Xaa Xaa Xaa Xaa Xaa
                180                 185                 190

Xaa Xaa Xaa Xaa Cys Lys Gln Val Cys Ser His Leu Cys Leu Leu Arg
        195                 200                 205

Pro Gly Gly Tyr Ser Cys Ala Cys Pro Gln Gly Ser Asp Phe Val Thr
        210                 215                 220

Gly Ser Thr Val Gln Cys Xaa Xaa Xaa Xaa Xaa Pro Val Thr Met
225                 230                 235                 240

Pro Pro Pro Cys Arg Cys Met His Gly Gly Asn Cys Tyr Phe Asp Glu
                245                 250                 255

Asn Glu Leu Pro Lys Cys Lys Cys Ser Ser Gly Tyr Ser
                260                 265

(2) INFORMATION FOR SEQ ID NO: 6:

(i) SEQUENCE CHARACTERISTICS:
        (A) LENGTH: 280 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 6:

Arg Asp Ile Gln Ala Pro Asp Gly Leu Ala Val Asp Trp Ile His Ser
  1               5                  10                  15

Asn Ile Tyr Trp Thr Asp Ser Val Leu Gly Thr Val Ser Val Ala Asp
                 20                  25                  30

Thr Lys Gly Val Lys Arg Lys Thr Leu Phe Arg Glu Asn Gly Ser Lys
             35                  40                  45

Pro Arg Ala Ile Val Val Asp Pro Val His Gly Phe Met Tyr Trp Thr
         50                  55                  60

Asp Trp Gly Thr Pro Ala Lys Ile Lys Lys Gly Gly Leu Asn Gly Val
 65                  70                  75                  80
```

```
Asp Ile Tyr Ser Leu Val Thr Glu Asn Ile Gln Trp Pro Asn Gly Ile
            85                  90                  95

Thr Leu Asp Leu Leu Ser Gly Arg Leu Tyr Trp Val Asp Ser Lys Leu
            100                 105                 110

His Ser Ile Ser Ser Ile Asp Tyr Asn Gly Gly Asn Arg Lys Thr Ile
            115                 120                 125

Leu Glu Asp Glu Lys Arg Leu Ala His Pro Phe Ser Leu Ala Val Phe
            130                 135             140

Glu Asp Lys Val Phe Trp Thr Asp Ile Ile Asn Glu Ala Ile Phe Ser
145                 150                 155                 160

Ala Asn Arg Leu Thr Gly Ser Asp Val Asn Leu Leu Ala Glu Asn Leu
            165                 170                 175

Leu Ser Pro Glu Asp Met Val Leu Phe His Asn Leu Thr Gln Pro Arg
            180                 185                 190

Gly Val Asn Trp Cys Glu Arg Thr Thr Leu Ser Asn Gly Gly Cys Gln
            195                 200                 205

Tyr Leu Cys Leu Pro Ala Pro Gln Ile Asn Pro His Ser Pro Lys Phe
            210                 215                 220

Thr Cys Ala Cys Pro Asp Gly Met Leu Leu Ala Arg Asp Met Arg Ser
225                 230                 235                 240

Cys Leu Thr Glu Ala Glu Ala Val Ala Thr Gln Glu Thr Ser Thr
            245                 250                 255

Val Arg Leu Lys Val Ser Ser Thr Ala Val Arg Thr Gln His Thr Thr
            260                 265                 270

Thr Arg Pro Val Pro Asp Thr Ser
            275             280

(2) INFORMATION FOR SEQ ID NO: 7:

(i) SEQUENCE CHARACTERISTICS:
        (A) LENGTH: 281 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 7:

Thr Gly Leu Ser Asn Pro Asp Gly Leu Ala Val Asp Trp Val Gly Gly
1               5                   10                  15

Asn Leu Tyr Trp Cys Asp Lys Gly Arg Asp Thr Ile Glu Val Ser Lys
            20                  25                  30

Leu Asn Gly Ala Tyr Arg Thr Val Leu Val Ser Gly Leu Arg Glu
            35                  40                  45

Pro Arg Ala Leu Val Val Asp Val Gln Asn Gly Tyr Leu Tyr Trp Thr
50                  55                  60

Asp Trp Gly Asp His Ser Leu Ile Gly Arg Ile Gly Met Asp Gly Ser
65                  70                  75                  80

Ser Arg Ser Val Ile Val Asp Thr Lys Ile Thr Trp Pro Asn Gly Leu
            85                  90                  95

Thr Leu Asp Tyr Val Thr Glu Arg Ile Tyr Trp Ala Asp Ala Arg Glu
            100                 105                 110

Asp Tyr Ile Glu Phe Ala Ser Leu Asp Gly Ser Asn Arg His Val Val
            115                 120                 125

Leu Ser Gln Asp Ile Pro His Ile Phe Ala Leu Thr Leu Phe Glu Asp
            130                 135             140
```

```
Tyr Val Tyr Trp Thr Asp Trp Glu Thr Lys Ser Ile Asn Arg Ala His
145                 150                 155                 160

Lys Thr Thr Gly Thr Asn Lys Thr Leu Leu Ile Ser Thr Leu His Arg
            165                 170                 175

Pro Met Asp Leu His Val Phe His Ala Leu Arg Gln Pro Asp Val Pro
            180                 185                 190

Asn His Pro Cys Lys Val Asn Asn Gly Gly Cys Ser Asn Leu Cys Leu
            195                 200                 205

Leu Ser Pro Gly Gly His Lys Cys Ala Cys Pro Thr Asn Phe Tyr
210                 215                 220

Leu Gly Ser Asp Gly Arg Thr Cys Val Ser Asn Cys Thr Ala Ser Gln
225                 230                 235                 240

Phe Val Cys Lys Asn Asp Lys Cys Ile Pro Phe Trp Trp Lys Cys Asp
                245                 250                 255

Thr Glu Asp Asp Cys Gly Asp His Ser Asp Glu Pro Pro Asp Cys Pro
            260                 265                 270

Glu Phe Lys Cys Arg Pro Gly Gln Phe
275                 280
```

(2) INFORMATION FOR SEQ ID NO: 8:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (ix) FEATURE:
        (A) NAME/KEY: modified_base
        (B) LOCATION: 7
        (D) OTHER INFORMATION: /mod_base= i (ix) FEATURE:
        (A) NAME/KEY: modified_base
        (B) LOCATION: 28
        (D) OTHER INFORMATION: /mod_base= i (ix) FEATURE:
        (A) NAME/KEY: modified_base
        (B) LOCATION: 31
        (D) OTHER INFORMATION: /mod_base= i (ix) FEATURE:
        (A) NAME/KEY: modified_base
        (B) LOCATION: 37
        (D) OTHER INFORMATION: /mod_base= i (ix) FEATURE:
        (A) NAME/KEY: modified_base
        (B) LOCATION: 46
        (D) OTHER INFORMATION: /mod_base= i (xi) SEQUENCE DESCRIPTION: SEQ ID NO: 8:

CCARTANAGC TGRTCCTCRA AGATRTCNAG NGARTANGGR TTCATNGC          48

(2) INFORMATION FOR SEQ ID NO: 9:

(i) SEQUENCE CHARACTERISTICS:
        (A) LENGTH: 26 base pairs
        (B) TYPE: nucleic acid
        (C) STRANDEDNESS: single (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO: 9:

GCGGAATTCG TNATGCARCC NGAYGG                                        26

(2) INFORMATION FOR SEQ ID NO: 10:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO: 10:

ATAGGAATCC TGRTCYTCRA ADATRTC                                       27

(2) INFORMATION FOR SEQ ID NO: 11:

(i) SEQUENCE CHARACTERISTICS:
        (A) LENGTH: 2832 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1..2832

(xi) SEQUENCE DESCRIPTION: SEQ ID NO: 11:

```
CAA GGC TGT GAG GAG AGG ACA TGC CAT CCT GTG GGG GAT TTC CGC TGT      48
Gln Gly Cys Glu Glu Arg Thr Cys His Pro Val Gly Asp Phe Arg Cys
    270                 275                 280

AAA ACT CAC CAC TGC ATC CCT CTT CGT TGG CAG TGT GAT GGG CAA AAT      96
Lys Thr His His Cys Ile Pro Leu Arg Trp Gln Cys Asp Gly Gln Asn
285                 290                 295                 300

GAC TGT GGA GAT AAC TCA GAT GAG GAA AAC TGT GCT CCC CGG GAG TGC     144
Asp Cys Gly Asp Asn Ser Asp Glu Glu Asn Cys Ala Pro Arg Glu Cys
                305                 310                 315

ACA GAG AGC GAG TTT CGA TGT GTC AAT CAG CAG TGC ATT CCC TCG CGA     192
Thr Glu Ser Glu Phe Arg Cys Val Asn Gln Gln Cys Ile Pro Ser Arg
            320                 325                 330

TGG ATC TGT GAC CAT TAC AAC GAC TGT GGG GAC AAC TCA GAT GAA CGG     240
Trp Ile Cys Asp His Tyr Asn Asp Cys Gly Asp Asn Ser Asp Glu Arg
        335                 340                 345

GAC TGT GAG ATG AGG ACC TGC CAT CCT GAA TAT TTT CAG TGT ACA AGT     288
Asp Cys Glu Met Arg Thr Cys His Pro Glu Tyr Phe Gln Cys Thr Ser
    350                 355                 360

GGA CAT TGT GTA CAC AGT GAA CTG AAA TGC GAT GGA TCC GCT GAC TGT     336
Gly His Cys Val His Ser Glu Leu Lys Cys Asp Gly Ser Ala Asp Cys
365                 370                 375                 380
```

```
TTG GAT GCG TCT GAT GAA GCT GAT TGT CCC ACA CGC TTT CCT GAT GGT        384
Leu Asp Ala Ser Asp Glu Ala Asp Cys Pro Thr Arg Phe Pro Asp Gly
            385                 390                 395

GCA TAC TGC CAG GCT ACT ATG TTC GAA TGC AAA AAC CAT GTT TGT ATC        432
Ala Tyr Cys Gln Ala Thr Met Phe Glu Cys Lys Asn His Val Cys Ile
                400                 405                 410

CCG CCA TAT TGG AAA TGT GAT GGC GAT GAT GAC TGT GGC GAT GGT TCA        480
Pro Pro Tyr Trp Lys Cys Asp Gly Asp Asp Asp Cys Gly Asp Gly Ser
            415                 420                 425

GAT GAA GAA CTT CAC CTG TGC TTG GAT GTT CCC TGT AAT TCA CCA AAC        528
Asp Glu Glu Leu His Leu Cys Leu Asp Val Pro Cys Asn Ser Pro Asn
        430                 435                 440

CGT TTC CGG TGT GAC AAC AAT CGC TGC ATT TAT AGT CAT GAG GTG TGC        576
Arg Phe Arg Cys Asp Asn Asn Arg Cys Ile Tyr Ser His Glu Val Cys
445                 450                 455                 460

AAT GGT GTG GAT GAC TGT GGA GAT GGA ACT GAT GAG ACA GAG GAG CAC        624
Asn Gly Val Asp Asp Cys Gly Asp Gly Thr Asp Glu Thr Glu Glu His
                465                 470                 475

TGT AGA AAA CCG ACC CCT AAA CCT TGT ACA GAA TAT GAA TAT AAG TGT        672
Cys Arg Lys Pro Thr Pro Lys Pro Cys Thr Glu Tyr Glu Tyr Lys Cys
            480                 485                 490

GGC AAT GGG CAT TGC ATT CCA CAT GAC AAT GTG TGT GAT GAT GCC GAT        720
Gly Asn Gly His Cys Ile Pro His Asp Asn Val Cys Asp Asp Ala Asp
        495                 500                 505

GAC TGT GGT GAC TGG TCC GAT GAA CTG GGT TGC AAT AAA GGA AAA GAA        768
Asp Cys Gly Asp Trp Ser Asp Glu Leu Gly Cys Asn Lys Gly Lys Glu
    510                 515                 520

AGA ACA TGT GCT GAA AAT ATA TGC GAG CAA AAT TGT ACC CAA TTA AAT        816
Arg Thr Cys Ala Glu Asn Ile Cys Glu Gln Asn Cys Thr Gln Leu Asn
525                 530                 535                 540

GAA GGA GGA TTT ATC TGC TCC TGT ACA GCT GGG TTC GAA ACC AAT GTT        864
Glu Gly Gly Phe Ile Cys Ser Cys Thr Ala Gly Phe Glu Thr Asn Val
                545                 550                 555

TTT GAC AGA ACC TCC TGT CTA GAT ATC AAT GAA TGT GAA CAA TTT GGG        912
Phe Asp Arg Thr Ser Cys Leu Asp Ile Asn Glu Cys Glu Gln Phe Gly
            560                 565                 570

ACT TGT CCC CAG CAC TGC AGA AAT ACC AAA GGA AGT TAT GAG TGT GTC        960
Thr Cys Pro Gln His Cys Arg Asn Thr Lys Gly Ser Tyr Glu Cys Val
        575                 580                 585

TGT GCT GAT GGC TTC ACG TCT ATG AGT GAC CGC CCT GGA AAA CGA TGT        1008
Cys Ala Asp Gly Phe Thr Ser Met Ser Asp Arg Pro Gly Lys Arg Cys
    590                 595                 600

GCA GCT GAG GGT AGC TCT CCT TTG TTG CTA CTG CCT GAC AAT GTC CGA        1056
Ala Ala Glu Gly Ser Ser Pro Leu Leu Leu Leu Pro Asp Asn Val Arg
605                 610                 615                 620

ATT CGA AAA TAT AAT CTC TCA TCT GAG AGG TTC TCA GAG TAT CTT CAA        1104
Ile Arg Lys Tyr Asn Leu Ser Ser Glu Arg Phe Ser Glu Tyr Leu Gln
                625                 630                 635

GAT GAG GAA TAT ATC CAA GCT GTT GAT TAT GAT TGG GAT CCC AAG GAC        1152
Asp Glu Glu Tyr Ile Gln Ala Val Asp Tyr Asp Trp Asp Pro Lys Asp
            640                 645                 650

ATA GGC CTC AGT GTT GTG TAT TAC ACT GTG CGA GGG GAG GGC TCT AGG        1200
Ile Gly Leu Ser Val Val Tyr Tyr Thr Val Arg Gly Glu Gly Ser Arg
        655                 660                 665

TTT GGT GCT ATC AAA CGT GCC TAC ATC CCC AAC TTT GAA TCC GGC CGC        1248
Phe Gly Ala Ile Lys Arg Ala Tyr Ile Pro Asn Phe Glu Ser Gly Arg
    670                 675                 680

AAT AAT CTT GTG CAG GAA GTT GAC CTG AAA CTG AAA TAC GTA ATG CAG        1296
Asn Asn Leu Val Gln Glu Val Asp Leu Lys Leu Lys Tyr Val Met Gln
```

```
 685                  690                  695                  700
CCA GAT GGA ATA GCA GTG GAC TGG GTT GGA AGG CAT ATT TAC TGG TCA      1344
Pro Asp Gly Ile Ala Val Asp Trp Val Gly Arg His Ile Tyr Trp Ser
                705                  710                  715

GAT GTC AAG AAT AAA CGC ATT GAG GTG GCT AAA CTT GAT GGA AGG TAC      1392
Asp Val Lys Asn Lys Arg Ile Glu Val Ala Lys Leu Asp Gly Arg Tyr
                720                  725                  730

AGA AAG TGG CTG ATT TCC ACT GAC CTG GAC CAA CCA GCT GCT ATT GCT      1440
Arg Lys Trp Leu Ile Ser Thr Asp Leu Asp Gln Pro Ala Ala Ile Ala
                735                  740                  745

GTG AAT CCC AAA CTA GGG CTT ATG TTC TGG ACT GAC TGG GGA AAG GAA      1488
Val Asn Pro Lys Leu Gly Leu Met Phe Trp Thr Asp Trp Gly Lys Glu
                750                  755                  760

CCT AAA ATC GAG TCT GCC TGG ATG AAT GGA GAG GAC CGC AAC ATC CTG      1536
Pro Lys Ile Glu Ser Ala Trp Met Asn Gly Glu Asp Arg Asn Ile Leu
765                  770                  775                  780

GTT TTC GAG GAC CTT GGT TGG CCA ACT GGC CTT TCT ATC GAT TAT TTG      1584
Val Phe Glu Asp Leu Gly Trp Pro Thr Gly Leu Ser Ile Asp Tyr Leu
                785                  790                  795

AAC GAC CGA ATC TAC TGG AGT GAC TTC AAG GAG GAC GTT ATT GAA ACC      1632
Asn Asp Arg Ile Tyr Trp Ser Asp Phe Lys Glu Asp Val Ile Glu Thr
                800                  805                  810

ATA AAA TAT GAT GGG ACT GAT AGG AGA GTC ATT GCA AAG GAA GCA ATG      1680
Ile Lys Tyr Asp Gly Thr Asp Arg Arg Val Ile Ala Lys Glu Ala Met
                815                  820                  825

AAC CCT TAC AGC CTG GAC ATC TTT GAA GAC CAG TTA TAC TGG ATA TCT      1728
Asn Pro Tyr Ser Leu Asp Ile Phe Glu Asp Gln Leu Tyr Trp Ile Ser
830                  835                  840

AAG GAA AAG GGA GAA GTA TGG AAA CAA AAT AAA TTT GGG CAA GGA AAG      1776
Lys Glu Lys Gly Glu Val Trp Lys Gln Asn Lys Phe Gly Gln Gly Lys
845                  850                  855                  860

AAA GAG AAA ACG CTG GTA GTG AAC CCT TGG CTC ACT CAA GTT CGA ATC      1824
Lys Glu Lys Thr Leu Val Val Asn Pro Trp Leu Thr Gln Val Arg Ile
                865                  870                  875

TTT CAT CAA CTC AGA TAC AAT AAG TCA GTG CCC AAC CTT TGC AAA CAG      1872
Phe His Gln Leu Arg Tyr Asn Lys Ser Val Pro Asn Leu Cys Lys Gln
                880                  885                  890

ATC TGC AGC CAC CTC TGC CTT CTG AGA CCT GGA GGA TAC AGC TGT GCC      1920
Ile Cys Ser His Leu Cys Leu Leu Arg Pro Gly Gly Tyr Ser Cys Ala
                895                  900                  905

TGT CCC CAA GGC TCC AGC TTT ATA GAG GGG AGC ACC ACT GAG TGT GAT      1968
Cys Pro Gln Gly Ser Ser Phe Ile Glu Gly Ser Thr Thr Glu Cys Asp
                910                  915                  920

GCA GCC ATC GAA CTG CCT ATC AAC CTG CCC CCC CCA TGC AGG TGC ATG      2016
Ala Ala Ile Glu Leu Pro Ile Asn Leu Pro Pro Pro Cys Arg Cys Met
925                  930                  935                  940

CAC GGA GGA AAT TGC TAT TTT GAT GAG ACT GAC CTC CCC AAA TGC AAG      2064
His Gly Gly Asn Cys Tyr Phe Asp Glu Thr Asp Leu Pro Lys Cys Lys
                945                  950                  955

TGT CCT AGC GGC TAC ACC GGA AAA TAT TGT GAA ATG GCG TTT TCA AAA      2112
Cys Pro Ser Gly Tyr Thr Gly Lys Tyr Cys Glu Met Ala Phe Ser Lys
                960                  965                  970

GGC ATC TCT CCA GGA ACA ACC GCA GTA GCT GTG CTG TTG ACA ATC CTC      2160
Gly Ile Ser Pro Gly Thr Thr Ala Val Ala Val Leu Leu Thr Ile Leu
                975                  980                  985

TTG ATC GTC GTA ATT GGA GCT CTG GCA ATT GCA GGA TTC TTC CAC TAT      2208
Leu Ile Val Val Ile Gly Ala Leu Ala Ile Ala Gly Phe Phe His Tyr
                990                  995                  1000

AGA AGG ACC GGC TCC CTT TTG CCT GCT CTG CCC AAG CTG CCA AGC TTA      2256
```

```
Arg Arg Thr Gly Ser Leu Leu Pro Ala Leu Pro Lys Leu Pro Ser Leu
1005                1010                1015                1020

AGC AGT CTC GTC AAG CCC TCT GAA AAT GGG AAT GGG GTG ACC TTC AGA      2304
Ser Ser Leu Val Lys Pro Ser Glu Asn Gly Asn Gly Val Thr Phe Arg
                1025                1030                1035

TCA GGG GCA GAT CTT AAC ATG GAT ATT GGA GTG TCT GGT TTT GGA CCT      2352
Ser Gly Ala Asp Leu Asn Met Asp Ile Gly Val Ser Gly Phe Gly Pro
            1040                1045                1050

GAG ACT GCT ATT GAC AGG TCA ATG GCA ATG AGT GAA GAC TTT GTC ATG      2400
Glu Thr Ala Ile Asp Arg Ser Met Ala Met Ser Glu Asp Phe Val Met
                1055                1060                1065

GAA ATG GGG AAG CAG CCC ATA ATA TTT GAA AAC CCA ATG TAC TCA GCC      2448
Glu Met Gly Lys Gln Pro Ile Ile Phe Glu Asn Pro Met Tyr Ser Ala
            1070                1075                1080

AGA GAC AGT GCT GTC AAA GTG GTT CAG CCA ATC CAG GTG ACT GTA TCT      2496
Arg Asp Ser Ala Val Lys Val Val Gln Pro Ile Gln Val Thr Val Ser
1085                1090                1095                1100

GAA AAT GTG GAT AAT AAG AAT TAT GGA AGT CCC ATA AAC CCT TCT GAG      2544
Glu Asn Val Asp Asn Lys Asn Tyr Gly Ser Pro Ile Asn Pro Ser Glu
                1105                1110                1115

ATA GTT CCA GAG ACA AAC CCA ACT TCA CCA GCT GCT GAT GGA ACT CAG      2592
Ile Val Pro Glu Thr Asn Pro Thr Ser Pro Ala Ala Asp Gly Thr Gln
            1120                1125                1130

GTG ACA AAA TGG AAT CTC TTC AAA CGA AAA TCT AAA CAA ACT ACC AAC      2640
Val Thr Lys Trp Asn Leu Phe Lys Arg Lys Ser Lys Gln Thr Thr Asn
            1135                1140                1145

TTT GAA AAT CCA ATC TAT GCA CAG ATG GAG AAC GAG CAA AAG GAA AGT      2688
Phe Glu Asn Pro Ile Tyr Ala Gln Met Glu Asn Glu Gln Lys Glu Ser
            1150                1155                1160

GTT GCT GCG ACA CCA CCT CCA TCA CCT TCG CTC CCT GCT AAG CCT AAG      2736
Val Ala Ala Thr Pro Pro Pro Ser Pro Ser Leu Pro Ala Lys Pro Lys
1165                1170                1175                1180

CCT CCT TCG AGA AGA GAC CCA ACT CCA ACC TAT TCT GCA ACA GAA GAC      2784
Pro Pro Ser Arg Arg Asp Pro Thr Pro Thr Tyr Ser Ala Thr Glu Asp
                1185                1190                1195

ACT TTT AAA GAC ACC GCA AAT CTT GTT AAA GAA GAC TCT GAA GTA TAG      2832
Thr Phe Lys Asp Thr Ala Asn Leu Val Lys Glu Asp Ser Glu Val *
            1200                1205                1210

(2) INFORMATION FOR SEQ ID NO: 12:

(i) SEQUENCE CHARACTERISTICS:
        (A) LENGTH: 943 amino acids
        (B) TYPE: amino acid
        (D) TOPOLOGY: linear (ii) MOLECULE TYPE: protein (xi) SEQUENCE DESCRIPTION: SEQ ID NO: 12:

Gln Gly Cys Glu Glu Arg Thr Cys His Pro Val Gly Asp Phe Arg Cys
 1               5                  10                  15

Lys Thr His His Cys Ile Pro Leu Arg Trp Gln Cys Asp Gly Gln Asn
                20                  25                  30

Asp Cys Gly Asp Asn Ser Asp Glu Glu Asn Cys Ala Pro Arg Glu Cys
            35                  40                  45

Thr Glu Ser Glu Phe Arg Cys Val Asn Gln Gln Cys Ile Pro Ser Arg
        50                  55                  60

Trp Ile Cys Asp His Tyr Asn Asp Cys Gly Asp Asn Ser Asp Glu Arg
65                  70                  75                  80

Asp Cys Glu Met Arg Thr Cys His Pro Glu Tyr Phe Gln Cys Thr Ser
```

-continued

```
                85                    90                    95
Gly His Cys Val His Ser Glu Leu Lys Cys Asp Gly Ser Ala Asp Cys
                100                   105                   110

Leu Asp Ala Ser Asp Glu Ala Asp Cys Pro Thr Arg Phe Pro Asp Gly
            115                   120                   125

Ala Tyr Cys Gln Ala Thr Met Phe Glu Cys Lys Asn His Val Cys Ile
        130                   135                   140

Pro Pro Tyr Trp Lys Cys Asp Gly Asp Asp Cys Gly Asp Gly Ser
145                 150                   155                   160

Asp Glu Glu Leu His Leu Cys Leu Asp Val Pro Cys Asn Ser Pro Asn
                165                   170                   175

Arg Phe Arg Cys Asp Asn Asn Arg Cys Ile Tyr Ser His Glu Val Cys
            180                   185                   190

Asn Gly Val Asp Asp Cys Gly Asp Gly Thr Asp Glu Thr Glu Glu His
        195                   200                   205

Cys Arg Lys Pro Thr Pro Lys Pro Cys Thr Glu Tyr Glu Tyr Lys Cys
    210                   215                   220

Gly Asn Gly His Cys Ile Pro His Asp Asn Val Cys Asp Asp Ala Asp
225                 230                   235                   240

Asp Cys Gly Asp Trp Ser Asp Glu Leu Gly Cys Asn Lys Gly Lys Glu
                245                   250                   255

Arg Thr Cys Ala Glu Asn Ile Cys Glu Gln Asn Cys Thr Gln Leu Asn
            260                   265                   270

Glu Gly Gly Phe Ile Cys Ser Cys Thr Ala Gly Phe Glu Thr Asn Val
        275                   280                   285

Phe Asp Arg Thr Ser Cys Leu Asp Ile Asn Glu Cys Glu Gln Phe Gly
    290                   295                   300

Thr Cys Pro Gln His Cys Arg Asn Thr Lys Gly Ser Tyr Glu Cys Val
305                 310                   315                   320

Cys Ala Asp Gly Phe Thr Ser Met Ser Asp Arg Pro Gly Lys Arg Cys
                325                   330                   335

Ala Ala Glu Gly Ser Ser Pro Leu Leu Leu Pro Asp Asn Val Arg
            340                   345                   350

Ile Arg Lys Tyr Asn Leu Ser Ser Glu Arg Phe Ser Glu Tyr Leu Gln
        355                   360                   365

Asp Glu Glu Tyr Ile Gln Ala Val Asp Tyr Asp Trp Asp Pro Lys Asp
    370                   375                   380

Ile Gly Leu Ser Val Val Tyr Tyr Thr Val Arg Gly Glu Gly Ser Arg
385                 390                   395                   400

Phe Gly Ala Ile Lys Arg Ala Tyr Ile Pro Asn Phe Glu Ser Gly Arg
                405                   410                   415

Asn Asn Leu Val Gln Glu Val Asp Leu Lys Leu Lys Tyr Val Met Gln
            420                   425                   430

Pro Asp Gly Ile Ala Val Asp Trp Val Gly Arg His Ile Tyr Trp Ser
        435                   440                   445

Asp Val Lys Asn Lys Arg Ile Glu Val Ala Lys Leu Asp Gly Arg Tyr
    450                   455                   460

Arg Lys Trp Leu Ile Ser Thr Asp Leu Asp Gln Pro Ala Ala Ile Ala
465                 470                   475                   480

Val Asn Pro Lys Leu Gly Leu Met Phe Trp Thr Asp Trp Gly Lys Glu
                485                   490                   495

Pro Lys Ile Glu Ser Ala Trp Met Asn Gly Glu Asp Arg Asn Ile Leu
            500                   505                   510
```

-continued

```
Val Phe Glu Asp Leu Gly Trp Pro Thr Gly Leu Ser Ile Asp Tyr Leu
        515                 520                 525
Asn Asp Arg Ile Tyr Trp Ser Asp Phe Lys Glu Asp Val Ile Glu Thr
    530                 535                 540
Ile Lys Tyr Asp Gly Thr Asp Arg Arg Val Ile Ala Lys Glu Ala Met
545                 550                 555                 560
Asn Pro Tyr Ser Leu Asp Ile Phe Glu Asp Gln Leu Tyr Trp Ile Ser
                565                 570                 575
Lys Glu Lys Gly Glu Val Trp Lys Gln Asn Lys Phe Gly Gln Gly Lys
            580                 585                 590
Lys Glu Lys Thr Leu Val Val Asn Pro Trp Leu Thr Gln Val Arg Ile
        595                 600                 605
Phe His Gln Leu Arg Tyr Asn Lys Ser Val Pro Asn Leu Cys Lys Gln
    610                 615                 620
Ile Cys Ser His Leu Cys Leu Leu Arg Pro Gly Gly Tyr Ser Cys Ala
625                 630                 635                 640
Cys Pro Gln Gly Ser Ser Phe Ile Glu Gly Ser Thr Thr Glu Cys Asp
                645                 650                 655
Ala Ala Ile Glu Leu Pro Ile Asn Leu Pro Pro Cys Arg Cys Met
            660                 665                 670
His Gly Gly Asn Cys Tyr Phe Asp Glu Thr Asp Leu Pro Lys Cys Lys
        675                 680                 685
Cys Pro Ser Gly Tyr Thr Gly Lys Tyr Cys Glu Met Ala Phe Ser Lys
    690                 695                 700
Gly Ile Ser Pro Gly Thr Thr Ala Val Ala Val Leu Leu Thr Ile Leu
705                 710                 715                 720
Leu Ile Val Val Ile Gly Ala Leu Ala Ile Ala Gly Phe Phe His Tyr
                725                 730                 735
Arg Arg Thr Gly Ser Leu Leu Pro Ala Leu Pro Lys Leu Pro Ser Leu
            740                 745                 750
Ser Ser Leu Val Lys Pro Ser Glu Asn Gly Asn Gly Val Thr Phe Arg
        755                 760                 765
Ser Gly Ala Asp Leu Asn Met Asp Ile Gly Val Ser Gly Phe Gly Pro
    770                 775                 780
Glu Thr Ala Ile Asp Arg Ser Met Ala Met Ser Glu Asp Phe Val Met
785                 790                 795                 800
Glu Met Gly Lys Gln Pro Ile Ile Phe Glu Asn Pro Met Tyr Ser Ala
                805                 810                 815
Arg Asp Ser Ala Val Lys Val Val Gln Pro Ile Gln Val Thr Val Ser
            820                 825                 830
Glu Asn Val Asp Asn Lys Asn Tyr Gly Ser Pro Ile Asn Pro Ser Glu
        835                 840                 845
Ile Val Pro Glu Thr Asn Pro Thr Ser Pro Ala Ala Asp Gly Thr Gln
    850                 855                 860
Val Thr Lys Trp Asn Leu Phe Lys Arg Lys Ser Lys Gln Thr Thr Asn
865                 870                 875                 880
Phe Glu Asn Pro Ile Tyr Ala Gln Met Glu Asn Glu Gln Lys Glu Ser
                885                 890                 895
Val Ala Ala Thr Pro Pro Pro Ser Pro Ser Leu Pro Ala Lys Pro Lys
            900                 905                 910
Pro Pro Ser Arg Arg Asp Pro Thr Pro Thr Tyr Ser Ala Thr Glu Asp
        915                 920                 925
```

```
Thr Phe Lys Asp Thr Ala Asn Leu Val Lys Glu Asp Ser Glu Val
    930                 935                 940
```

(2) INFORMATION FOR SEQ ID NO: 13:

(i) SEQUENCE CHARACTERISTICS:
        (A) LENGTH: 207 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: C-terminal (xi) SEQUENCE DESCRIPTION: SEQ ID NO: 13:

```
Arg Arg Thr Gly Ser Leu Leu Pro Ala Leu Pro Lys Leu Pro Ser Leu
1               5                   10                  15

Ser Ser Leu Val Lys Pro Ser Glu Asn Gly Asn Gly Val Thr Phe Arg
            20                  25                  30

Ser Gly Ala Asp Leu Asn Met Asp Ile Gly Val Ser Gly Phe Gly Pro
            35                  40                  45

Glu Thr Ala Ile Asp Arg Ser Met Ala Met Ser Glu Asp Phe Val Met
        50                  55                  60

Glu Met Gly Lys Gln Pro Ile Ile Phe Glu Asn Pro Met Tyr Ser Ala
65                  70                  75                  80

Arg Asp Ser Ala Val Lys Val Gln Pro Ile Gln Val Thr Val Ser
                85                  90                  95

Glu Asn Val Asp Asn Lys Asn Tyr Gly Ser Pro Ile Asn Pro Ser Glu
            100                 105                 110

Ile Val Pro Glu Thr Asn Pro Thr Ser Pro Ala Ala Asp Gly Thr Gln
            115                 120                 125

Val Thr Lys Trp Asn Leu Phe Lys Arg Lys Ser Lys Gln Thr Thr Asn
        130                 135                 140

Phe Glu Asn Pro Ile Tyr Ala Gln Met Glu Asn Glu Gln Lys Glu Ser
145                 150                 155                 160

Val Ala Ala Thr Pro Pro Ser Pro Ser Leu Pro Ala Lys Pro Lys
                165                 170                 175

Pro Pro Ser Arg Arg Asp Pro Thr Pro Thr Tyr Ser Ala Thr Glu Asp
            180                 185                 190

Thr Phe Lys Asp Thr Ala Asn Leu Val Lys Glu Asp Ser Glu Val
        195                 200                 205
```

(2) INFORMATION FOR SEQ ID NO: 14:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 14:

```
Pro Ser Leu Pro Ala Lys Pro
1               5
```

(2) INFORMATION FOR SEQ ID NO: 15:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 15:

Ser Leu Leu Pro Ala Leu Pro
1           5

(2) INFORMATION FOR SEQ ID NO: 16:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 16:

Pro Ala Leu Pro Lys Leu Pro
1           5

(2) INFORMATION FOR SEQ ID NO: 17:

(i) SEQUENCE CHARACTERISTICS:
        (A) LENGTH: 6412 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 17:

```
GAATTCTGTC AATGAGCTGG CCTTCCTTAT AAAAGGATTT ACATTTTCTG CTTAAGAGGT      60

ATTATTTATA GTTTGAAATA TTTCTGGTGA TATTTGCGGG TGGGATCATA TGTGCTTCAT     120

TGTGCATTTT ATAAAGAACA ACAAATTCAC GGGAAGATGT GCCTTTTGAT GTTGTTGCTT     180

TGCAAATTTT GCTGAGAAGA GTCGTTGATA TTTCCTGTTG TTTAGAAGGA ATCGGCACAT     240

TTATTAGAAA TTGGTGATTG CTCTTCTTGA TGGAAAAGTG ACTCAGAATA TAGTTAAAAG     300

GTTAATGGGC AGAACTTCCA TGGCGCTTCT TAGGGAGCAT TTAATGTAGA AGCTGTTGCA     360

AGTGCTATTG TGGAGGGGTC AATGTGAACG GTGGCTGCAT CCATCTTTTA CTTCTTCTGG     420

GATTATCTTT CTTCAGGTCC GGGTGGTGCC GAGTGCCAGT GTCCACATGA GGGCAACTGG     480

TATTTGGCCA ACAACAGGAA GCACTGCATT GTGGACAATG GTGAACGATG TGGTGCATCT     540

TCCTTCACCT GCTCCAATGG GCGCTGCATC TCGGAAGAGT GGAAGTGTGA TAATGACAAC     600

GACTGTGGGG ATGGCAGTGA TGAGATGGAA AGTGTCTGTG CACTTCACAC CTGCTCACCG     660
```

```
ACAGCCTTCA CCTGTGCCAA TGGGCGATGT GTCCAATACT CTTACCGCTG TGATTACTAC      720

AATGACTGTG GTGATGGCAG TGATGAGGCA GGGTGCCTGT TCAGGGACTG CAATGCCACC      780

ACGGAGTTTA TGTGCAATAA CAGAAGGTGC ATACCTCGTG AGTTTATCTG CAATGGTGTA      840

GACAACTGCC ATGATAATAA CACTTCAGAT GAGAAAAATT GCCCTGATCG CACTTGCCAG      900

TCTGGATACA CAAAATGTCA TAATTCAAAT ATTTGTATTC CTCGCGTTTA TTTGTGTGAC      960

GGAGACAATG ACTGTGGAGA TAACAGTGAT GAAAACCCTA CTTATTGCAC CACTCACACA     1020

TGCAGCAGTG AGTTCCAATG CACATCTGGG NGCTGTATTC CTCAACATTG GTATTGTGAT     1080

CAAGAAACAG ATTGTTTTGA TGCCTCTCGA TGAACCTGCC TCCTTGTGGT CACTCTGAGC     1140

GAACATGCCT AGCTGATGAG TTCAAGTGTG ATGGTGGGAG GTGCATCCCA AGCGAATGGA     1200

TCTGTGACGG TGATAATGAC TGTGGGGATA TGAGTGACGA GGATAAAAGG CACCAGTGTC     1260

AGAATCAAAA CTGCTCGGAT TCCGAGTTTC TCTGTGTAAA TGACAGACCT CCGGACAGGA     1320

GTGCATTCCC CAGTCTTGGG TCTGTGATGG CGATGTGGAT TGTACTGACG GCTACATGAG     1380

AATCAGAATT GCACCAGGAG AACTTGCTCT GAAAATGAAT TCACCTGTGG TTACGGAATG     1440

TGTATCCCAA AGATATTGCG AGGTGTGACC GGCACAATGA CTGTGGTGAC TATAGCGACG     1500

AGAGGGCTGC TTATACCTAG ACTTGCCAAC AGAATCAGTT TCCTGTCAGA ACGGGCGCTG     1560

CATTAGTAAA ACCTTCGTCT GTGATGCAGG ATGAATCGAC TGTGGAGACG GATCTGATGA     1620

GCTGATGCAC CTGTGCCACA CCCCACGTGT CCACCTCACG AGTGTCAAAT ATGACAATGG     1680

GCGCTGCATC GAGATGATGA AACTCTGCAA CCACCTAGAT GACTGTTTGG ACAACAGCGA     1740

TGAGAAAGGC TGTGGCATTA ATGAATGCCA TGACCCTTCA ATCAGTGGCT GCGATCACAA     1800

CTGTATAGAC ACCTTAACCA GTTTCTATTG TTCCTGTCGT CCTGGTTACA AGCTCATGTC     1860

TGACAAGCGG ACTTGTGTTG ATATTGATGA ATGCACAGAG ATGCCTTTTG TCTGTAGCCA     1920

GAAGTGTGAG AATGTAATAG CTCCTACATC CTGTAAGTGT GCCCCAGGCT ACCTCCGAGA     1980

ACCAGATGGA AAGACCTGCC GGCAAAACAG TAACATCGAA CCCTATCTCA TTTTTAGCAA     2040

CCGTTACTAT TTGAGAAATT TAACTATAGA TGGCTATTTT TACTCCCTCA TCTTGGAAGG     2100

ACTGGACAAT GTTGTGGCAT TAGATTTTGA CCGAGTAGAG AAGAGATTGT ATTGGATTGA     2160

TACACAGAGG CAAGTCATTG AGAGAATGTT TCTGAATAAG ACAAACAAGG AGACAATCAT     2220

AAACCACAGA CTACCAGCTG CAGAAAGTCT GGCTGTAGAC TGGGTTTCCA GAAAGCTCTA     2280

CTGGTTGGAT GCCCGCCTGG ATGGCCTCTT TGTCTCTGAC CTCAATGGTG GACACCGCCG     2340

CATGCTGGCC CAGCACTGTG TGGATGCCAA CAACACCTTC TGCTTTGATA ATCCCAGAGG     2400

ACTTGCCCTT CACCCTCAAT ATGGGTACCT CTACTGGGCA GACTGGGGTC ACCGCGCATA     2460

CATTGGGAGA GTAGGCATGG ATGGAACCAA CAAGTCTGTG ATACTCCACC AAGTTAGAGT     2520

TGGCCTAATG GCATCACCAT TGATTACACC AATGATCTAC TCTACTGGGC AGATGCCACC     2580

CTGGGTTACA TAGAGTACTC TGATTTGGAG GGCCACCATC GACACACGGT GTATGATGGG     2640

GCACTGCCTC ACCCTTTCGC TATTACCATT TTTGAAGACA CTATTTATTG GACAGATTGG     2700

AATACAAGGA CAGTGGAAAA GGGAAACAAA TATGATGGAT CAAATAGACA GACACTGGTG     2760

AACACAACAC ACAGACCATT TGACATCCAT GTGTACCATC CATATAGGCA GCCCGTACCA     2820

TCCATATAGG CAGCCCATTG TGAGCAATCC CTGTGGTACC AACAATGGTG CTGTTCTCA      2880

TCTCTGCCTC ATCAAGCCAG GAGGAAAAGG GTTCACTTGC GAGTGTCCAG ATGACTTCCG     2940

CACCCTTCAA CTGAGTGGCA GCACCTACTG CATGCCCATG TGCTCCAGCA CCCAGTTCCT     3000

GTGCGCTAAC AATGAAAAGT GCATTCCTAT CTGGTGGAAA TGTGATGGAC AGAAAGACTG     3060
```

-continued

```
CTCAGATGGC TCTGATGAAC TGGCCCTTTG CCCGCAGCGC TTCTGCCGAC TGGGACAGTT    3120

CCAGTGCAGT GACGGCAACT GCACCAGCCC GCAGACTTTA TGCAATGCTC ACCAAAATTG    3180

CCCTCGATGG TCTGATGAAG ACCGTCTTCT TTGTGAGAAT CACCACTGTG ACTCCAATGA    3240

ATGGCAGTGC GCCAACAAAC GTTGCATCCC AGAATCCTGG CAGTGTGACA CATTTAACGA    3300

CTGTGAGGAT AACTCAGATG AAGACAGTTC CCACTGTGCC AGCAGGACCT GCCGGCCGGG    3360

CCAGTTTCGG TGTGCTAATG GCCGCTGCAT CCCGCAGGCC TGGAAGTGTG ATGTGGATAA    3420

TGATTGTGGA GACCACTCGG ATGAGCCCAT TGAAGAATGC ATGAGCTCTG CCCATCTCTG    3480

TGACAACTTC ACAGAATTCA GCTGCAAAAC AAATTACCGC TGCATCCCAA AGTGGGCCGT    3540

GTGCAATGGT GTAGATGACT GCAGGGACAA CAGTGATGAG CAAGGCTGTG AGGAGAGGAC    3600

ATGCCATCCT GTGGGGATT TCCGCTGTAA AACTCACCAC TGCATCCCTC TTCGTTGGCA    3660

GTGTGATGGG CAAAATGACT GTGGAGATAA CTCAGATGAG GAAAACTGTG CTCCCCGGGA    3720

GTGCACAGAG AGCGAGTTTC GATGTGTCAA TCAGCAGTGC ATTCCCTCGC GATGGATCTG    3780

TGACCATTAC AACGACTGTG GGACAACTC AGATGAACGG GACTGTGAGA TGAGGACCTG    3840

CCATCCTGAA TATTTTCAGT GTACAAGTGG ACATTGTGTA CACAGTGAAC TGAAATGCGA    3900

TGGATCCGCT GACTGTTTGG ATGCGTCTGA TGAAGCTGAT TGTCCCACAC GCTTTCCTGA    3960

TGGTGCATAC TGCCAGGCTA CTATGTTCGA ATGCAAAAAC CATGTTTGTA TCCCGCCATA    4020

TTGGAAATGT GATGGCGATG ATGACTGTGG CGATGGTTCA GATGAAGAAC TTCACCTGTG    4080

CTTGGATGTT CCCTGTAATT CACCAAACCG TTTCCGGTGT GACAACAATC GCTGCATTTA    4140

TAGTCATGAG GTGTGCAATG GTGTGGATGA CTGTGGAGAT GGAACTGATG AGACAGAGGA    4200

GCACTGTAGA AAACCGACCC CTAAACCTTG TACAGAATAT GAATATAAGT GTGGCAATGG    4260

GCATTGCATT CCACATGACA ATGTGTGTGA TGATGCCGAT GACTGTGGTG ACTGGTCCGA    4320

TGAACTGGGT TGCAATAAAG GAAAAGAAAG AACATGTGCT GAAAATATAT GCGAGCAAAA    4380

TTGTACCCAA TTAAATGAGG AGGATTTATC TGCTCCTGTA CAGCTGGGTT CGAAACCAAT    4440

GTTTTTTGAC AGAACCTCCT GTCTAGATAT CAATGAATGT GAACAATTTG GGACTTGTCC    4500

CCAGCACTGC AGAAATACCA AAGGAAGTTA TGAGTGTGTC TGTGCTGATG GCTTCACGTC    4560

TATGAGTGAC CGCCCTGGAA AACGATGTGC AGCTGAGGGT AGCTCTCCTT TGTTGCTACT    4620

GCCTGACAAT GTCCGAATTC GAAAATATAA TCTCTCATCT GAGAGGTTCT CAGAGTATCT    4680

TCAAGATGAG GAATATATCC AAGCTGTTGA TTATGATTGG GATCCCAAGG ACATAGGCCT    4740

CAGTGTTGTG TATTACACTG TGCGAGGGGA GGGCTCTAGG TTTGGTGCTA TCAAACGTGC    4800

CTACATCCCC AACTTTGAAT CCGGCCGCAA TAATCTTGTG CAGGAAGTTG ACCTGAAACT    4860

GAAATACGTA ATGCAGCCAG ATGGAATAGC AGTGGACTGG GTTGGAAGGC ATATTTACTG    4920

GTCAGATGTC AAGAATAAAC GCATTGAGGT GGCTAAACTT GATGGAAGGT ACAGAAAGTG    4980

GCTGATTTCC ACTGACCTGG ACCAACCAGC TGCTATTGCT GTGAATCCCA ACTAGGGCT    5040

TATGTTCTGG ACTGACTGGG GAAAGGAACC TAAAATCGAG TCTGCCTGGA TGAATGGAGA    5100

GGACCGCAAC ATCCTGGTTT TCGAGGACCT TGGTTGGCCA ACTGGCCTTT CTATCGATTA    5160

TTTGAACGAC CGAATCTACT GGAGTGACTT CAAGGAGGAC GTTATTGAAA CCATAAAATA    5220

TGATGGGACT GATAGGAGAG TCATTGCAAA GGAAGCAATG AACCCTTACA GCCTGGACAT    5280

CTTTGAAGAC CAGTTATACT GGATATCTAA GGAAAAGGGA AAGTATGGA AACAAAATAA    5340

ATTTGGGCAA GGAAAGAAAG AGAAAACGCT GGTAGTGAAC CCTTGGCTCA CTCAAGTTCG    5400
```

```
AATCTTTCAT CAACTCAGAT ACAATAAGTC AGTGCCCAAC CTTTGCAAAC AGATCTGCAG    5460

CCACCTCTGC CTTCTGAGAC CTGGAGGATA CAGCTGTGCC TGTCCCCAAG GCTCCAGCTT    5520

TATAGAGGGG AGCACCACTG AGTGTGATGC AGCCATCGAA CTGCCTATCA ACCTGCCCCC    5580

CCCATGCAGG TGCATGCACG GAGGAAATTG CTATTTTGAT GAGACTGACC TCCCCAAATG    5640

CAAGTGTCCT AGCGGCTACA CCGGAAAATA TTGTGAAATG GCGTTTTCAA AAGGCATCTC    5700

TCCAGGAACA ACCGCAGTAG CTGTGCTGTT GACAATCCTC TTGATCGTCG TAATTGGAGC    5760

TCTGGCAATT GCAGGATTCT TCCACTATAG AAGGACCGGC TCCCTTTTGC CTGCTCTGCC    5820

CAAGCTGCCA AGCTTAAGCA GTCTCGTCAA GCCCTCTGAA AATGGGAATG GGGTGACCTT    5880

CAGATCAGGG GCAGATCTTA ACATGGATAT TGGAGTGTCT GGTTTTGGAC CTGAGACTGC    5940

TATTGACAGG TCAATGGCAA TGAGTGAAGA CTTTGTCATG GAAATGGGGA AGCAGCCCAT    6000

AATATTTGAA AACCCAATGT ACTCAGCCAG AGACAGTGCT GTCAAAGTGG TTCAGCCAAT    6060

CCAGGTGACT GTATCTGAAA ATGTGGATAA TAAGAATTAT GGAAGTCCCA TAAACCCTTC    6120

TGAGATAGTT CCAGAGACAA ACCCAACTTC ACCAGCTGCT GATGGAACTC AGGTGACAAA    6180

ATGGAATCTC TTCAAACGAA AATCTAAACA AACTACCAAC TTTGAAAATC CAATCTATGC    6240

ACAGATGGAG AACGAGCAAA AGGAAAGTGT TGCTGCGACA CCCACCTCCAT CACCTTCGCT    6300

CCCTGCTAAG CCTAAGCCTC CTTCGAGAAG AGACCCAACT CCAACCTATT CTGCAACAGA    6360

AGACACTTTT AAAGACACCG CAAATCTTGT TAAAGAAGAC TCTGAAGTAT AG            6412
```

(2) INFORMATION FOR SEQ ID NO: 18:

(i) SEQUENCE CHARACTERISTICS:
        (A) LENGTH: 19 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 18:

```
Ala Thr Pro Pro Pro Ser Pro Ser Leu Pro Ala Lys Pro Lys Pro Pro
1               5                   10                  15

Ser Arg Arg
```

(2) INFORMATION FOR SEQ ID NO: 19:
    (i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 19:

```
Phe Glu Asn Pro Ile Tyr Ala Gln Met Glu Asn Glu
1               5                   10
```

(2) INFORMATION FOR SEQ ID NO: 20:

(i) SEQUENCE CHARACTERISTICS:

```
            (A) LENGTH: 9 amino acids
            (B) TYPE: amino acid
            (C) STRANDEDNESS:
            (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 20:

Arg Xaa Leu Pro Pro Arg Pro Xaa Xaa
1               5

(2) INFORMATION FOR SEQ ID NO: 21:

(i) SEQUENCE CHARACTERISTICS:
            (A) LENGTH: 9 amino acids
            (B) TYPE: amino acid
            (C) STRANDEDNESS:
            (D) TOPOLOGY: linear (ii) MOLECULE TYPE: peptide (iii) HYPOTHETICAL: NO (v) FRAGMENT TYPE: internal (ix) FEATURE:
            (A) NAME/KEY: Modified-site
            (B) LOCATION: 9
            (D) OTHER INFORMATION: /label= hydrophobic (xi) SEQUENCE DESCRIPTION: SEQ ID NO: 21:

Arg Xaa Leu Pro Pro Leu Pro Arg Xaa
1               5

(2) INFORMATION FOR SEQ ID NO: 22:

(i) SEQUENCE CHARACTERISTICS:
            (A) LENGTH: 11 amino acids
            (B) TYPE: amino acid
            (C) STRANDEDNESS:
            (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 22:

Pro Thr Met Pro Pro Pro Leu Pro Pro Val Pro
1               5                  10

(2) INFORMATION FOR SEQ ID NO: 23:

(i) SEQUENCE CHARACTERISTICS:
            (A) LENGTH: 11 amino acids
            (B) TYPE: amino acid
            (C) STRANDEDNESS:
            (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 23:

Pro Ala Tyr Pro Pro Pro Pro Val Pro Val Pro
```

1                  5                      10

(2) INFORMATION FOR SEQ ID NO: 24:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 24:

Glu Val Pro Val Pro Pro Pro Val Pro Pro Arg
1                  5                      10

(2) INFORMATION FOR SEQ ID NO: 25:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 25:

His Leu Asp Ser Pro Pro Ala Ile Pro Pro Arg
1                  5                      10

(2) INFORMATION FOR SEQ ID NO: 26:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 26:

His Ser Ile Ala Gly Pro Pro Val Pro Pro Arg
1                  5                      10

(2) INFORMATION FOR SEQ ID NO: 27:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 27:

```
Ala Pro Ala Val Pro Pro Ala Arg Pro Gly Ser
1               5                   10
```

(2) INFORMATION FOR SEQ ID NO: 28:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 28:

```
Gly Ala Pro Pro Val Pro Ser Arg Pro Gly Ala
1               5                   10
```

(2) INFORMATION FOR SEQ ID NO: 29:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 29:

```
Pro Pro Arg Pro Leu Pro Val Ala Pro Gly Ser
1               5                   10
```

(2) INFORMATION FOR SEQ ID NO: 30:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 30:

```
Pro Ala Pro Ala Leu Pro Pro Lys Pro Pro Lys
1               5                   10
```

(2) INFORMATION FOR SEQ ID NO: 31:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 31:

```
Ala Pro Lys Pro Met Pro Pro Arg Pro Pro Leu
1               5                   10
```

(2) INFORMATION FOR SEQ ID NO: 32:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 32:

```
Pro Pro Thr Pro Pro Pro Leu Pro Pro Pro Leu
1               5                   10
```

(2) INFORMATION FOR SEQ ID NO: 33:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 33:

```
Pro Ala Leu Pro Pro Pro Pro Arg Pro Val Pro
1               5                   10
```

(2) INFORMATION FOR SEQ ID NO: 34:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 34:

```
Arg Pro Arg Pro Leu Pro Pro Leu Pro Pro Thr
1               5                   10
```

(2) INFORMATION FOR SEQ ID NO: 35:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 35:

Gly Val Arg Pro Leu Pro Pro Leu Pro Asp Pro
1               5                   10

(2) INFORMATION FOR SEQ ID NO: 36:

(i) SEQUENCE CHARACTERISTICS:
         (A) LENGTH: 11 amino acids
         (B) TYPE: amino acid
         (C) STRANDEDNESS:
         (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 36:

Pro Pro Arg Pro Leu Pro Pro Arg Pro Pro Ala
1               5                   10

(2) INFORMATION FOR SEQ ID NO: 37:

(i) SEQUENCE CHARACTERISTICS:
         (A) LENGTH: 7 amino acids
         (B) TYPE: amino acid
         (C) STRANDEDNESS:
         (D) TOPOLOGY: linear (ii) MOLECULE TYPE: peptide (iii) HYPOTHETICAL: NO (v) FRAGMENT TYPE: internal (ix) FEATURE:
         (A) NAME/KEY: Modified-site
         (B) LOCATION: 3
         (D) OTHER INFORMATION: /label= hydrophobic (xi) SEQUENCE DESCRIPTION: SEQ ID NO: 37:

Xaa Pro Xaa Pro Pro Xaa Pro
1               5

(2) INFORMATION FOR SEQ ID NO: 38:

(i) SEQUENCE CHARACTERISTICS:
         (A) LENGTH: 22 amino acids
         (B) TYPE: amino acid
         (C) STRANDEDNESS:
         (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 38:

Glu Ser Asp Gly Gly Tyr Met Asp Met Ser Lys Asp Glu Ser Val Asp
1               5                   10                  15

Tyr Val Pro Met Leu Asp
            20

(2) INFORMATION FOR SEQ ID NO: 39:

(i) SEQUENCE CHARACTERISTICS:
         (A) LENGTH: 18 amino acids
         (B) TYPE: amino acid (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 39:

Glu Glu Glu Glu Glu Tyr Met Pro Met Glu Asp Leu Tyr Leu Asp Ile
1               5                  10                  15
Leu Pro (2) INFORMATION FOR SEQ ID NO: 40:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 40:

Gln Gly Val Asp Thr Tyr Val Glu Met Arg Pro
1               5                  10

(2) INFORMATION FOR SEQ ID NO: 41:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 41:

Asp Ser Thr Asn Glu Tyr Met Asp Met Lys Pro
1               5                  10

(2) INFORMATION FOR SEQ ID NO: 42:

(i) SEQUENCE CHARACTERISTICS:
        (A) LENGTH: 24 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 42:

Gly Pro Gly Gly Asp Tyr Ala Ala Met Gly Ala Cys Pro Ala Ser Glu
1               5                  10                  15
Gln Gly Tyr Glu Glu Met Arg Ala
            20

(2) INFORMATION FOR SEQ ID NO: 43:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 43:

```
Thr Pro Asp Glu Asp Tyr Glu Tyr Met Asn Arg Gln Arg Asp Gly Gly
  1               5                  10                  15

Gly Pro Gly Gly Asp Tyr Ala Ala Met Gly Ala
             20                  25
```

(2) INFORMATION FOR SEQ ID NO: 44:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 44:

```
Cys Thr Ile Asp Val Tyr Met Val Met Val Lys
  1               5                  10
```

(2) INFORMATION FOR SEQ ID NO: 45:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 45:

```
Ser Pro Ser Ser Gly Tyr Met Pro Met Asn Gln
  1               5                  10
```

(2) INFORMATION FOR SEQ ID NO: 46:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 46:

```
Asp Glu Asp Glu Glu Tyr Glu Tyr Met Asn Arg
1               5                   10
```

(2) INFORMATION FOR SEQ ID NO: 47:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 47:

```
Leu Glu Glu Leu Gly Tyr Glu Tyr Met Asp Val
1               5                   10
```

(2) INFORMATION FOR SEQ ID NO: 48:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 48:

```
Glu Glu Leu Ser Asn Tyr Ile Cys Met Gly Gly
1               5                   10
```

(2) INFORMATION FOR SEQ ID NO: 49:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 49:

```
Val Ser Ile Glu Glu Tyr Thr Glu Met Met Pro
1               5                   10
```

(2) INFORMATION FOR SEQ ID NO: 50:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal

```
    (xi) SEQUENCE DESCRIPTION: SEQ ID NO: 50:

His Thr Asp Asp Gly Tyr Met Pro Met Ser Pro
1               5                   10

(2) INFORMATION FOR SEQ ID NO: 51:

(i) SEQUENCE CHARACTERISTICS:
         (A) LENGTH: 11 amino acids
         (B) TYPE: amino acid
         (C) STRANDEDNESS:
         (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 51:

Lys Gly Asn Gly Asp Tyr Met Pro Met Ser Pro
1               5                   10

(2) INFORMATION FOR SEQ ID NO: 52:

(i) SEQUENCE CHARACTERISTICS:
         (A) LENGTH: 11 amino acids
         (B) TYPE: amino acid
         (C) STRANDEDNESS:
         (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 52:

Val Asp Pro Asn Gly Tyr Met Met Met Ser Pro
1               5                   10

(2) INFORMATION FOR SEQ ID NO: 53:

(i) SEQUENCE CHARACTERISTICS:
         (A) LENGTH: 11 amino acids
         (B) TYPE: amino acid
         (C) STRANDEDNESS:
         (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 53:

Pro Cys Thr Gly Asp Tyr Met Asn Met Ser Pro
1               5                   10

(2) INFORMATION FOR SEQ ID NO: 54:

(i) SEQUENCE CHARACTERISTICS:
         (A) LENGTH: 11 amino acids
         (B) TYPE: amino acid
         (C) STRANDEDNESS:
         (D) TOPOLOGY: linear (ii) MOLECULE TYPE: peptide (iii) HYPOTHETICAL: NO (v) FRAGMENT TYPE: internal
```

(xi) SEQUENCE DESCRIPTION: SEQ ID NO: 54:

Thr Gly Ser Glu Glu Tyr Met Asn Met Asp Leu
1               5                   10

(2) INFORMATION FOR SEQ ID NO: 55:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 55:

Asn Ser Arg Gly Asp Tyr Met Thr Met Gln Ile
1               5                   10

(2) INFORMATION FOR SEQ ID NO: 56:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 56:

Val Ala Pro Val Ser Tyr Ala Asp Met Arg Thr
1               5                   10

(2) INFORMATION FOR SEQ ID NO: 57:

(i) SEQUENCE CHARACTERISTICS:
        (A) LENGTH: 21 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 57:

Glu Arg Glu Asn Glu Tyr Met Pro Met Ala Pro Gln Ile His Leu Tyr
1               5                   10                  15
Ser Gln Ile Arg Glu
            20

(2) INFORMATION FOR SEQ ID NO: 58:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 58:

Leu Ser Asn Pro Thr Tyr Ser Val Met Arg Ser
1               5                  10

(2) INFORMATION FOR SEQ ID NO: 59:

(i) SEQUENCE CHARACTERISTICS:
          (A) LENGTH: 11 amino acids
          (B) TYPE: amino acid
          (C) STRANDEDNESS:
          (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 59:

Cys Pro Glu Lys Val Tyr Glu Leu Met Arg Ala
1               5                  10

(2) INFORMATION FOR SEQ ID NO: 60:

(i) SEQUENCE CHARACTERISTICS:
          (A) LENGTH: 21 amino acids
          (B) TYPE: amino acid
          (C) STRANDEDNESS:
          (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 60:

Asn Thr Thr Val Asp Tyr Val Tyr Met Ser His Gly Asp Asn Gly Asp
1               5                  10                  15

Tyr Val Tyr Met Asn
            20

(2) INFORMATION FOR SEQ ID NO: 61:

(i) SEQUENCE CHARACTERISTICS:
          (A) LENGTH: 21 amino acids
          (B) TYPE: amino acid
          (C) STRANDEDNESS:
          (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 61:

Asn Cys Asn Asp Asp Tyr Val Thr Met His Tyr Thr Thr Asp Gly Asp
1               5                  10                  15

Tyr Ile Tyr Met Asn
            20

(2) INFORMATION FOR SEQ ID NO: 62:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 62:

Tyr Val Asn Asp Ile Tyr Leu Tyr Met Arg His Leu Glu Arg Glu Phe
1               5                  10                  15

Lys Val Arg Thr Asp Tyr Met Ala Met Gln Glu
            20                  25

(2) INFORMATION FOR SEQ ID NO: 63:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 63:

Asn Gln Glu Glu Ala Tyr Val Thr Met Ser Ser
1               5                  10

(2) INFORMATION FOR SEQ ID NO: 64:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 64:

Phe Ile Ala Ser Lys Tyr Glu Asp Met Tyr Pro
1               5                  10

(2) INFORMATION FOR SEQ ID NO: 65:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 65:

Leu Gly Ser Gln Ser Tyr Glu Asp Met Arg Gly
1               5                  10

(2) INFORMATION FOR SEQ ID NO: 66:

(i) SEQUENCE CHARACTERISTICS:
       (A) LENGTH: 11 amino acids
       (B) TYPE: amino acid
       (C) STRANDEDNESS:
       (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 66:

Glu Asp Ala Asp Ser Tyr Glu Asn Met Asp Lys
1               5                   10

(2) INFORMATION FOR SEQ ID NO: 67:

(i) SEQUENCE CHARACTERISTICS:
       (A) LENGTH: 11 amino acids
       (B) TYPE: amino acid
       (C) STRANDEDNESS:
       (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 67:

Glu Leu Gln Asp Asp Tyr Glu Asp Met Met Glu
1               5                   10

(2) INFORMATION FOR SEQ ID NO: 68:

(i) SEQUENCE CHARACTERISTICS:
       (A) LENGTH: 11 amino acids
       (B) TYPE: amino acid
       (C) STRANDEDNESS:
       (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 68:

Ala Ala Cys Val Val Tyr Glu Asp Met Ser His
1               5                   10

(2) INFORMATION FOR SEQ ID NO: 69:

(i) SEQUENCE CHARACTERISTICS:
       (A) LENGTH: 11 amino acids
       (B) TYPE: amino acid
       (C) STRANDEDNESS:
       (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 69:

Ala Pro Pro Glu Glu Tyr Val Pro Met Val Lys

```
1               5                    10
```

(2) INFORMATION FOR SEQ ID NO: 70:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 70:

```
Ile Asp Ser Cys Thr Tyr Glu Ala Met Tyr Asn
1               5                    10
```

(2) INFORMATION FOR SEQ ID NO: 71:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 71:

```
Val Ala Val Ala Glu Tyr Glu Ile Met Glu Gln
1               5                    10
```

(2) INFORMATION FOR SEQ ID NO: 72:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 72:

```
Met Ser Val Glu Ser Tyr Glu Glu Met Lys Met
1               5                    10
```

(2) INFORMATION FOR SEQ ID NO: 73:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 73:

```
His Gln Thr Arg Glu Tyr Glu Ser Met Ile Glu
1               5                   10
```

(2) INFORMATION FOR SEQ ID NO: 74:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 74:

```
Thr Leu Gln Asn Glu Tyr Glu Leu Met Arg Glu
1               5                   10
```

(2) INFORMATION FOR SEQ ID NO: 75:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 75:

```
Gly Gly Glu Glu Ile Tyr Val Val Met Leu Gly
1               5                   10
```

(2) INFORMATION FOR SEQ ID NO: 76:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 76:

```
Leu Glu Gly Glu His Tyr Ile Asn Met Ala Val
1               5                   10
```

(2) INFORMATION FOR SEQ ID NO: 77:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 77:

Glu Ile Thr Glu Gln Tyr Ile Tyr Met Val Met
1               5                   10

(2) INFORMATION FOR SEQ ID NO: 78:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 78:

Thr Glu Gln Tyr Ile Tyr Met Val Met Glu Cys
1               5                   10

(2) INFORMATION FOR SEQ ID NO: 79:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 79:

Leu Pro Ala Lys Pro
1               5

(2) INFORMATION FOR SEQ ID NO: 80:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 80:

Leu Pro Ala Leu Pro
1               5

(2) INFORMATION FOR SEQ ID NO: 81:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 81:

Leu Pro Lys Leu Pro
1               5

(2) INFORMATION FOR SEQ ID NO: 82:

(i) SEQUENCE CHARACTERISTICS:
            (A) LENGTH: 11 amino acids
            (B) TYPE: amino acid
            (C) STRANDEDNESS:
            (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 82:

Glu Asn Pro Ile Tyr Ala Gln Met Glu Asn Glu
1               5                   10

(2) INFORMATION FOR SEQ ID NO: 83:

(i) SEQUENCE CHARACTERISTICS:
            (A) LENGTH: 14083 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (ix) FEATURE:
            (A) NAME/KEY: CDS
            (B) LOCATION: 107..14071

(xi) SEQUENCE DESCRIPTION: SEQ ID NO: 83:

```
TTGCAGACCT AAAGGAGCGT TCGCTAGCAG AGGCGCTGCC GGTGCGGTGT GCTACGCGCG         60

CCCACCTCCC GGGGAAGGAA CGGCGAGGCC GGGGACCGTC GCGGAG ATG GAT CGC          115
                                               Met Asp Arg
                                                   1

GGG CCG GCA GCA GTG GCG TGC ACG CTG CTC CTG GCT CTC GTC GCC TGC         163
Gly Pro Ala Ala Val Ala Cys Thr Leu Leu Leu Ala Leu Val Ala Cys
      5                  10                  15

CTA GCG CCG GCC AGT GGC CAA GAA TGT GAC AGT GCG CAT TTT CGC TGT         211
Leu Ala Pro Ala Ser Gly Gln Glu Cys Asp Ser Ala His Phe Arg Cys
 20                  25                  30                  35

GGA AGT GGG CAT TGC ATC CCT GCA GAC TGG AGG TGT GAT GGG ACC AAA         259
Gly Ser Gly His Cys Ile Pro Ala Asp Trp Arg Cys Asp Gly Thr Lys
                 40                  45                  50

GAC TGT TCA GAT GAC GCG GAT GAA ATT GGC TGC GCT GTT GTG ACC TGC         307
Asp Cys Ser Asp Asp Ala Asp Glu Ile Gly Cys Ala Val Val Thr Cys
             55                  60                  65

CAG CAG GGC TAT TTC AAG TGC CAG AGT GAG GGA CAA TGC ATC CCC AGC         355
Gln Gln Gly Tyr Phe Lys Cys Gln Ser Glu Gly Gln Cys Ile Pro Ser
         70                  75                  80

TCC TGG GTG TGT GAC CAA GAT CAA GAC TGT GAT GAT GGC TCA GAT GAA         403
Ser Trp Val Cys Asp Gln Asp Gln Asp Cys Asp Asp Gly Ser Asp Glu
     85                  90                  95

CGT CAA GAT TGC TCA CAA AGT ACA TGC TCA AGT CAT CAG ATA ACA TGC         451
Arg Gln Asp Cys Ser Gln Ser Thr Cys Ser Ser His Gln Ile Thr Cys
100                 105                 110                 115
```

```
TCC AAT GGT CAG TGT ATC CCA AGT GAA TAC AGG TGC GAC CAC GTC AGA        499
Ser Asn Gly Gln Cys Ile Pro Ser Glu Tyr Arg Cys Asp His Val Arg
            120                 125                 130

GAC TGC CCC GAT GGA GCT GAT GAG AAT GAC TGC CAG TAC CCA ACA TGT        547
Asp Cys Pro Asp Gly Ala Asp Glu Asn Asp Cys Gln Tyr Pro Thr Cys
            135                 140                 145

GAG CAG CTT ACT TGT GAC AAT GGG GCC TGC TAT AAC ACC AGT CAG AAG        595
Glu Gln Leu Thr Cys Asp Asn Gly Ala Cys Tyr Asn Thr Ser Gln Lys
            150                 155                 160

TGT GAT TGG AAA GTT GAT TGC AGG GAC TCC TCA GAT GAA ATC AAC TGC        643
Cys Asp Trp Lys Val Asp Cys Arg Asp Ser Ser Asp Glu Ile Asn Cys
165                 170                 175

ACT GAG ATA TGC TTG CAC AAT GAG TTT TCA TGT GGC AAT GGA GAG TGT        691
Thr Glu Ile Cys Leu His Asn Glu Phe Ser Cys Gly Asn Gly Glu Cys
180                 185                 190                 195

ATC CCT CGT GCT TAT GTC TGT GAC CAT GAC AAT GAT TGC CAA GAC GGC        739
Ile Pro Arg Ala Tyr Val Cys Asp His Asp Asn Asp Cys Gln Asp Gly
            200                 205                 210

AGT GAT GAA CAT GCT TGC AAC TAT CCG ACC TGC GGT GGT TAC CAG TTC        787
Ser Asp Glu His Ala Cys Asn Tyr Pro Thr Cys Gly Gly Tyr Gln Phe
            215                 220                 225

ACT TGC CCC AGT GGC CGA TGC ATT TAT CAA AAC TGG GTT TGT GAT GGA        835
Thr Cys Pro Ser Gly Arg Cys Ile Tyr Gln Asn Trp Val Cys Asp Gly
            230                 235                 240

GAA GAT GAC TGT AAA GAT AAT GGA GAT GAA GAT GGA TGT GAA AGC GGT        883
Glu Asp Asp Cys Lys Asp Asn Gly Asp Glu Asp Gly Cys Glu Ser Gly
            245                 250                 255

CCT CAT GAT GTT CAT AAA TGT TCC CCA AGA GAA TGG TCT TGC CCA GAG        931
Pro His Asp Val His Lys Cys Ser Pro Arg Glu Trp Ser Cys Pro Glu
260                 265                 270                 275

TCG GGA CGA TGC ATC TCC ATT TAT AAA GTT TGT GAT GGG ATT TTA GAT        979
Ser Gly Arg Cys Ile Ser Ile Tyr Lys Val Cys Asp Gly Ile Leu Asp
            280                 285                 290

TGC CCA GGA AGA GAA GAT GAA AAC AAC ACT AGT ACC GGA AAA TAC TGT       1027
Cys Pro Gly Arg Glu Asp Glu Asn Asn Thr Ser Thr Gly Lys Tyr Cys
            295                 300                 305

AGT ATG ACT CTG TGC TCT GCC TTG AAC TGC CAG TAC CAG TGC CAT GAG       1075
Ser Met Thr Leu Cys Ser Ala Leu Asn Cys Gln Tyr Gln Cys His Glu
            310                 315                 320

ACG CCG TAT GGA GGA GCG TGT TTT TGT CCC CCA GGT TAT ATC ATC AAC       1123
Thr Pro Tyr Gly Gly Ala Cys Phe Cys Pro Pro Gly Tyr Ile Ile Asn
            325                 330                 335

CAC AAT GAC AGC CGT ACC TGT GTT GAG TTT GAT GAT TGC CAG ATA TGG       1171
His Asn Asp Ser Arg Thr Cys Val Glu Phe Asp Asp Cys Gln Ile Trp
340                 345                 350                 355

GGA ATT TGT GAC CAG AAG TGT GAA AGC CGA CCT GGC CGT CAC CTG TGC       1219
Gly Ile Cys Asp Gln Lys Cys Glu Ser Arg Pro Gly Arg His Leu Cys
            360                 365                 370

CAC TGT GAA GAA GGG TAT ATC TTG GAG CGT GGA CAG TAT TGC AAA GCT       1267
His Cys Glu Glu Gly Tyr Ile Leu Glu Arg Gly Gln Tyr Cys Lys Ala
            375                 380                 385

AAT GAT TCC TTT GGC GAG GCC TCC ATT ATC TTC TCC AAT GGT CGG GAT       1315
Asn Asp Ser Phe Gly Glu Ala Ser Ile Ile Phe Ser Asn Gly Arg Asp
            390                 395                 400

TTG TTA ATT GGT GAT ATT CAT GGA AGG AGC TTC CGG ATC CTA GTG GAG       1363
Leu Leu Ile Gly Asp Ile His Gly Arg Ser Phe Arg Ile Leu Val Glu
            405                 410                 415

TCT CAG AAT CGT GGA GTG GCC GTG GGT GTG GCT TTC CAC TAT CAC CTG       1411
Ser Gln Asn Arg Gly Val Ala Val Gly Val Ala Phe His Tyr His Leu
```

```
            420                   425                   430                   435
CAA AGA GTT TTT TGG ACA GAC ACC GTG CAA AAT AAG GTT TTT TCA GTT                   1459
Gln Arg Val Phe Trp Thr Asp Thr Val Gln Asn Lys Val Phe Ser Val
                440                   445                   450

GAC ATT AAT GGT TTA AAT ATC CAA GAG GTT CTC AAT GTT TCT GTT GAA                   1507
Asp Ile Asn Gly Leu Asn Ile Gln Glu Val Leu Asn Val Ser Val Glu
                455                   460                   465

ACC CCA GAG AAC CTG GCT GTG GAC TGG GTT AAT AAT AAA ATC TAT CTA                   1555
Thr Pro Glu Asn Leu Ala Val Asp Trp Val Asn Asn Lys Ile Tyr Leu
                470                   475                   480

GTG GAA ACC AAG GTC AAC CGC ATA GAT ATG GTA AAT TTG GAT GGA AGC                   1603
Val Glu Thr Lys Val Asn Arg Ile Asp Met Val Asn Leu Asp Gly Ser
                485                   490                   495

TAT CGG GTT ACC CTT ATA ACT GAA AAC TTG GGG CAT CCT AGA GGA ATT                   1651
Tyr Arg Val Thr Leu Ile Thr Glu Asn Leu Gly His Pro Arg Gly Ile
500                   505                   510                   515

GCC GTG GAC CCA ACT GTT GGT TAT TTA TTT TTC TCA GAT TGG GAG AGC                   1699
Ala Val Asp Pro Thr Val Gly Tyr Leu Phe Phe Ser Asp Trp Glu Ser
                520                   525                   530

CTT TCT GGG GAA CCT AAG CTG GAA AGG GCA TTC ATG GAT GGC AGC AAC                   1747
Leu Ser Gly Glu Pro Lys Leu Glu Arg Ala Phe Met Asp Gly Ser Asn
                535                   540                   545

CGT AAA GAC TTG GTG AAA ACA AAG CTG GGA TGG CCT GCT GGG GTA ACT                   1795
Arg Lys Asp Leu Val Lys Thr Lys Leu Gly Trp Pro Ala Gly Val Thr
                550                   555                   560

CTG GAT ATG ATA TCG AAG CGT GTT TAC TGG GTT GAC TCT CGG TTT GAT                   1843
Leu Asp Met Ile Ser Lys Arg Val Tyr Trp Val Asp Ser Arg Phe Asp
565                   570                   575

TAC ATT GAA ACT GTA ACT TAT GAT GGA ATT CAA AGG AAG ACT GTA GTT                   1891
Tyr Ile Glu Thr Val Thr Tyr Asp Gly Ile Gln Arg Lys Thr Val Val
580                   585                   590                   595

CAT GGA GGC TCC CTC ATT CCT CAT CCC TTT GGA GTA AGC TTA TTT GAA                   1939
His Gly Gly Ser Leu Ile Pro His Pro Phe Gly Val Ser Leu Phe Glu
                600                   605                   610

GGT CAG GTG TTC TTT ACA GAT TGG ACA AAG ATG GCC GTG CTG AAG GCA                   1987
Gly Gln Val Phe Phe Thr Asp Trp Thr Lys Met Ala Val Leu Lys Ala
                615                   620                   625

AAC AAG TTC ACA GAG ACC AAC CCA CAA GTG TAC TAC CAG GCT TCC CTG                   2035
Asn Lys Phe Thr Glu Thr Asn Pro Gln Val Tyr Tyr Gln Ala Ser Leu
                630                   635                   640

AGG CCC TAT GGA GTG ACT GTT TAC CAT TCC CTC AGA CAG CCC TAT GCT                   2083
Arg Pro Tyr Gly Val Thr Val Tyr His Ser Leu Arg Gln Pro Tyr Ala
                645                   650                   655

ACC AAT CCG TGT AAA GAT AAC AAT GGG GGC TGT GAG CAG GTC TGT GTT                   2131
Thr Asn Pro Cys Lys Asp Asn Asn Gly Gly Cys Glu Gln Val Cys Val
660                   665                   670                   675

CTC AGC CAC AGA ACA GAT AAT GAT GGT TTG GGT TTC CGT TGC AAG TGC                   2179
Leu Ser His Arg Thr Asp Asn Asp Gly Leu Gly Phe Arg Cys Lys Cys
                680                   685                   690

ACA TTC GGC TTC CAA CTG GAT ACA GAT GAG CGC CAC TGC ATT GCT GTT                   2227
Thr Phe Gly Phe Gln Leu Asp Thr Asp Glu Arg His Cys Ile Ala Val
                695                   700                   705

CAG AAT TTC CTC ATT TTT TCA TCC CAA GTT GCT ATT CGT GGG ATC CCG                   2275
Gln Asn Phe Leu Ile Phe Ser Ser Gln Val Ala Ile Arg Gly Ile Pro
                710                   715                   720

TTC ACC TTG TCT ACC CAG GAA GAT GTC ATG GTT CCA GTT TCG GGG AAT                   2323
Phe Thr Leu Ser Thr Gln Glu Asp Val Met Val Pro Val Ser Gly Asn
                725                   730                   735

CCT TCT TTC TTT GTC GGG ATT GAT TTT GAC GCC CAG GAC AGC ACT ATC                   2371
```

```
Pro Ser Phe Phe Val Gly Ile Asp Phe Asp Ala Gln Asp Ser Thr Ile
740                 745                 750                 755

TTT TTT TCA GAT ATG TCA AAA CAC ATG ATT TTT AAG CAA AAG ATT GAT    2419
Phe Phe Ser Asp Met Ser Lys His Met Ile Phe Lys Gln Lys Ile Asp
                760                 765                 770

GGC ACA GGA AGA GAA ATT CTC GCA GCT AAC AGG GTG GAA AAT GTT GAA    2467
Gly Thr Gly Arg Glu Ile Leu Ala Ala Asn Arg Val Glu Asn Val Glu
            775                 780                 785

AGT TTG GCT TTT GAT TGG ATT TCA AAG AAT CTC TAT TGG ACA GAC TCT    2515
Ser Leu Ala Phe Asp Trp Ile Ser Lys Asn Leu Tyr Trp Thr Asp Ser
            790                 795                 800

CAT TAC AAG AGT ATC AGT GTC ATG AGG CTA GCT GAT AAA ACG AGA CGC    2563
His Tyr Lys Ser Ile Ser Val Met Arg Leu Ala Asp Lys Thr Arg Arg
        805                 810                 815

ACA GTA GTT CAG TAT TTA AAT AAC CCA CGG TCG GTG GTA GTT CAT CCT    2611
Thr Val Val Gln Tyr Leu Asn Asn Pro Arg Ser Val Val Val His Pro
820                 825                 830                 835

TTT GCC GGG TAT CTA TTC TTC ACT GAT TGG TTC CGT CCT GCT AAA ATT    2659
Phe Ala Gly Tyr Leu Phe Phe Thr Asp Trp Phe Arg Pro Ala Lys Ile
                840                 845                 850

ATG AGA GCA TGG AGT GAC GGA TCT CAC CTC TTG CCT GTA ATA AAC ACT    2707
Met Arg Ala Trp Ser Asp Gly Ser His Leu Leu Pro Val Ile Asn Thr
            855                 860                 865

ACT CTT GGA TGG CCC AAT GGC TTG GCC ATC GAT TGG GCT GCT TCA CGA    2755
Thr Leu Gly Trp Pro Asn Gly Leu Ala Ile Asp Trp Ala Ala Ser Arg
            870                 875                 880

TTG TAC TGG GTA GAT GCC TAT TTT GAT AAA ATT GAG CAC AGC ACC TTT    2803
Leu Tyr Trp Val Asp Ala Tyr Phe Asp Lys Ile Glu His Ser Thr Phe
        885                 890                 895

GAT GGT TTA GAC AGA AGA AGA CTG GGC CAT ATA GAG CAG ATG ACA CAT    2851
Asp Gly Leu Asp Arg Arg Arg Leu Gly His Ile Glu Gln Met Thr His
900                 905                 910                 915

CCG TTT GGA CTT GCC ATC TTT GGA GAG CAT TTA TTT TTT ACT GAC TGG    2899
Pro Phe Gly Leu Ala Ile Phe Gly Glu His Leu Phe Phe Thr Asp Trp
                920                 925                 930

AGA CTG GGT GCC ATT ATT CGA GTC AGG AAA GCA GAT GGT GGA GAA ATG    2947
Arg Leu Gly Ala Ile Ile Arg Val Arg Lys Ala Asp Gly Gly Glu Met
            935                 940                 945

ACA GTT ATC CGA AGT GGC ATT GCT TAC ATA CTG CAT TTG AAA TCG TAT    2995
Thr Val Ile Arg Ser Gly Ile Ala Tyr Ile Leu His Leu Lys Ser Tyr
            950                 955                 960

GAT GTC AAC ATC CAG ACT GGT TCT AAC GCC TGT AAT CAA CCC ACG CAT    3043
Asp Val Asn Ile Gln Thr Gly Ser Asn Ala Cys Asn Gln Pro Thr His
        965                 970                 975

CCT AAC GGT GAC TGC AGC CAC TTC TGC TTC CCG GTG CCA AAT TTC CAG    3091
Pro Asn Gly Asp Cys Ser His Phe Cys Phe Pro Val Pro Asn Phe Gln
980                 985                 990                 995

CGA GTG TGT GGG TGC CCT TAT GGA ATG AGG CTG GCT TCC AAT CAC TTG    3139
Arg Val Cys Gly Cys Pro Tyr Gly Met Arg Leu Ala Ser Asn His Leu
                1000                1005                1010

ACA TGC GAG GGG GAC CCA ACC AAT GAA CCA CCC ACG GAG CAG TGT GGC    3187
Thr Cys Glu Gly Asp Pro Thr Asn Glu Pro Pro Thr Glu Gln Cys Gly
            1015                1020                1025

TTA TTT TCC TTC CCC TGT AAA AAT GGC AGA TGT GTG CCC AAT TAC TAT    3235
Leu Phe Ser Phe Pro Cys Lys Asn Gly Arg Cys Val Pro Asn Tyr Tyr
            1030                1035                1040

CTC TGT GAT GGA GTC GAT GAT TGT CAT GAT AAC AGT GAT GAG CAA CTA    3283
Leu Cys Asp Gly Val Asp Asp Cys His Asp Asn Ser Asp Glu Gln Leu
        1045                1050                1055
```

```
                                   -continued

TGT GGC ACA CTT AAT AAT ACC TGT TCA TCT TCG GCG TTC ACC TGT GGC          3331
Cys Gly Thr Leu Asn Asn Thr Cys Ser Ser Ser Ala Phe Thr Cys Gly
1060                1065                1070                1075

CAT GGG GAG TGC ATT CCT GCA CAC TGG CGC TGT GAC AAA CGC AAC GAC          3379
His Gly Glu Cys Ile Pro Ala His Trp Arg Cys Asp Lys Arg Asn Asp
                1080                1085                1090

TGT GTG GAT GGC AGT GAT GAG CAC AAC TGC CCC ACC CAC GCA CCT GCT          3427
Cys Val Asp Gly Ser Asp Glu His Asn Cys Pro Thr His Ala Pro Ala
            1095                1100                1105

TCC TGC CTT GAC ACC CAA TAC ACC TGT GAT AAT CAC CAG TGT ATC TCA          3475
Ser Cys Leu Asp Thr Gln Tyr Thr Cys Asp Asn His Gln Cys Ile Ser
        1110                1115                1120

AAG AAC TGG GTC TGT GAC ACA GAC AAT GAT TGT GGG GAT GGA TCT GAT          3523
Lys Asn Trp Val Cys Asp Thr Asp Asn Asp Cys Gly Asp Gly Ser Asp
    1125                1130                1135

GAA AAG AAC TGC AAT TCG ACA GAG ACA TGC CAA CCT AGT CAG TTT AAT          3571
Glu Lys Asn Cys Asn Ser Thr Glu Thr Cys Gln Pro Ser Gln Phe Asn
1140                1145                1150                1155

TGC CCC AAT CAT CGA TGT ATT GAC CTA TCG TTT GTC TGT GAT GGT GAC          3619
Cys Pro Asn His Arg Cys Ile Asp Leu Ser Phe Val Cys Asp Gly Asp
                1160                1165                1170

AAG GAT TGT GTT GAT GGA TCT GAT GAG GTT GGT TGT GTA TTA AAC TGT          3667
Lys Asp Cys Val Asp Gly Ser Asp Glu Val Gly Cys Val Leu Asn Cys
            1175                1180                1185

ACT GCT TCT CAA TTC AAG TGT GCC AGT GGG GAT AAA TGT ATT GGC GTC          3715
Thr Ala Ser Gln Phe Lys Cys Ala Ser Gly Asp Lys Cys Ile Gly Val
        1190                1195                1200

ACA AAT CGT TGT GAT GGT GTT TTT GAT TGC AGT GAC AAC TCG GAT GAA          3763
Thr Asn Arg Cys Asp Gly Val Phe Asp Cys Ser Asp Asn Ser Asp Glu
    1205                1210                1215

GCG GGC TGT CCA ACC AGG CCT CCT GGT ATG TGC CAC TCA GAT GAA TTT          3811
Ala Gly Cys Pro Thr Arg Pro Pro Gly Met Cys His Ser Asp Glu Phe
1220                1225                1230                1235

CAG TGC CAA GAA GAT GGT ATC TGC ATC CCG AAC TTC TGG GAA TGT GAT          3859
Gln Cys Gln Glu Asp Gly Ile Cys Ile Pro Asn Phe Trp Glu Cys Asp
                1240                1245                1250

GGG CAT CCA GAC TGC CTC TAT GGA TCT GAT GAG CAC AAT GCC TGT GTC          3907
Gly His Pro Asp Cys Leu Tyr Gly Ser Asp Glu His Asn Ala Cys Val
            1255                1260                1265

CCC AAG ACT TGC CCT TCA TCA TAT TTC CAC TGT GAC AAC GGA AAC TGC          3955
Pro Lys Thr Cys Pro Ser Ser Tyr Phe His Cys Asp Asn Gly Asn Cys
        1270                1275                1280

ATC CAC AGG GCA TGG CTC TGT GAT CGG GAC AAT GAC TGC GGG GAT ATG          4003
Ile His Arg Ala Trp Leu Cys Asp Arg Asp Asn Asp Cys Gly Asp Met
    1285                1290                1295

AGT GAT GAG AAG GAC TGC CCT ACT CAG CCC TTT CGC TGT CCT AGT TGG          4051
Ser Asp Glu Lys Asp Cys Pro Thr Gln Pro Phe Arg Cys Pro Ser Trp
1300                1305                1310                1315

CAA TGG CAG TGT CTT GGC CAT AAC ATC TGT GTG AAT CTG AGT GTA GTG          4099
Gln Trp Gln Cys Leu Gly His Asn Ile Cys Val Asn Leu Ser Val Val
                1320                1325                1330

TGT GAT GGC ATC TTT GAC TGC CCC AAT GGG ACA GAT GAG TCC CCA CTT          4147
Cys Asp Gly Ile Phe Asp Cys Pro Asn Gly Thr Asp Glu Ser Pro Leu
            1335                1340                1345

TGC AAT GGG AAC AGC TGC TCA GAT TTC AAT GGT GGT TGT ACT CAC GAG          4195
Cys Asn Gly Asn Ser Cys Ser Asp Phe Asn Gly Gly Cys Thr His Glu
        1350                1355                1360

TGT GTT CAA GAG CCC TTT GGG GCT AAA TGC CTA TGT CCA TTG GGA TTC          4243
Cys Val Gln Glu Pro Phe Gly Ala Lys Cys Leu Cys Pro Leu Gly Phe
    1365                1370                1375
```

-continued

| | |
|---|---|
| TTA CTT GCC AAT GAT TCT AAG ACC TGT GAA GAC ATA GAT GAA TGT GAT<br>Leu Leu Ala Asn Asp Ser Lys Thr Cys Glu Asp Ile Asp Glu Cys Asp<br>1380                            1385                    1390                      1395 | 4291 |
| ATT CTA GGC TCT TGT AGC CAG CAC TGT TAC AAT ATG AGA GGT TCT TTC<br>Ile Leu Gly Ser Cys Ser Gln His Cys Tyr Asn Met Arg Gly Ser Phe<br>                    1400                    1405                    1410 | 4339 |
| CGG TGC TCG TGT GAT ACA GGC TAC ATG TTA GAA AGT GAT GGG AGG ACT<br>Arg Cys Ser Cys Asp Thr Gly Tyr Met Leu Glu Ser Asp Gly Arg Thr<br>                  1415                  1420                  1425 | 4387 |
| TGC AAA GTT ACA GCA TCT GAG AGT CTG CTG TTA CTT GTG GCA AGT CAG<br>Cys Lys Val Thr Ala Ser Glu Ser Leu Leu Leu Val Ala Ser Gln<br>1430                            1435                    1440 | 4435 |
| AAC AAA ATT ATT GCC GAC AGT GTC ACC TCC CAG GTC CAC AAT ATC TAT<br>Asn Lys Ile Ile Ala Asp Ser Val Thr Ser Gln Val His Asn Ile Tyr<br>                    1445                    1450                    1455 | 4483 |
| TCA TTG GTC GAG AAT GGT TCT TAC ATT GTA GCT GTT GAT TTT GAT TCA<br>Ser Leu Val Glu Asn Gly Ser Tyr Ile Val Ala Val Asp Phe Asp Ser<br>1460                            1465                    1470                    1475 | 4531 |
| ATT AGT GGT CGT ATC TTT TGG TCT GAT GCA ACT CAG GGT AAA ACC TGG<br>Ile Ser Gly Arg Ile Phe Trp Ser Asp Ala Thr Gln Gly Lys Thr Trp<br>                    1480                    1485                    1490 | 4579 |
| AGT GCG TTT CAA AAT GGA ACG GAC AGA AGA GTG GTA TTT GAC AGT AGC<br>Ser Ala Phe Gln Asn Gly Thr Asp Arg Arg Val Val Phe Asp Ser Ser<br>                  1495                    1500                    1505 | 4627 |
| ATC ATC TTG ACT GAA ACT ATT GCA ATA GAT TGG GTA GGT CGT AAT CTT<br>Ile Ile Leu Thr Glu Thr Ile Ala Ile Asp Trp Val Gly Arg Asn Leu<br>                    1510                    1515                    1520 | 4675 |
| TAC TGG ACA GAC TAT GCT CTG GAA ACA ATT GAA GTC TCC AAA ATT GAT<br>Tyr Trp Thr Asp Tyr Ala Leu Glu Thr Ile Glu Val Ser Lys Ile Asp<br>                1525                    1530                    1535 | 4723 |
| GGG AGC CAC AGG ACT GTG CTG ATT AGT AAA AAC CTA ACA AAT CCA AGA<br>Gly Ser His Arg Thr Val Leu Ile Ser Lys Asn Leu Thr Asn Pro Arg<br>1540                            1545                    1550                    1555 | 4771 |
| GGA CTA GCA TTA GAT CCC AGA ATG AAT GAG CAT CTA CTG TTC TGG TCT<br>Gly Leu Ala Leu Asp Pro Arg Met Asn Glu His Leu Leu Phe Trp Ser<br>                    1560                    1565                    1570 | 4819 |
| GAC TGG GGC CAC CAC CCT CGC ATC GAG CGA GCC AGC ATG GAC GGC AGC<br>Asp Trp Gly His His Pro Arg Ile Glu Arg Ala Ser Met Asp Gly Ser<br>                1575                    1580                    1585 | 4867 |
| ATG CGC ACT GTC ATT GTC CAG GAC AAG ATC TTC TGG CCC TGC GGC TTA<br>Met Arg Thr Val Ile Val Gln Asp Lys Ile Phe Trp Pro Cys Gly Leu<br>                    1590                    1595                    1600 | 4915 |
| ACT ATT GAC TAC CCC AAC AGA CTG CTC TAC TTC ATG GAC TCC TAT CTT<br>Thr Ile Asp Tyr Pro Asn Arg Leu Leu Tyr Phe Met Asp Ser Tyr Leu<br>1605                            1610                    1615 | 4963 |
| GAT TAC ATG GAC TTT TGC GAT TAT AAT GGA CAC CAT CGG AGA CAG GTG<br>Asp Tyr Met Asp Phe Cys Asp Tyr Asn Gly His His Arg Arg Gln Val<br>1620                            1625                    1630                    1635 | 5011 |
| ATA GCC AGT GAT TTG ATT ATA CGG CAC CCC TAT GCC CTA ACT CTC TTT<br>Ile Ala Ser Asp Leu Ile Ile Arg His Pro Tyr Ala Leu Thr Leu Phe<br>                    1640                    1645                    1650 | 5059 |
| GAA GAC TCT GTG TAC TGG ACT GAC CGT GCT ACT CGT CGG GTT ATG CGA<br>Glu Asp Ser Val Tyr Trp Thr Asp Arg Ala Thr Arg Arg Val Met Arg<br>                    1655                    1660                    1665 | 5107 |
| GCC AAC AAG TGG CAT GGA GGG AAC CAG TCA GTT GTA ATG TAT AAT ATT<br>Ala Asn Lys Trp His Gly Gly Asn Gln Ser Val Val Met Tyr Asn Ile<br>                    1670                    1675                    1680 | 5155 |
| CAA TGG CCC CTT GGG ATT GTT GCG GTT CAT CCT TCG AAA CAA CCA AAT<br>Gln Trp Pro Leu Gly Ile Val Ala Val His Pro Ser Lys Gln Pro Asn | 5203 |

```
                1685                1690                1695
TCC GTG AAT CCA TGT GCC TTT TCC CGC TGC AGC CAT CTC TGC CTG CTT         5251
Ser Val Asn Pro Cys Ala Phe Ser Arg Cys Ser His Leu Cys Leu Leu
1700            1705                1710                1715

TCC TCA CAG GGG CCT CAT TTT TAC TCC TGT GTT TGT CCT TCA GGA TGG         5299
Ser Ser Gln Gly Pro His Phe Tyr Ser Cys Val Cys Pro Ser Gly Trp
        1720                1725                1730

AGT CTG TCT CCT GAT CTC CTG AAT TGC TTG AGA GAT GAT CAA CCT TTC         5347
Ser Leu Ser Pro Asp Leu Leu Asn Cys Leu Arg Asp Asp Gln Pro Phe
            1735                1740                1745

TTA ATA ACT GTA AGG CAA CAT ATA ATT TTT GGA ATC TCC CTT AAT CCT         5395
Leu Ile Thr Val Arg Gln His Ile Ile Phe Gly Ile Ser Leu Asn Pro
                1750                1755                1760

GAG GTG AAG AGC AAT GAT GCT ATG GTC CCC ATA GCA GGG ATA CAG AAT         5443
Glu Val Lys Ser Asn Asp Ala Met Val Pro Ile Ala Gly Ile Gln Asn
        1765                1770                1775

GGT TTA GAT GTT GAA TTT GAT GAT GCT GAG CAA TAC ATC TAT TGG GTT         5491
Gly Leu Asp Val Glu Phe Asp Asp Ala Glu Gln Tyr Ile Tyr Trp Val
1780            1785                1790                1795

GAA AAT CCA GGT GAA ATT CAC AGA GTG AAG ACA GAT GGC ACC AAC AGG         5539
Glu Asn Pro Gly Glu Ile His Arg Val Lys Thr Asp Gly Thr Asn Arg
            1800                1805                1810

ACA GTA TTT GCT TCT ATA TCT ATG GTG GGG CCT TCT ATG AAC CTG GCC         5587
Thr Val Phe Ala Ser Ile Ser Met Val Gly Pro Ser Met Asn Leu Ala
        1815                1820                1825

TTA GAT TGG ATT TCA AGA AAC CTT TAT TCT ACC AAT CCT AGA ACT CAG         5635
Leu Asp Trp Ile Ser Arg Asn Leu Tyr Ser Thr Asn Pro Arg Thr Gln
            1830                1835                1840

TCA ATC GAG GTT TTG ACA CTC CAC GGA GAT ATC AGA TAC AGA AAA ACA         5683
Ser Ile Glu Val Leu Thr Leu His Gly Asp Ile Arg Tyr Arg Lys Thr
1845            1850                1855

TTG ATT GCC AAT GAT GGG ACA GCT CTT GGA GTT GGC TTT CCA ATT GGC         5731
Leu Ile Ala Asn Asp Gly Thr Ala Leu Gly Val Gly Phe Pro Ile Gly
1860                1865                1870                1875

ATA ACT GTT GAT CCT GCT CGT GGG AAG CTG TAC TGG TCA GAC CAA GGA         5779
Ile Thr Val Asp Pro Ala Arg Gly Lys Leu Tyr Trp Ser Asp Gln Gly
                1880                1885                1890

ACT GAC AGT GGG GTT CCT GCC AAG ATC GCC AGT GCT AAC ATG GAT GGC         5827
Thr Asp Ser Gly Val Pro Ala Lys Ile Ala Ser Ala Asn Met Asp Gly
        1895                1900                1905

ACA TCT GTG AAA ACT CTC TTT ACT GGG AAC CTC GAA CAC CTG GAG TGT         5875
Thr Ser Val Lys Thr Leu Phe Thr Gly Asn Leu Glu His Leu Glu Cys
            1910                1915                1920

GTC ACT CTT GAC ATC GAA GAG CAG AAA CTC TAC TGG GCA GTC ACT GGA         5923
Val Thr Leu Asp Ile Glu Glu Gln Lys Leu Tyr Trp Ala Val Thr Gly
        1925                1930                1935

AGA GGA GTG ATT GAA AGA GGA AAC GTG GAT GGA ACA GAT CGG ATG ATC         5971
Arg Gly Val Ile Glu Arg Gly Asn Val Asp Gly Thr Asp Arg Met Ile
1940                1945                1950                1955

CTG GTA CAC CAG CTT TCC CAC CCC TGG GGA ATT GCA GTC CAT GAT TCT         6019
Leu Val His Gln Leu Ser His Pro Trp Gly Ile Ala Val His Asp Ser
            1960                1965                1970

TTC CTT TAT TAT ACT GAT GAA CAG TAT GAG GTC ATT GAA AGA GTT GAT         6067
Phe Leu Tyr Tyr Thr Asp Glu Gln Tyr Glu Val Ile Glu Arg Val Asp
                1975                1980                1985

AAG GCC ACT GGG GCC AAC AAA ATA GTC TTG AGA GAT AAT GTT CCA AAT         6115
Lys Ala Thr Gly Ala Asn Lys Ile Val Leu Arg Asp Asn Val Pro Asn
        1990                1995                2000

CTG AGG GGT CTT CAA GTT TAT CAC AGA CGC AAT GCC GCC GAA TCC TCA         6163
```

-continued

```
Leu Arg Gly Leu Gln Val Tyr His Arg Arg Asn Ala Ala Glu Ser Ser
    2005                2010                2015

AAT GGC TGT AGC AAC AAC ATG AAT GCC TGT CAG CAG ATT TGC CTG CCT     6211
Asn Gly Cys Ser Asn Asn Met Asn Ala Cys Gln Gln Ile Cys Leu Pro
2020                2025                2030                2035

GTA CCA GGA GGA TTG TTT TCC TGC GCC TGT GCC ACT GGA TTT AAA CTC     6259
Val Pro Gly Gly Leu Phe Ser Cys Ala Cys Ala Thr Gly Phe Lys Leu
                2040                2045                2050

AAT CCT GAT AAT CGG TCC TGC TCT CCA TAT AAC TCT TTC ATT GTT GTT     6307
Asn Pro Asp Asn Arg Ser Cys Ser Pro Tyr Asn Ser Phe Ile Val Val
                2055                2060                2065

TCA ATG CTG TCT GCA ATC AGA GGC TTT AGC TTG GAA TTG TCA GAT CAT     6355
Ser Met Leu Ser Ala Ile Arg Gly Phe Ser Leu Glu Leu Ser Asp His
            2070                2075                2080

TCA GAA ACC ATG GTG CCG GTG GCA GGC CAA GGA CGA AAC GCA CTG CAT     6403
Ser Glu Thr Met Val Pro Val Ala Gly Gln Gly Arg Asn Ala Leu His
            2085                2090                2095

GTG GAT GTG GAT GTG TCC TCT GGC TTT ATT TAT TGG TGT GAT TTT AGC     6451
Val Asp Val Asp Val Ser Ser Gly Phe Ile Tyr Trp Cys Asp Phe Ser
2100                2105                2110                2115

AGC TCA GTG GCA TCT GAT AAT GCG ATC CGT AGA ATT AAA CCA GAT GGA     6499
Ser Ser Val Ala Ser Asp Asn Ala Ile Arg Arg Ile Lys Pro Asp Gly
                2120                2125                2130

TCT TCT CTG ATG AAC ATT GTG ACA CAT GGA ATA GGA GAA AAT GGA GTC     6547
Ser Ser Leu Met Asn Ile Val Thr His Gly Ile Gly Glu Asn Gly Val
                2135                2140                2145

CGG GGT ATT GCA GTG GAT TGG GTA GCA GGA AAT CTT TAT TTC ACC AAT     6595
Arg Gly Ile Ala Val Asp Trp Val Ala Gly Asn Leu Tyr Phe Thr Asn
                2150                2155                2160

GCC TTT GTT TCT GAA ACA CTG ATA GAA GTT CTG CGG ATC AAT ACT ACT     6643
Ala Phe Val Ser Glu Thr Leu Ile Glu Val Leu Arg Ile Asn Thr Thr
            2165                2170                2175

TAC CGC CGT GTT CTT CTT AAA GTC ACA GTG GAC ATG CCT AGG CAT ATT     6691
Tyr Arg Arg Val Leu Leu Lys Val Thr Val Asp Met Pro Arg His Ile
2180                2185                2190                2195

GTT GTA GAT CCC AAG AAC AGA TAC CTC TTC TGG GCT GAC TAT GGG CAG     6739
Val Val Asp Pro Lys Asn Arg Tyr Leu Phe Trp Ala Asp Tyr Gly Gln
                2200                2205                2210

AGA CCA AAG ATT GAG CGT TCT TTC CTT GAC TGT ACC AAT CGA ACA GTG     6787
Arg Pro Lys Ile Glu Arg Ser Phe Leu Asp Cys Thr Asn Arg Thr Val
                2215                2220                2225

CTT GTG TCA GAG GGC ATT GTC ACA CCA CGG GGC TTG GCA GTG GAC CGA     6835
Leu Val Ser Glu Gly Ile Val Thr Pro Arg Gly Leu Ala Val Asp Arg
            2230                2235                2240

AGT GAT GGC TAC GTT TAT TGG GTT GAT GAT TCT TTA GAT ATA ATT GCA     6883
Ser Asp Gly Tyr Val Tyr Trp Val Asp Asp Ser Leu Asp Ile Ile Ala
            2245                2250                2255

AGG ATT CGT ATC AAT GGA GAG AAC TCT GAA GTG ATT CGT TAT GGC AGT     6931
Arg Ile Arg Ile Asn Gly Glu Asn Ser Glu Val Ile Arg Tyr Gly Ser
2260                2265                2270                2275

CGT TAC CCA ACT CCT TAT GGC ATC ACT GTT TTT GAA AAT TCT ATC ATA     6979
Arg Tyr Pro Thr Pro Tyr Gly Ile Thr Val Phe Glu Asn Ser Ile Ile
                2280                2285                2290

TGG GTA GAT AGG AAT TTG AAA AAG ATC TTC CAA GCC AGC AAG GAA CCA     7027
Trp Val Asp Arg Asn Leu Lys Lys Ile Phe Gln Ala Ser Lys Glu Pro
                2295                2300                2305

GAG AAC ACA GAG CCA CCC ACA GTG ATA AGA GAC AAT ATC AAC TGG CTA     7075
Glu Asn Thr Glu Pro Pro Thr Val Ile Arg Asp Asn Ile Asn Trp Leu
            2310                2315                2320
```

```
AGA GAT GTG ACC ATC TTT GAC AAG CAA GTC CAG CCC CGG TCA CCA GCA      7123
Arg Asp Val Thr Ile Phe Asp Lys Gln Val Gln Pro Arg Ser Pro Ala
        2325                2330                2335

GAG GTC AAC AAC AAC CCT TGC TTG GAA AAC AAT GGT GGG TGC TCT CAT      7171
Glu Val Asn Asn Asn Pro Cys Leu Glu Asn Asn Gly Gly Cys Ser His
2340                2345                2350                2355

CTC TGC TTT GCT CTG CCT GGA TTG CAC ACC CCA AAA TGT GAC TGT GCC      7219
Leu Cys Phe Ala Leu Pro Gly Leu His Thr Pro Lys Cys Asp Cys Ala
            2360                2365                2370

TTT GGG ACC CTG CAA AGT GAT GGC AAG AAT TGT GCC ATT TCA ACA GAA      7267
Phe Gly Thr Leu Gln Ser Asp Gly Lys Asn Cys Ala Ile Ser Thr Glu
        2375                2380                2385

AAT TTC CTC ATC TTT GCC TTG TCT AAT TCC TTG AGA AGC TTA CAC TTG      7315
Asn Phe Leu Ile Phe Ala Leu Ser Asn Ser Leu Arg Ser Leu His Leu
            2390                2395                2400

GAC CCT GAA AAC CAT AGC CCA CCT TTC CAA ACA ATA AAT GTG GAA AGA      7363
Asp Pro Glu Asn His Ser Pro Pro Phe Gln Thr Ile Asn Val Glu Arg
        2405                2410                2415

ACT GTC ATG TCT CTA GAC TAT GAC AGT GTA AGT GAT AGA ATC TAC TTC      7411
Thr Val Met Ser Leu Asp Tyr Asp Ser Val Ser Asp Arg Ile Tyr Phe
2420                2425                2430                2435

ACA CAA AAT TTA GCC TCT GGA GTT GGA CAG ATT TCC TAT GCC ACC CTG      7459
Thr Gln Asn Leu Ala Ser Gly Val Gly Gln Ile Ser Tyr Ala Thr Leu
            2440                2445                2450

TCT TCA GGG ATC CAT ACT CCA ACT GTC ATT GCT TCA GGT ATA GGG ACT      7507
Ser Ser Gly Ile His Thr Pro Thr Val Ile Ala Ser Gly Ile Gly Thr
        2455                2460                2465

GCT GAT GGC ATT GCC TTT GAC TGG ATT ACT AGA AGA ATT TAT TAC AGT      7555
Ala Asp Gly Ile Ala Phe Asp Trp Ile Thr Arg Arg Ile Tyr Tyr Ser
        2470                2475                2480

GAC TAC CTC AAC CAG ATG ATT AAT TCC ATG GCT GAA GAT GGG TCT AAC      7603
Asp Tyr Leu Asn Gln Met Ile Asn Ser Met Ala Glu Asp Gly Ser Asn
        2485                2490                2495

CGC ACT GTG ATA GCC CGC GTT CCA AAA CCA AGA GCA ATT GTG TTA GAT      7651
Arg Thr Val Ile Ala Arg Val Pro Lys Pro Arg Ala Ile Val Leu Asp
2500                2505                2510                2515

CCC TGC CAA GGG TAC CTG TAC TGG GCT GAC TGG GAT ACA CAT GCC AAA      7699
Pro Cys Gln Gly Tyr Leu Tyr Trp Ala Asp Trp Asp Thr His Ala Lys
            2520                2525                2530

ATC GAG AGA GCC ACA TTG GGA GGA AAC TTC CGG GTA CCC ATT GTG AAC      7747
Ile Glu Arg Ala Thr Leu Gly Gly Asn Phe Arg Val Pro Ile Val Asn
        2535                2540                2545

AGC AGT CTG GTC ATG CCC AGT GGG CTG ACT CTG GAC TAT GAA GAG GAC      7795
Ser Ser Leu Val Met Pro Ser Gly Leu Thr Leu Asp Tyr Glu Glu Asp
        2550                2555                2560

CTT CTC TAC TGG GTG GAT GCT AGT CTG CAG AGG ATT GAA CGC AGC ACT      7843
Leu Leu Tyr Trp Val Asp Ala Ser Leu Gln Arg Ile Glu Arg Ser Thr
        2565                2570                2575

CTG ACG GGC GTG GAT CGT GAA GTC ATT GTC AAT GCA GCC GTT CAT GCT      7891
Leu Thr Gly Val Asp Arg Glu Val Ile Val Asn Ala Ala Val His Ala
2580                2585                2590                2595

TTT GGC TTG ACT CTC TAT GGC CAG TAT ATT TAC TGG ACT GAC TTG TAC      7939
Phe Gly Leu Thr Leu Tyr Gly Gln Tyr Ile Tyr Trp Thr Asp Leu Tyr
            2600                2605                2610

ACA CAA AGA ATT TAC CGA GCT AAC AAA TAT GAC GGG TCA GGT CAG ATT      7987
Thr Gln Arg Ile Tyr Arg Ala Asn Lys Tyr Asp Gly Ser Gly Gln Ile
        2615                2620                2625

GCA ATG ACC ACA AAT TTG CTC TCC CAG CCC AGG GGA ATC AAC ACT GTT      8035
Ala Met Thr Thr Asn Leu Leu Ser Gln Pro Arg Gly Ile Asn Thr Val
        2630                2635                2640
```

```
GTG AAG AAC CAG AAA CAA CAG TGT AAC AAT CCT TGT GAA CAG TTT AAT      8083
Val Lys Asn Gln Lys Gln Gln Cys Asn Asn Pro Cys Glu Gln Phe Asn
        2645            2650                2655

GGG GGC TGC AGC CAT ATC TGT GCA CCA GGT CCA AAT GGT GCC GAG TGC      8131
Gly Gly Cys Ser His Ile Cys Ala Pro Gly Pro Asn Gly Ala Glu Cys
2660            2665                2670                2675

CAG TGT CCA CAT GAG GGC AAC TGG TAT TTG GCC AAC AAC AGG AAG CAC      8179
Gln Cys Pro His Glu Gly Asn Trp Tyr Leu Ala Asn Asn Arg Lys His
            2680                2685                2690

TGC ATT GTG GAC AAT GGT GAA CGA TGT GGT GCA TCT TCC TTC ACC TGC      8227
Cys Ile Val Asp Asn Gly Glu Arg Cys Gly Ala Ser Ser Phe Thr Cys
                2695                2700                2705

TCC AAT GGG CGC TGC ATC TCG GAA GAG TGG AAG TGT GAT AAT GAC AAC      8275
Ser Asn Gly Arg Cys Ile Ser Glu Glu Trp Lys Cys Asp Asn Asp Asn
            2710                2715                2720

GAC TGT GGG GAT GGC AGT GAT GAG ATG GAA AGT GTC TGT GCA CTT CAC      8323
Asp Cys Gly Asp Gly Ser Asp Glu Met Glu Ser Val Cys Ala Leu His
        2725                2730                2735

ACC TGC TCA CCG ACA GCC TTC ACC TGT GCC AAT GGG CGA TGT GTC CAA      8371
Thr Cys Ser Pro Thr Ala Phe Thr Cys Ala Asn Gly Arg Cys Val Gln
2740                2745                2750                2755

TAC TCT TAC CGC TGT GAT TAC TAC AAT GAC TGT GGT GAT GGC AGT GAT      8419
Tyr Ser Tyr Arg Cys Asp Tyr Tyr Asn Asp Cys Gly Asp Gly Ser Asp
            2760                2765                2770

GAG GCA GGG TGC CTG TTC AGG GAC TGC AAT GCC ACC ACG GAG TTT ATG      8467
Glu Ala Gly Cys Leu Phe Arg Asp Cys Asn Ala Thr Thr Glu Phe Met
                2775                2780                2785

TGC AAT AAC AGA AGG TGC ATA CCT CGT GAG TTT ATC TGC AAT GGT GTA      8515
Cys Asn Asn Arg Arg Cys Ile Pro Arg Glu Phe Ile Cys Asn Gly Val
            2790                2795                2800

GAC AAC TGC CAT GAT AAT AAC ACT TCA GAT GAG AAA AAT TGC CCT GAT      8563
Asp Asn Cys His Asp Asn Asn Thr Ser Asp Glu Lys Asn Cys Pro Asp
        2805                2810                2815

CGC ACT TGC CAG TCT GGA TAC ACA AAA TGT CAT AAT TCA AAT ATT TGT      8611
Arg Thr Cys Gln Ser Gly Tyr Thr Lys Cys His Asn Ser Asn Ile Cys
2820                2825                2830                2835

ATT CCT CGC GTT TAT TTG TGT GAC GGA GAC AAT GAC TGT GGA GAT AAC      8659
Ile Pro Arg Val Tyr Leu Cys Asp Gly Asp Asn Asp Cys Gly Asp Asn
            2840                2845                2850

AGT GAT GAA AAC CCT ACT TAT TGC ACC ACT CAC ACA TGC AGC AGC AGT      8707
Ser Asp Glu Asn Pro Thr Tyr Cys Thr Thr His Thr Cys Ser Ser Ser
        2855                2860                2865

GAG TTC CAA TGC GCA TCT GGG CGC TGT ATT CCT CAA CAT TGG TAT TGT      8755
Glu Phe Gln Cys Ala Ser Gly Arg Cys Ile Pro Gln His Trp Tyr Cys
            2870                2875                2880

GAT CAA GAA ACA GAT TGT TTT GAT GCC TCT GAT GAA CCT GCC TCT TGT      8803
Asp Gln Glu Thr Asp Cys Phe Asp Ala Ser Asp Glu Pro Ala Ser Cys
        2885                2890                2895

GGT CAC TCT GAG CGA ACA TGC CTA GCT GAT GAG TTC AAG TGT GAT GGT      8851
Gly His Ser Glu Arg Thr Cys Leu Ala Asp Glu Phe Lys Cys Asp Gly
2900                2905                2910                2915

GGG AGG TGC ATC CCA AGC GAA TGG ATC TGT GAC GGT GAT AAT GAC TGT      8899
Gly Arg Cys Ile Pro Ser Glu Trp Ile Cys Asp Gly Asp Asn Asp Cys
            2920                2925                2930

GGG GAT ATG AGT GAC GAG GAT AAA AGG CAC CAG TGT CAG AAT CAA AAC      8947
Gly Asp Met Ser Asp Glu Asp Lys Arg His Gln Cys Gln Asn Gln Asn
        2935                2940                2945

TGC TCG GAT TCC GAG TTT CTC TGT GTA AAT GAC AGA CCT CCG GAC AGG      8995
Cys Ser Asp Ser Glu Phe Leu Cys Val Asn Asp Arg Pro Pro Asp Arg
```

```
                  2950                2955                2960
AGG TGC ATT CCC CAG TCT TGG GTC TGT GAT GGC GAT GTG GAT TGT ACT      9043
Arg Cys Ile Pro Gln Ser Trp Val Cys Asp Gly Asp Val Asp Cys Thr
        2965                2970                2975

GAC GGC TAC GAT GAG AAT CAG AAT TGC ACC AGG AGA ACT TGC TCT GAA      9091
Asp Gly Tyr Asp Glu Asn Gln Asn Cys Thr Arg Arg Thr Cys Ser Glu
2980                2985                2990                2995

AAT GAA TTC ACC TGT GGT TAC GGA CTG TGT ATC CCA AAG ATA TTC AGG      9139
Asn Glu Phe Thr Cys Gly Tyr Gly Leu Cys Ile Pro Lys Ile Phe Arg
                3000                3005                3010

TGT GAC CGG CAC AAT GAC TGT GGT GAC TAT AGC GAC GAG AGG GGC TGC      9187
Cys Asp Arg His Asn Asp Cys Gly Asp Tyr Ser Asp Glu Arg Gly Cys
        3015                3020                3025

TTA TAC CAG ACT TGC CAA CAG AAT CAG TTT ACC TGT CAG AAC GGG CGC      9235
Leu Tyr Gln Thr Cys Gln Gln Asn Gln Phe Thr Cys Gln Asn Gly Arg
                3030                3035                3040

TGC ATT AGT AAA ACC TTC GTC TGT GAT GAG GAT AAT GAC TGT GGA GAC      9283
Cys Ile Ser Lys Thr Phe Val Cys Asp Glu Asp Asn Asp Cys Gly Asp
        3045                3050                3055

GGA TCT GAT GAG CTG ATG CAC CTG TGC CAC ACC CCA GAA CCC ACG TGT      9331
Gly Ser Asp Glu Leu Met His Leu Cys His Thr Pro Glu Pro Thr Cys
3060                3065                3070                3075

CCA CCT CAC GAG TTC AAG TGT GAC AAT GGG CGC TGC ATC GAG ATG ATG      9379
Pro Pro His Glu Phe Lys Cys Asp Asn Gly Arg Cys Ile Glu Met Met
                3080                3085                3090

AAA CTC TGC AAC CAC CTA GAT GAC TGT TTG GAC AAC AGC GAT GAG AAA      9427
Lys Leu Cys Asn His Leu Asp Asp Cys Leu Asp Asn Ser Asp Glu Lys
        3095                3100                3105

GGC TGT GGC ATT AAT GAA TGC CAT GAC CCT TCA ATC AGT GGC TGC GAT      9475
Gly Cys Gly Ile Asn Glu Cys His Asp Pro Ser Ile Ser Gly Cys Asp
        3110                3115                3120

CAC AAC TGC ACA GAC ACC TTA ACC AGT TTC TAT TGT TCC TGT CGT CCT      9523
His Asn Cys Thr Asp Thr Leu Thr Ser Phe Tyr Cys Ser Cys Arg Pro
        3125                3130                3135

GGT TAC AAG CTC ATG TCT GAC AAG CGG ACT TGT GTT GAT ATT GAT GAA      9571
Gly Tyr Lys Leu Met Ser Asp Lys Arg Thr Cys Val Asp Ile Asp Glu
3140                3145                3150                3155

TGC ACA GAG ATG CCT TTT GTC TGT AGC CAG AAG TGT GAG AAT GTA ATA      9619
Cys Thr Glu Met Pro Phe Val Cys Ser Gln Lys Cys Glu Asn Val Ile
                3160                3165                3170

GGC TCC TAC ATC TGT AAG TGT GCC CCA GGC TAC CTC CGA GAA CCA GAT      9667
Gly Ser Tyr Ile Cys Lys Cys Ala Pro Gly Tyr Leu Arg Glu Pro Asp
        3175                3180                3185

GGA AAG ACC TGC CGG CAA AAC AGT AAC ATC GAA CCC TAT CTC ATT TTT      9715
Gly Lys Thr Cys Arg Gln Asn Ser Asn Ile Glu Pro Tyr Leu Ile Phe
        3190                3195                3200

AGC AAC CGT TAC TAT TTG AGA AAT TTA ACT ATA GAT GGC TAT TTT TAC      9763
Ser Asn Arg Tyr Tyr Leu Arg Asn Leu Thr Ile Asp Gly Tyr Phe Tyr
        3205                3210                3215

TCC CTC ATC TTG GAA GGA CTG GAC AAT GTT GTG GCA TTA GAT TTT GAC      9811
Ser Leu Ile Leu Glu Gly Leu Asp Asn Val Val Ala Leu Asp Phe Asp
3220                3225                3230                3235

CGA GTA GAG AAG AGA TTG TAT TGG ATT GAT ACA CAG AGG CAA GTC ATT      9859
Arg Val Glu Lys Arg Leu Tyr Trp Ile Asp Thr Gln Arg Gln Val Ile
                3240                3245                3250

GAG AGA ATG TTT CTG AAT AAG ACA AAC AAG GAG ACA ATC ATA AAC CAC      9907
Glu Arg Met Phe Leu Asn Lys Thr Asn Lys Glu Thr Ile Ile Asn His
                3255                3260                3265

AGA CTA CCA GCT GCA GAA AGT CTG GCT GTA GAC TGG GTT TCC AGA AAG      9955
```

```
Arg Leu Pro Ala Ala Glu Ser Leu Ala Val Asp Trp Val Ser Arg Lys
            3270                3275                3280

CTC TAC TGG TTG GAT GCC CGC CTG GAT GGC CTC TTT GTC TCT GAC CTC    10003
Leu Tyr Trp Leu Asp Ala Arg Leu Asp Gly Leu Phe Val Ser Asp Leu
        3285                3290                3295

AAT GGT GGA CAC CGC CGC ATG CTG GCC CAG CAC TGT GTG GAT GCC AAC    10051
Asn Gly Gly His Arg Arg Met Leu Ala Gln His Cys Val Asp Ala Asn
3300                3305                3310                3315

AAC ACC TTC TGC TTT GAT AAT CCC AGA GGA CTT GCC CTT CAC CCT CAA    10099
Asn Thr Phe Cys Phe Asp Asn Pro Arg Gly Leu Ala Leu His Pro Gln
            3320                3325                3330

TAT GGG TAC CTC TAC TGG GCA GAC TGG GGT CAC CGC GCA TAC ATT GGG    10147
Tyr Gly Tyr Leu Tyr Trp Ala Asp Trp Gly His Arg Ala Tyr Ile Gly
        3335                3340                3345

AGA GTA GGC ATG GAT GGA ACC AAC AAG TCT GTG ATA ATC TCC ACC AAG    10195
Arg Val Gly Met Asp Gly Thr Asn Lys Ser Val Ile Ile Ser Thr Lys
        3350                3355                3360

TTA GAG TGG CCT AAT GGC ATC ACC ATT GAT TAC ACC AAT GAT CTA CTC    10243
Leu Glu Trp Pro Asn Gly Ile Thr Ile Asp Tyr Thr Asn Asp Leu Leu
        3365                3370                3375

TAC TGG GCA GAT GCC CAC CTG GGT TAC ATA GAG TAC TCT GAT TTG GAG    10291
Tyr Trp Ala Asp Ala His Leu Gly Tyr Ile Glu Tyr Ser Asp Leu Glu
3380                3385                3390                3395

GGC CAC CAT CGA CAC ACG GTG TAT GAT GGG GCA CTG CCT CAC CCT TTC    10339
Gly His His Arg His Thr Val Tyr Asp Gly Ala Leu Pro His Pro Phe
            3400                3405                3410

GCT ATT ACC ATT TTT GAA GAC ACT ATT TAT TGG ACA GAT TGG AAT ACA    10387
Ala Ile Thr Ile Phe Glu Asp Thr Ile Tyr Trp Thr Asp Trp Asn Thr
        3415                3420                3425

AGG ACA GTG GAA AAG GGA AAC AAA TAT GAT GGA TCA AAT AGA CAG ACA    10435
Arg Thr Val Glu Lys Gly Asn Lys Tyr Asp Gly Ser Asn Arg Gln Thr
        3430                3435                3440

CTG GTG AAC ACA ACA CAC AGA CCA TTT GAC ATC CAT GTG TAC CAT CCA    10483
Leu Val Asn Thr Thr His Arg Pro Phe Asp Ile His Val Tyr His Pro
        3445                3450                3455

TAT AGG CAG CCC ATT GTG AGC AAT CCC TGT GGT ACC AAC AAT GGT GGC    10531
Tyr Arg Gln Pro Ile Val Ser Asn Pro Cys Gly Thr Asn Asn Gly Gly
3460                3465                3470                3475

TGT TCT CAT CTC TGC CTC ATC AAG CCA GGA GGA AAA GGG TTC ACT TGC    10579
Cys Ser His Leu Cys Leu Ile Lys Pro Gly Gly Lys Gly Phe Thr Cys
            3480                3485                3490

GAG TGT CCA GAT GAC TTC CGC ACC CTT CAA CTG AGT GGC AGC ACC TAC    10627
Glu Cys Pro Asp Asp Phe Arg Thr Leu Gln Leu Ser Gly Ser Thr Tyr
        3495                3500                3505

TGC ATG CCC ATG TGC TCC AGC ACC CAG TTC CTG TGC GCT AAC AAT GAA    10675
Cys Met Pro Met Cys Ser Ser Thr Gln Phe Leu Cys Ala Asn Asn Glu
        3510                3515                3520

AAG TGC ATT CCT ATC TGG TGG AAA TGT GAT GGA CAG AAA GAC TGC TCA    10723
Lys Cys Ile Pro Ile Trp Trp Lys Cys Asp Gly Gln Lys Asp Cys Ser
        3525                3530                3535

GAT GGC TCT GAT GAA CTG GCC CTT TGC CCG CAG CGC TTC TGC CGA CTG    10771
Asp Gly Ser Asp Glu Leu Ala Leu Cys Pro Gln Arg Phe Cys Arg Leu
3540                3545                3550                3555

GGA CAG TTC CAG TGC AGT GAC GGC AAC TGC ACC AGC CCG CAG ACT TTA    10819
Gly Gln Phe Gln Cys Ser Asp Gly Asn Cys Thr Ser Pro Gln Thr Leu
            3560                3565                3570

TGC AAT GCT CAC CAA AAT TGC CCT GAT GGG TCT GAT GAA GAC CGT CTT    10867
Cys Asn Ala His Gln Asn Cys Pro Asp Gly Ser Asp Glu Asp Arg Leu
        3575                3580                3585
```

```
CTT TGT GAG AAT CAC CAC TGT GAC TCC AAT GAA TGG CAG TGC GCC AAC           10915
Leu Cys Glu Asn His His Cys Asp Ser Asn Glu Trp Gln Cys Ala Asn
        3590                3595                3600

AAA CGT TGC ATC CCA GAA TCC TGG CAG TGT GAC ACA TTT AAC GAC TGT           10963
Lys Arg Cys Ile Pro Glu Ser Trp Gln Cys Asp Thr Phe Asn Asp Cys
        3605                3610                3615

GAG GAT AAC TCA GAT GAA GAC AGT TCC CAC TGT GCC AGC AGG ACC TGC           11011
Glu Asp Asn Ser Asp Glu Asp Ser Ser His Cys Ala Ser Arg Thr Cys
3620                3625                3630                3635

CGG CCG GGC CAG TTT CGG TGT GCT AAT GGC CGC TGC ATC CCG CAG GCC           11059
Arg Pro Gly Gln Phe Arg Cys Ala Asn Gly Arg Cys Ile Pro Gln Ala
            3640                3645                3650

TGG AAG TGT GAT GTG GAT AAT GAT TGT GGA GAC CAC TCG GAT GAG CCC           11107
Trp Lys Cys Asp Val Asp Asn Asp Cys Gly Asp His Ser Asp Glu Pro
            3655                3660                3665

ATT GAA GAA TGC ATG AGC TCT GCC CAT CTC TGT GAC AAC TTC ACA GAA           11155
Ile Glu Glu Cys Met Ser Ser Ala His Leu Cys Asp Asn Phe Thr Glu
            3670                3675                3680

TTC AGC TGC AAA ACA AAT TAC CGC TGC ATC CCA AAG TGG GCC GTG TGC           11203
Phe Ser Cys Lys Thr Asn Tyr Arg Cys Ile Pro Lys Trp Ala Val Cys
            3685                3690                3695

AAT GGT GTA GAT GAC TGC AGG GAC AAC AGT GAT GAG CAA GGC TGT GAG           11251
Asn Gly Val Asp Asp Cys Arg Asp Asn Ser Asp Glu Gln Gly Cys Glu
3700                3705                3710                3715

GAG AGG ACA TGC CAT CCT GTG GGG GAT TTC CGC TGT AAA AAT CAC CAC           11299
Glu Arg Thr Cys His Pro Val Gly Asp Phe Arg Cys Lys Asn His His
            3720                3725                3730

TGC ATC CCT CTT CGT TGG CAG TGT GAT GGG CAA AAT GAC TGT GGA GAT           11347
Cys Ile Pro Leu Arg Trp Gln Cys Asp Gly Gln Asn Asp Cys Gly Asp
            3735                3740                3745

AAC TCA GAT GAG GAA AAC TGT GCT CCC CGG GAG TGC ACA GAG AGC GAG           11395
Asn Ser Asp Glu Glu Asn Cys Ala Pro Arg Glu Cys Thr Glu Ser Glu
            3750                3755                3760

TTT CGA TGT GTC AAT CAG CAG TGC ATT CCC TCG CGA TGG ATC TGT GAC           11443
Phe Arg Cys Val Asn Gln Gln Cys Ile Pro Ser Arg Trp Ile Cys Asp
            3765                3770                3775

CAT TAC AAC GAC TGT GGG GAC AAC TCA GAT GAA CGG GAC TGT GAG ATG           11491
His Tyr Asn Asp Cys Gly Asp Asn Ser Asp Glu Arg Asp Cys Glu Met
3780                3785                3790                3795

AGG ACC TGC CAT CCT GAA TAT TTT CAG TGT ACA AGT GGA CAT TGT GTA           11539
Arg Thr Cys His Pro Glu Tyr Phe Gln Cys Thr Ser Gly His Cys Val
            3800                3805                3810

CAC AGT GAA CTG AAA TGC GAT GGA TCC GCT GAC TGT TTG GAT GCG TCT           11587
His Ser Glu Leu Lys Cys Asp Gly Ser Ala Asp Cys Leu Asp Ala Ser
            3815                3820                3825

GAT GAA GCT GAT TGT CCC ACA CGC TTT CCT GAT GGT GCA TAC TGC CAG           11635
Asp Glu Ala Asp Cys Pro Thr Arg Phe Pro Asp Gly Ala Tyr Cys Gln
            3830                3835                3840

GCT ACT ATG TTC GAA TGC AAA AAC CAT GTT TGT ATC CCG CCA TAT TGG           11683
Ala Thr Met Phe Glu Cys Lys Asn His Val Cys Ile Pro Pro Tyr Trp
            3845                3850                3855

AAA TGT GAT GGC GAT GAT GAC TGT GGC GAT GGT TCA GAT GAA GAA CTT           11731
Lys Cys Asp Gly Asp Asp Asp Cys Gly Asp Gly Ser Asp Glu Glu Leu
3860                3865                3870                3875

CAC CTG TGC TTG GAT GTT CCC TGT AAT TCA CCA AAC CGT TTC CGG TGT           11779
His Leu Cys Leu Asp Val Pro Cys Asn Ser Pro Asn Arg Phe Arg Cys
            3880                3885                3890

GAC AAC AAT CGC TGC ATT TAT AGT CAT GAG GTG TGC AAT GGT GTG GAT           11827
Asp Asn Asn Arg Cys Ile Tyr Ser His Glu Val Cys Asn Gly Val Asp
            3895                3900                3905
```

```
GAC TGT GGA GAT GGA ACT GAT GAG ACA GAG GAG CAC TGT AGA AAA CCG    11875
Asp Cys Gly Asp Gly Thr Asp Glu Thr Glu Glu His Cys Arg Lys Pro
            3910                3915                3920

ACC CCT AAA CCT TGT ACA GAA TAT GAA TAT AAG TGT GGC AAT GGG CAT    11923
Thr Pro Lys Pro Cys Thr Glu Tyr Glu Tyr Lys Cys Gly Asn Gly His
        3925                3930                3935

TGC ATT CCA CAT GAC AAT GTG TGT GAT GAT GCC GAT GAC TGT GGT GAC    11971
Cys Ile Pro His Asp Asn Val Cys Asp Asp Ala Asp Asp Cys Gly Asp
3940                3945                3950                3955

TGG TCC GAT GAA CTG GGT TGC AAT AAA GGA AAA GAA AGA ACA TGT GCT    12019
Trp Ser Asp Glu Leu Gly Cys Asn Lys Gly Lys Glu Arg Thr Cys Ala
                3960                3965                3970

GAA AAT ATA TGC GAG CAA AAT TGT ACC CAA TTA AAT GAA GGA GGA TTT    12067
Glu Asn Ile Cys Glu Gln Asn Cys Thr Gln Leu Asn Glu Gly Gly Phe
            3975                3980                3985

ATC TGC TCC TGT ACA GCT GGG TTC GAA ACC AAT GTT TTT GAC AGA ACC    12115
Ile Cys Ser Cys Thr Ala Gly Phe Glu Thr Asn Val Phe Asp Arg Thr
            3990                3995                4000

TCC TGT CTA GAT ATC AAT GAA TGT GAA CAA TTT GGG ACT TGT CCC CAG    12163
Ser Cys Leu Asp Ile Asn Glu Cys Glu Gln Phe Gly Thr Cys Pro Gln
        4005                4010                4015

CAC TGC AGA AAT ACC AAA GGA AGT TAT GAG TGT GTC TGT GCT GAT GGC    12211
His Cys Arg Asn Thr Lys Gly Ser Tyr Glu Cys Val Cys Ala Asp Gly
4020                4025                4030                4035

TTC ACG TCT ATG AGT GAC CGC CCT GGA AAA CGA TGT GCA GCT GAG GGT    12259
Phe Thr Ser Met Ser Asp Arg Pro Gly Lys Arg Cys Ala Ala Glu Gly
            4040                4045                4050

AGC TCT CCT TTG TTG CTA CTG CCT GAC AAT GTC CGA ATT CGA AAA TAT    12307
Ser Ser Pro Leu Leu Leu Leu Pro Asp Asn Val Arg Ile Arg Lys Tyr
            4055                4060                4065

AAT CTC TCA TCT GAG AGG TTC TCA GAG TAT CTT CAA GAT GAG GAA TAT    12355
Asn Leu Ser Ser Glu Arg Phe Ser Glu Tyr Leu Gln Asp Glu Glu Tyr
        4070                4075                4080

ATC CAA GCT GTT GAT TAT GAT TGG GAT CCC AAG GAC ATA GGC CTC AGT    12403
Ile Gln Ala Val Asp Tyr Asp Trp Asp Pro Lys Asp Ile Gly Leu Ser
        4085                4090                4095

GTT GTG TAT TAC ACT GTG CGA GGG GAG GGC TCT AGG TTT GGT GCT ATC    12451
Val Val Tyr Tyr Thr Val Arg Gly Glu Gly Ser Arg Phe Gly Ala Ile
4100                4105                4110                4115

AAA CGT GCC TAC ATC CCC AAC TTT GAA TCC GGC CGC AAT AAT CTT GTG    12499
Lys Arg Ala Tyr Ile Pro Asn Phe Glu Ser Gly Arg Asn Asn Leu Val
            4120                4125                4130

CAG GAA GTT GAC CTG AAA CTG AAA TAC GTA ATG CAG CCA GAT GGA ATA    12547
Gln Glu Val Asp Leu Lys Leu Lys Tyr Val Met Gln Pro Asp Gly Ile
            4135                4140                4145

GCA GTG GAC TGG GTT GGA AGG CAT ATT TAC TGG TCA GAT GTC AAG AAT    12595
Ala Val Asp Trp Val Gly Arg His Ile Tyr Trp Ser Asp Val Lys Asn
            4150                4155                4160

AAA CGC ATT GAG GTG GCT AAA CTT GAT GGA AGG TAC AGA AAG TGG CTG    12643
Lys Arg Ile Glu Val Ala Lys Leu Asp Gly Arg Tyr Arg Lys Trp Leu
        4165                4170                4175

ATT TCC ACT GAC CTG GAC CAA CCA GCT GCT ATT GCT GTG AAT CCC AAA    12691
Ile Ser Thr Asp Leu Asp Gln Pro Ala Ala Ile Ala Val Asn Pro Lys
4180                4185                4190                4195

CTA GGG CTT ATG TTC TGG ACT GAC TGG GGA AAG GAA CCT AAA ATC GAG    12739
Leu Gly Leu Met Phe Trp Thr Asp Trp Gly Lys Glu Pro Lys Ile Glu
            4200                4205                4210

TCT GCC TGG ATG AAT GGA GAG GAC CGC AAC ATC CTG GTT TTC GAG GAC    12787
Ser Ala Trp Met Asn Gly Glu Asp Arg Asn Ile Leu Val Phe Glu Asp
```

```
                    4215                4220                4225
CTT GGT TGG CCA ACT GGC CTT TCT ATC GAT TAT TTG AAC GAC CGA ATC      12835
Leu Gly Trp Pro Thr Gly Leu Ser Ile Asp Tyr Leu Asn Asp Arg Ile
            4230                4235                4240

TAC TGG AGT GAC TTC AAG GAG GAC GTT ATT GAA ACC ATA AAA TAT GAT      12883
Tyr Trp Ser Asp Phe Lys Glu Asp Val Ile Glu Thr Ile Lys Tyr Asp
            4245                4250                4255

GGG ACT GAT AGG AGA GTC ATT GCA AAG GAA GCA ATG AAC CCT TAC AGC      12931
Gly Thr Asp Arg Arg Val Ile Ala Lys Glu Ala Met Asn Pro Tyr Ser
4260                4265                4270                4275

CTG GAC ATC TTT GAA GAC CAG TTA TAC TGG ATA TCT AAG GAA AAG GGA      12979
Leu Asp Ile Phe Glu Asp Gln Leu Tyr Trp Ile Ser Lys Glu Lys Gly
            4280                4285                4290

GAA GTA TGG AAA CAA AAT AAA TTT GGG CAA GGA AAG AAA GAG AAA ACG      13027
Glu Val Trp Lys Gln Asn Lys Phe Gly Gln Gly Lys Lys Glu Lys Thr
            4295                4300                4305

CTG GTA GTG AAC CCT TGG CTC ACT CAA GTT CGA ATC TTT CAT CAA CTC      13075
Leu Val Val Asn Pro Trp Leu Thr Gln Val Arg Ile Phe His Gln Leu
            4310                4315                4320

AGA TAC AAT AAG TCA GTG CCC AAC CTT TGC AAA CAG ATC TGC AGC CAC      13123
Arg Tyr Asn Lys Ser Val Pro Asn Leu Cys Lys Gln Ile Cys Ser His
            4325                4330                4335

CTC TGC CTT CTG AGA CCT GGA GGA TAC AGC TGT GCC TGT CCC CAA GGC      13171
Leu Cys Leu Leu Arg Pro Gly Gly Tyr Ser Cys Ala Cys Pro Gln Gly
4340                4345                4350                4355

TCC AGC TTT ATA GAG GGG AGC ACC ACT GAG TGT GAT GCA GCC ATC GAA      13219
Ser Ser Phe Ile Glu Gly Ser Thr Thr Glu Cys Asp Ala Ala Ile Glu
            4360                4365                4370

CTG CCT ATC AAC CTG CCC CCC CCA TGC AGG TGC ATG CAC GGA GGA AAT      13267
Leu Pro Ile Asn Leu Pro Pro Pro Cys Arg Cys Met His Gly Gly Asn
            4375                4380                4385

TGC TAT TTT GAT GAG ACT GAC CTC CCC AAA TGC AAG TGT CCT AGC GGC      13315
Cys Tyr Phe Asp Glu Thr Asp Leu Pro Lys Cys Lys Cys Pro Ser Gly
            4390                4395                4400

TAC ACC GGA AAA TAT TGT GAA ATG GCG TTT TCA AAA GGC ATC TCT CCA      13363
Tyr Thr Gly Lys Tyr Cys Glu Met Ala Phe Ser Lys Gly Ile Ser Pro
            4405                4410                4415

GGA ACA ACC GCA GTA GCT GTG CTG TTG ACA ATC CTC TTG ATC GTC GTA      13411
Gly Thr Thr Ala Val Ala Val Leu Leu Thr Ile Leu Leu Ile Val Val
4420                4425                4430                4435

ATT GGA GCT CTG GCA ATT GCA GGA TTC TTC CAC TAT AGA AGG ACC GGC      13459
Ile Gly Ala Leu Ala Ile Ala Gly Phe Phe His Tyr Arg Arg Thr Gly
            4440                4445                4450

TCC CTT TTG CCT GCT CTG CCC AAG CTG CCA AGC TTA AGC AGT CTC GTC      13507
Ser Leu Leu Pro Ala Leu Pro Lys Leu Pro Ser Leu Ser Ser Leu Val
            4455                4460                4465

AAG CCC TCT GAA AAT GGG AAT GGG GTG ACC TTC AGA TCA GGG GCA GAT      13555
Lys Pro Ser Glu Asn Gly Asn Gly Val Thr Phe Arg Ser Gly Ala Asp
            4470                4475                4480

CTT AAC ATG GAT ATT GGA GTG TCT GGT TTT GGA CCT GAG ACT GCT ATT      13603
Leu Asn Met Asp Ile Gly Val Ser Gly Phe Gly Pro Glu Thr Ala Ile
            4485                4490                4495

GAC AGG TCA ATG GCA ATG AGT GAA GAC TTT GTC ATG GAA ATG GGG AAG      13651
Asp Arg Ser Met Ala Met Ser Glu Asp Phe Val Met Glu Met Gly Lys
4500                4505                4510                4515

CAG CCC ATA ATA TTT GAA AAC CCA ATG TAC TCA GCC AGA GAC AGT GCT      13699
Gln Pro Ile Ile Phe Glu Asn Pro Met Tyr Ser Ala Arg Asp Ser Ala
            4520                4525                4530

GTC AAA GTG GTT CAG CCA ATC CAG GTG ACT GTA TCT GAA AAT GTG GAT      13747
```

```
Val Lys Val Val Gln Pro Ile Gln Val Thr Val Ser Glu Asn Val Asp
            4535                4540                4545

AAT AAG AAT TAT GGA AGT CCC ATA AAC CCT TCT GAG ATA GTT CCA GAG      13795
Asn Lys Asn Tyr Gly Ser Pro Ile Asn Pro Ser Glu Ile Val Pro Glu
        4550                4555                4560

ACA AAC CCA ACT TCA CCA GCT GCT GAT GGA ACT CAG GTG ACA AAA TGG      13843
Thr Asn Pro Thr Ser Pro Ala Ala Asp Gly Thr Gln Val Thr Lys Trp
        4565                4570                4575

AAT CTC TTC AAA CGA AAA TCT AAA CAA ACT ACC AAC TTT GAA AAT CCA      13891
Asn Leu Phe Lys Arg Lys Ser Lys Gln Thr Thr Asn Phe Glu Asn Pro
4580                4585                4590                4595

ATC TAT GCA CAG ATG GAG AAC GAG CAA AAG GAA AGT GTT GCT GCG ACA      13939
Ile Tyr Ala Gln Met Glu Asn Glu Gln Lys Glu Ser Val Ala Ala Thr
            4600                4605                4610

CCA CCT CCA TCA CCT TCG CTC CCT GCT AAG CCT AAG CCT CCT TCG AGA      13987
Pro Pro Pro Ser Pro Ser Leu Pro Ala Lys Pro Lys Pro Pro Ser Arg
            4615                4620                4625

AGA GAC CCA ACT CCA ACC TAT TCT GCA ACA GAA GAC ACT TTT AAA GAC      14035
Arg Asp Pro Thr Pro Thr Tyr Ser Ala Thr Glu Asp Thr Phe Lys Asp
            4630                4635                4640

ACC GCA AAT CTT GTT AAA GAA GAC TCT GAA GTA TAG GATCAAGAAG           14081
Thr Ala Asn Leu Val Lys Glu Asp Ser Glu Val  *
            4645                4650                4655

AA                                                                   14083
```

(2) INFORMATION FOR SEQ ID NO: 84:

(i) SEQUENCE CHARACTERISTICS:
        (A) LENGTH: 4654 amino acids
        (B) TYPE: amino acid
        (D) TOPOLOGY: linear (ii) MOLECULE TYPE: protein (xi) SEQUENCE DESCRIPTION: SEQ ID NO: 84:

```
Met Asp Arg Gly Pro Ala Ala Val Ala Cys Thr Leu Leu Ala Leu
 1               5                  10                  15

Val Ala Cys Leu Ala Pro Ala Ser Gly Gln Glu Cys Asp Ser Ala His
            20                  25                  30

Phe Arg Cys Gly Ser Gly His Cys Ile Pro Ala Asp Trp Arg Cys Asp
            35                  40                  45

Gly Thr Lys Asp Cys Ser Asp Ala Asp Glu Ile Gly Cys Ala Val
     50                  55                  60

Val Thr Cys Gln Gln Gly Tyr Phe Lys Cys Gln Ser Glu Gly Gln Cys
 65                  70                  75                  80

Ile Pro Ser Ser Trp Val Cys Asp Gln Asp Gln Cys Asp Asp Gly
                85                  90                  95

Ser Asp Glu Arg Gln Asp Cys Ser Gln Ser Thr Cys Ser Ser His Gln
                100                 105                 110

Ile Thr Cys Ser Asn Gly Gln Cys Ile Pro Ser Glu Tyr Arg Cys Asp
            115                 120                 125

His Val Arg Asp Cys Pro Asp Gly Ala Asp Glu Asn Asp Cys Gln Tyr
            130                 135                 140

Pro Thr Cys Glu Gln Leu Thr Cys Asp Asn Gly Ala Cys Tyr Asn Thr
145                 150                 155                 160

Ser Gln Lys Cys Asp Trp Lys Val Asp Cys Arg Asp Ser Ser Asp Glu
                165                 170                 175

Ile Asn Cys Thr Glu Ile Cys Leu His Asn Glu Phe Ser Cys Gly Asn
```

-continued

```
                180                 185                 190
Gly Glu Cys Ile Pro Arg Ala Tyr Val Cys Asp His Asp Asn Asp Cys
            195                 200                 205
Gln Asp Gly Ser Asp Glu His Ala Cys Asn Tyr Pro Thr Cys Gly Gly
            210                 215                 220
Tyr Gln Phe Thr Cys Pro Ser Gly Arg Cys Ile Tyr Gln Asn Trp Val
225                 230                 235                 240
Cys Asp Gly Glu Asp Asp Cys Lys Asp Asn Gly Asp Glu Asp Gly Cys
            245                 250                 255
Glu Ser Gly Pro His Asp Val His Lys Cys Ser Pro Arg Glu Trp Ser
            260                 265                 270
Cys Pro Glu Ser Gly Arg Cys Ile Ser Ile Tyr Lys Val Cys Asp Gly
            275                 280                 285
Ile Leu Asp Cys Pro Gly Arg Glu Asp Glu Asn Asn Thr Ser Thr Gly
            290                 295                 300
Lys Tyr Cys Ser Met Thr Leu Cys Ser Ala Leu Asn Cys Gln Tyr Gln
305                 310                 315                 320
Cys His Glu Thr Pro Tyr Gly Gly Ala Cys Phe Cys Pro Pro Gly Tyr
            325                 330                 335
Ile Ile Asn His Asn Asp Ser Arg Thr Cys Val Glu Phe Asp Asp Cys
            340                 345                 350
Gln Ile Trp Gly Ile Cys Asp Gln Lys Cys Glu Ser Arg Pro Gly Arg
            355                 360                 365
His Leu Cys His Cys Glu Glu Gly Tyr Ile Leu Glu Arg Gly Gln Tyr
            370                 375                 380
Cys Lys Ala Asn Asp Ser Phe Gly Glu Ala Ser Ile Ile Phe Ser Asn
385                 390                 395                 400
Gly Arg Asp Leu Leu Ile Gly Asp Ile His Gly Arg Ser Phe Arg Ile
            405                 410                 415
Leu Val Glu Ser Gln Asn Arg Gly Val Ala Val Gly Val Ala Phe His
            420                 425                 430
Tyr His Leu Gln Arg Val Phe Trp Thr Asp Thr Val Gln Asn Lys Val
            435                 440                 445
Phe Ser Val Asp Ile Asn Gly Leu Asn Ile Gln Glu Val Leu Asn Val
450                 455                 460
Ser Val Glu Thr Pro Glu Asn Leu Ala Val Asp Trp Val Asn Asn Lys
465                 470                 475                 480
Ile Tyr Leu Val Glu Thr Lys Val Asn Arg Ile Asp Met Val Asn Leu
            485                 490                 495
Asp Gly Ser Tyr Arg Val Thr Leu Ile Thr Glu Asn Leu Gly His Pro
            500                 505                 510
Arg Gly Ile Ala Val Asp Pro Thr Val Gly Tyr Leu Phe Phe Ser Asp
            515                 520                 525
Trp Glu Ser Leu Ser Gly Glu Pro Lys Leu Glu Arg Ala Phe Met Asp
            530                 535                 540
Gly Ser Asn Arg Lys Asp Leu Val Lys Thr Lys Leu Gly Trp Pro Ala
545                 550                 555                 560
Gly Val Thr Leu Asp Met Ile Ser Lys Arg Val Tyr Trp Val Asp Ser
            565                 570                 575
Arg Phe Asp Tyr Ile Glu Thr Val Thr Tyr Asp Gly Ile Gln Arg Lys
            580                 585                 590
Thr Val Val His Gly Gly Ser Leu Ile Pro His Pro Phe Gly Val Ser
            595                 600                 605
```

```
Leu Phe Glu Gly Gln Val Phe Phe Thr Asp Trp Thr Lys Met Ala Val
    610                 615                 620
Leu Lys Ala Asn Lys Phe Thr Glu Thr Asn Pro Gln Val Tyr Tyr Gln
625                 630                 635                 640
Ala Ser Leu Arg Pro Tyr Gly Val Thr Val Tyr His Ser Leu Arg Gln
                645                 650                 655
Pro Tyr Ala Thr Asn Pro Cys Lys Asp Asn Gly Gly Cys Glu Gln
                660                 665                 670
Val Cys Val Leu Ser His Arg Thr Asp Asn Asp Gly Leu Gly Phe Arg
    675                 680                 685
Cys Lys Cys Thr Phe Gly Phe Gln Leu Asp Thr Asp Glu Arg His Cys
    690                 695                 700
Ile Ala Val Gln Asn Phe Leu Ile Phe Ser Ser Gln Val Ala Ile Arg
705                 710                 715                 720
Gly Ile Pro Phe Thr Leu Ser Thr Gln Glu Asp Val Met Val Pro Val
                725                 730                 735
Ser Gly Asn Pro Ser Phe Phe Val Gly Ile Asp Phe Asp Ala Gln Asp
                740                 745                 750
Ser Thr Ile Phe Phe Ser Asp Met Ser Lys His Met Ile Phe Lys Gln
                755                 760                 765
Lys Ile Asp Gly Thr Gly Arg Glu Ile Leu Ala Ala Asn Arg Val Glu
770                 775                 780
Asn Val Glu Ser Leu Ala Phe Asp Trp Ile Ser Lys Asn Leu Tyr Trp
785                 790                 795                 800
Thr Asp Ser His Tyr Lys Ser Ile Ser Val Met Arg Leu Ala Asp Lys
                805                 810                 815
Thr Arg Arg Thr Val Val Gln Tyr Leu Asn Asn Pro Arg Ser Val Val
                820                 825                 830
Val His Pro Phe Ala Gly Tyr Leu Phe Phe Thr Asp Trp Phe Arg Pro
                835                 840                 845
Ala Lys Ile Met Arg Ala Trp Ser Asp Gly Ser His Leu Leu Pro Val
    850                 855                 860
Ile Asn Thr Thr Leu Gly Trp Pro Asn Gly Leu Ala Ile Asp Trp Ala
865                 870                 875                 880
Ala Ser Arg Leu Tyr Trp Val Asp Ala Tyr Phe Asp Lys Ile Glu His
                885                 890                 895
Ser Thr Phe Asp Gly Leu Asp Arg Arg Leu Gly His Ile Glu Gln
                900                 905                 910
Met Thr His Pro Phe Gly Leu Ala Ile Phe Gly Glu His Leu Phe Phe
                915                 920                 925
Thr Asp Trp Arg Leu Gly Ala Ile Ile Arg Val Arg Lys Ala Asp Gly
    930                 935                 940
Gly Glu Met Thr Val Ile Arg Ser Gly Ile Ala Tyr Ile Leu His Leu
945                 950                 955                 960
Lys Ser Tyr Asp Val Asn Ile Gln Thr Gly Ser Asn Ala Cys Asn Gln
                965                 970                 975
Pro Thr His Pro Asn Gly Asp Cys Ser His Phe Cys Phe Pro Val Pro
                980                 985                 990
Asn Phe Gln Arg Val Cys Gly Cys Pro Tyr Gly Met Arg Leu Ala Ser
            995                 1000                1005
Asn His Leu Thr Cys Glu Gly Asp Pro Thr Asn Glu Pro Pro Thr Glu
    1010                1015                1020
```

-continued

```
Gln Cys Gly Leu Phe Ser Phe Pro Cys Lys Asn Gly Arg Cys Val Pro
1025                1030                1035                1040

Asn Tyr Tyr Leu Cys Asp Gly Val Asp Asp Cys His Asp Asn Ser Asp
            1045                1050                1055

Glu Gln Leu Cys Gly Thr Leu Asn Asn Thr Cys Ser Ser Ser Ala Phe
                1060                1065                1070

Thr Cys Gly His Gly Glu Cys Ile Pro Ala His Trp Arg Cys Asp Lys
        1075                1080                1085

Arg Asn Asp Cys Val Asp Gly Ser Asp Glu His Asn Cys Pro Thr His
    1090                1095                1100

Ala Pro Ala Ser Cys Leu Asp Thr Gln Tyr Thr Cys Asp Asn His Gln
1105                1110                1115                1120

Cys Ile Ser Lys Asn Trp Val Cys Asp Thr Asp Asn Asp Cys Gly Asp
            1125                1130                1135

Gly Ser Asp Glu Lys Asn Cys Asn Ser Thr Glu Thr Cys Gln Pro Ser
                1140                1145                1150

Gln Phe Asn Cys Pro Asn His Arg Cys Ile Asp Leu Ser Phe Val Cys
        1155                1160                1165

Asp Gly Asp Lys Asp Cys Val Asp Gly Ser Asp Glu Val Gly Cys Val
    1170                1175                1180

Leu Asn Cys Thr Ala Ser Gln Phe Lys Cys Ala Ser Gly Asp Lys Cys
1185                1190                1195                1200

Ile Gly Val Thr Asn Arg Cys Asp Gly Val Phe Asp Cys Ser Asp Asn
            1205                1210                1215

Ser Asp Glu Ala Gly Cys Pro Thr Arg Pro Pro Gly Met Cys His Ser
                1220                1225                1230

Asp Glu Phe Gln Cys Gln Glu Asp Gly Ile Cys Ile Pro Asn Phe Trp
        1235                1240                1245

Glu Cys Asp Gly His Pro Asp Cys Leu Tyr Gly Ser Asp Glu His Asn
    1250                1255                1260

Ala Cys Val Pro Lys Thr Cys Pro Ser Ser Tyr Phe His Cys Asp Asn
1265                1270                1275                1280

Gly Asn Cys Ile His Arg Ala Trp Leu Cys Asp Arg Asp Asn Asp Cys
            1285                1290                1295

Gly Asp Met Ser Asp Glu Lys Asp Cys Pro Thr Gln Pro Phe Arg Cys
                1300                1305                1310

Pro Ser Trp Gln Trp Gln Cys Leu Gly His Asn Ile Cys Val Asn Leu
        1315                1320                1325

Ser Val Val Cys Asp Gly Ile Phe Asp Cys Pro Asn Gly Thr Asp Glu
    1330                1335                1340

Ser Pro Leu Cys Asn Gly Asn Ser Cys Ser Asp Phe Asn Gly Gly Cys
1345                1350                1355                1360

Thr His Glu Cys Val Gln Glu Pro Phe Gly Ala Lys Cys Leu Cys Pro
            1365                1370                1375

Leu Gly Phe Leu Leu Ala Asn Asp Ser Lys Thr Cys Glu Asp Ile Asp
                1380                1385                1390

Glu Cys Asp Ile Leu Gly Ser Cys Ser Gln His Cys Tyr Asn Met Arg
        1395                1400                1405

Gly Ser Phe Arg Cys Ser Cys Asp Thr Gly Tyr Met Leu Glu Ser Asp
    1410                1415                1420

Gly Arg Thr Cys Lys Val Thr Ala Ser Glu Ser Leu Leu Leu Leu Val
1425                1430                1435                1440

Ala Ser Gln Asn Lys Ile Ile Ala Asp Ser Val Thr Ser Gln Val His
```

-continued

```
                1445                1450                1455

Asn Ile Tyr Ser Leu Val Glu Asn Gly Ser Tyr Ile Val Ala Val Asp
                1460                1465                1470

Phe Asp Ser Ile Ser Gly Arg Ile Phe Trp Ser Asp Ala Thr Gln Gly
        1475                1480                1485

Lys Thr Trp Ser Ala Phe Gln Asn Gly Thr Asp Arg Arg Val Val Phe
        1490                1495                1500

Asp Ser Ser Ile Ile Leu Thr Glu Thr Ile Ala Ile Asp Trp Val Gly
1505                1510                1515                1520

Arg Asn Leu Tyr Trp Thr Asp Tyr Ala Leu Glu Thr Ile Glu Val Ser
                1525                1530                1535

Lys Ile Asp Gly Ser His Arg Thr Val Leu Ile Ser Lys Asn Leu Thr
                1540                1545                1550

Asn Pro Arg Gly Leu Ala Leu Asp Pro Arg Met Asn Glu His Leu Leu
                1555                1560                1565

Phe Trp Ser Asp Trp Gly His His Pro Arg Ile Glu Arg Ala Ser Met
        1570                1575                1580

Asp Gly Ser Met Arg Thr Val Ile Val Gln Asp Lys Ile Phe Trp Pro
1585                1590                1595                1600

Cys Gly Leu Thr Ile Asp Tyr Pro Asn Arg Leu Leu Tyr Phe Met Asp
                1605                1610                1615

Ser Tyr Leu Asp Tyr Met Asp Phe Cys Asp Tyr Asn Gly His His Arg
                1620                1625                1630

Arg Gln Val Ile Ala Ser Asp Leu Ile Ile Arg His Pro Tyr Ala Leu
                1635                1640                1645

Thr Leu Phe Glu Asp Ser Val Tyr Trp Thr Asp Arg Ala Thr Arg Arg
        1650                1655                1660

Val Met Arg Ala Asn Lys Trp His Gly Gly Asn Gln Ser Val Val Met
1665                1670                1675                1680

Tyr Asn Ile Gln Trp Pro Leu Gly Ile Val Ala Val His Pro Ser Lys
                1685                1690                1695

Gln Pro Asn Ser Val Asn Pro Cys Ala Phe Ser Arg Cys Ser His Leu
                1700                1705                1710

Cys Leu Leu Ser Ser Gln Gly Pro His Phe Tyr Ser Cys Val Cys Pro
        1715                1720                1725

Ser Gly Trp Ser Leu Ser Pro Asp Leu Leu Asn Cys Leu Arg Asp Asp
        1730                1735                1740

Gln Pro Phe Leu Ile Thr Val Arg Gln His Ile Ile Phe Gly Ile Ser
1745                1750                1755                1760

Leu Asn Pro Glu Val Lys Ser Asn Asp Ala Met Val Pro Ile Ala Gly
                1765                1770                1775

Ile Gln Asn Gly Leu Asp Val Glu Phe Asp Asp Ala Glu Gln Tyr Ile
                1780                1785                1790

Tyr Trp Val Glu Asn Pro Gly Glu Ile His Arg Val Lys Thr Asp Gly
        1795                1800                1805

Thr Asn Arg Thr Val Phe Ala Ser Ile Ser Met Val Gly Pro Ser Met
        1810                1815                1820

Asn Leu Ala Leu Asp Trp Ile Ser Arg Asn Leu Tyr Ser Thr Asn Pro
1825                1830                1835                1840

Arg Thr Gln Ser Ile Glu Val Leu Thr Leu His Gly Asp Ile Arg Tyr
                1845                1850                1855

Arg Lys Thr Leu Ile Ala Asn Asp Gly Thr Ala Leu Gly Val Gly Phe
        1860                1865                1870
```

-continued

Pro Ile Gly Ile Thr Val Asp Pro Ala Arg Gly Lys Leu Tyr Trp Ser
        1875                1880                1885

Asp Gln Gly Thr Asp Ser Gly Val Pro Ala Lys Ile Ala Ser Ala Asn
        1890                1895                1900

Met Asp Gly Thr Ser Val Lys Thr Leu Phe Thr Gly Asn Leu Glu His
1905                1910                1915                1920

Leu Glu Cys Val Thr Leu Asp Ile Glu Glu Gln Lys Leu Tyr Trp Ala
            1925                1930                1935

Val Thr Gly Arg Gly Val Ile Glu Arg Gly Asn Val Asp Gly Thr Asp
            1940                1945                1950

Arg Met Ile Leu Val His Gln Leu Ser His Pro Trp Gly Ile Ala Val
            1955                1960                1965

His Asp Ser Phe Leu Tyr Tyr Thr Asp Glu Gln Tyr Glu Val Ile Glu
    1970                1975                1980

Arg Val Asp Lys Ala Thr Gly Ala Asn Lys Ile Val Leu Arg Asp Asn
1985                1990                1995                2000

Val Pro Asn Leu Arg Gly Leu Gln Val Tyr His Arg Arg Asn Ala Ala
            2005                2010                2015

Glu Ser Ser Asn Gly Cys Ser Asn Asn Met Asn Ala Cys Gln Gln Ile
            2020                2025                2030

Cys Leu Pro Val Pro Gly Gly Leu Phe Ser Cys Ala Cys Ala Thr Gly
            2035                2040                2045

Phe Lys Leu Asn Pro Asp Asn Arg Ser Cys Ser Pro Tyr Asn Ser Phe
            2050                2055                2060

Ile Val Val Ser Met Leu Ser Ala Ile Arg Gly Phe Ser Leu Glu Leu
2065                2070                2075                2080

Ser Asp His Ser Glu Thr Met Val Pro Val Ala Gly Gln Gly Arg Asn
            2085                2090                2095

Ala Leu His Val Asp Val Asp Val Ser Ser Gly Phe Ile Tyr Trp Cys
            2100                2105                2110

Asp Phe Ser Ser Val Ala Ser Asp Asn Ala Ile Arg Arg Ile Lys
            2115                2120                2125

Pro Asp Gly Ser Ser Leu Met Asn Ile Val Thr His Gly Ile Gly Glu
            2130                2135                2140

Asn Gly Val Arg Gly Ile Ala Val Asp Trp Val Ala Gly Asn Leu Tyr
2145                2150                2155                2160

Phe Thr Asn Ala Phe Val Ser Glu Thr Leu Ile Glu Val Leu Arg Ile
            2165                2170                2175

Asn Thr Thr Tyr Arg Arg Val Leu Leu Lys Val Thr Val Asp Met Pro
            2180                2185                2190

Arg His Ile Val Val Asp Pro Lys Asn Arg Tyr Leu Phe Trp Ala Asp
            2195                2200                2205

Tyr Gly Gln Arg Pro Lys Ile Glu Arg Ser Phe Leu Asp Cys Thr Asn
            2210                2215                2220

Arg Thr Val Leu Val Ser Glu Gly Ile Val Thr Pro Arg Gly Leu Ala
2225                2230                2235                2240

Val Asp Arg Ser Asp Gly Tyr Val Tyr Trp Val Asp Asp Ser Leu Asp
            2245                2250                2255

Ile Ile Ala Arg Ile Arg Ile Asn Gly Glu Asn Ser Glu Val Ile Arg
            2260                2265                2270

Tyr Gly Ser Arg Tyr Pro Thr Pro Tyr Gly Ile Thr Val Phe Glu Asn
            2275                2280                2285

-continued

```
Ser Ile Ile Trp Val Asp Arg Asn Leu Lys Lys Ile Phe Gln Ala Ser
    2290                2295                2300

Lys Glu Pro Glu Asn Thr Glu Pro Pro Thr Val Ile Arg Asp Asn Ile
2305                2310                2315                2320

Asn Trp Leu Arg Asp Val Thr Ile Phe Asp Lys Gln Val Gln Pro Arg
                2325                2330                2335

Ser Pro Ala Glu Val Asn Asn Pro Cys Leu Glu Asn Asn Gly Gly
            2340                2345                2350

Cys Ser His Leu Cys Phe Ala Leu Pro Gly Leu His Thr Pro Lys Cys
        2355                2360                2365

Asp Cys Ala Phe Gly Thr Leu Gln Ser Asp Gly Lys Asn Cys Ala Ile
    2370                2375                2380

Ser Thr Glu Asn Phe Leu Ile Phe Ala Leu Ser Asn Ser Leu Arg Ser
2385                2390                2395                2400

Leu His Leu Asp Pro Glu Asn His Ser Pro Pro Phe Gln Thr Ile Asn
                2405                2410                2415

Val Glu Arg Thr Val Met Ser Leu Asp Tyr Asp Ser Val Ser Asp Arg
            2420                2425                2430

Ile Tyr Phe Thr Gln Asn Leu Ala Ser Gly Val Gly Gln Ile Ser Tyr
        2435                2440                2445

Ala Thr Leu Ser Ser Gly Ile His Thr Pro Thr Val Ile Ala Ser Gly
    2450                2455                2460

Ile Gly Thr Ala Asp Gly Ile Ala Phe Asp Trp Ile Thr Arg Arg Ile
2465                2470                2475                2480

Tyr Tyr Ser Asp Tyr Leu Asn Gln Met Ile Asn Ser Met Ala Glu Asp
                2485                2490                2495

Gly Ser Asn Arg Thr Val Ile Ala Arg Val Pro Lys Pro Arg Ala Ile
            2500                2505                2510

Val Leu Asp Pro Cys Gln Gly Tyr Leu Tyr Trp Ala Asp Trp Asp Thr
        2515                2520                2525

His Ala Lys Ile Glu Arg Ala Thr Leu Gly Gly Asn Phe Arg Val Pro
    2530                2535                2540

Ile Val Asn Ser Ser Leu Val Met Pro Ser Gly Leu Thr Leu Asp Tyr
2545                2550                2555                2560

Glu Glu Asp Leu Leu Tyr Trp Val Asp Ala Ser Leu Gln Arg Ile Glu
                2565                2570                2575

Arg Ser Thr Leu Thr Gly Val Asp Arg Glu Val Ile Val Asn Ala Ala
            2580                2585                2590

Val His Ala Phe Gly Leu Thr Leu Tyr Gly Gln Tyr Ile Tyr Trp Thr
        2595                2600                2605

Asp Leu Tyr Thr Gln Arg Ile Tyr Arg Ala Asn Lys Tyr Asp Gly Ser
    2610                2615                2620

Gly Gln Ile Ala Met Thr Thr Asn Leu Leu Ser Gln Pro Arg Gly Ile
2625                2630                2635                2640

Asn Thr Val Val Lys Asn Gln Lys Gln Gln Cys Asn Asn Pro Cys Glu
                2645                2650                2655

Gln Phe Asn Gly Gly Cys Ser His Ile Cys Ala Pro Gly Pro Asn Gly
            2660                2665                2670

Ala Glu Cys Gln Cys Pro His Gly Asn Trp Tyr Leu Ala Asn Asn
        2675                2680                2685

Arg Lys His Cys Ile Val Asp Asn Gly Glu Arg Cys Gly Ala Ser Ser
    2690                2695                2700

Phe Thr Cys Ser Asn Gly Arg Cys Ile Ser Glu Glu Trp Lys Cys Asp
```

-continued

```
2705                2710                2715                2720

Asn Asp Asn Asp Cys Gly Asp Gly Ser Asp Glu Met Glu Ser Val Cys
            2725                2730                2735

Ala Leu His Thr Cys Ser Pro Thr Ala Phe Thr Cys Ala Asn Gly Arg
            2740                2745                2750

Cys Val Gln Tyr Ser Tyr Arg Cys Asp Tyr Tyr Asn Asp Cys Gly Asp
            2755                2760                2765

Gly Ser Asp Glu Ala Gly Cys Leu Phe Arg Asp Cys Asn Ala Thr Thr
            2770                2775                2780

Glu Phe Met Cys Asn Asn Arg Arg Cys Ile Pro Arg Glu Phe Ile Cys
2785                2790                2795                2800

Asn Gly Val Asp Asn Cys His Asp Asn Thr Ser Asp Glu Lys Asn
            2805                2810                2815

Cys Pro Asp Arg Thr Cys Gln Ser Gly Tyr Thr Lys Cys His Asn Ser
            2820                2825                2830

Asn Ile Cys Ile Pro Arg Val Tyr Leu Cys Asp Gly Asp Asn Asp Cys
            2835                2840                2845

Gly Asp Asn Ser Asp Glu Asn Pro Thr Tyr Cys Thr Thr His Thr Cys
            2850                2855                2860

Ser Ser Ser Glu Phe Gln Cys Ala Ser Gly Arg Cys Ile Pro Gln His
2865                2870                2875                2880

Trp Tyr Cys Asp Gln Glu Thr Asp Cys Phe Asp Ala Ser Asp Glu Pro
            2885                2890                2895

Ala Ser Cys Gly His Ser Glu Arg Thr Cys Leu Ala Asp Glu Phe Lys
            2900                2905                2910

Cys Asp Gly Gly Arg Cys Ile Pro Ser Glu Trp Ile Cys Asp Gly Asp
            2915                2920                2925

Asn Asp Cys Gly Asp Met Ser Asp Glu Asp Lys Arg His Gln Cys Gln
            2930                2935                2940

Asn Gln Asn Cys Ser Asp Ser Glu Phe Leu Cys Val Asn Asp Arg Pro
2945                2950                2955                2960

Pro Asp Arg Arg Cys Ile Pro Gln Ser Trp Val Cys Asp Gly Asp Val
            2965                2970                2975

Asp Cys Thr Asp Gly Tyr Asp Glu Asn Gln Asn Cys Thr Arg Arg Thr
            2980                2985                2990

Cys Ser Glu Asn Glu Phe Thr Cys Gly Tyr Gly Leu Cys Ile Pro Lys
            2995                3000                3005

Ile Phe Arg Cys Asp Arg His Asn Asp Cys Gly Asp Tyr Ser Asp Glu
            3010                3015                3020

Arg Gly Cys Leu Tyr Gln Thr Cys Gln Gln Asn Gln Phe Thr Cys Gln
3025                3030                3035                3040

Asn Gly Arg Cys Ile Ser Lys Thr Phe Val Cys Asp Glu Asp Asn Asp
            3045                3050                3055

Cys Gly Asp Gly Ser Asp Glu Leu Met His Leu Cys His Thr Pro Glu
            3060                3065                3070

Pro Thr Cys Pro Pro His Glu Phe Lys Cys Asp Asn Gly Arg Cys Ile
            3075                3080                3085

Glu Met Met Lys Leu Cys Asn His Leu Asp Asp Cys Leu Asp Asn Ser
            3090                3095                3100

Asp Glu Lys Gly Cys Gly Ile Asn Glu Cys His Asp Pro Ser Ile Ser
3105                3110                3115                3120

Gly Cys Asp His Asn Cys Thr Asp Thr Leu Thr Ser Phe Tyr Cys Ser
            3125                3130                3135
```

-continued

```
Cys Arg Pro Gly Tyr Lys Leu Met Ser Asp Lys Arg Thr Cys Val Asp
            3140                3145                3150
Ile Asp Glu Cys Thr Glu Met Pro Phe Val Cys Ser Gln Lys Cys Glu
            3155                3160                3165
Asn Val Ile Gly Ser Tyr Ile Cys Lys Cys Ala Pro Gly Tyr Leu Arg
            3170                3175                3180
Glu Pro Asp Gly Lys Thr Cys Arg Gln Asn Ser Asn Ile Glu Pro Tyr
3185                3190                3195                3200
Leu Ile Phe Ser Asn Arg Tyr Tyr Leu Arg Asn Leu Thr Ile Asp Gly
            3205                3210                3215
Tyr Phe Tyr Ser Leu Ile Leu Glu Gly Leu Asp Asn Val Val Ala Leu
            3220                3225                3230
Asp Phe Asp Arg Val Glu Lys Arg Leu Tyr Trp Ile Asp Thr Gln Arg
            3235                3240                3245
Gln Val Ile Glu Arg Met Phe Leu Asn Lys Thr Asn Lys Glu Thr Ile
            3250                3255                3260
Ile Asn His Arg Leu Pro Ala Ala Glu Ser Leu Ala Val Asp Trp Val
3265                3270                3275                3280
Ser Arg Lys Leu Tyr Trp Leu Asp Ala Arg Leu Asp Gly Leu Phe Val
            3285                3290                3295
Ser Asp Leu Asn Gly Gly His Arg Arg Met Leu Ala Gln His Cys Val
            3300                3305                3310
Asp Ala Asn Asn Thr Phe Cys Phe Asp Asn Pro Arg Gly Leu Ala Leu
            3315                3320                3325
His Pro Gln Tyr Gly Tyr Leu Tyr Trp Ala Asp Trp Gly His Arg Ala
            3330                3335                3340
Tyr Ile Gly Arg Val Gly Met Asp Gly Thr Asn Lys Ser Val Ile Ile
3345                3350                3355                3360
Ser Thr Lys Leu Glu Trp Pro Asn Gly Ile Thr Ile Asp Tyr Thr Asn
            3365                3370                3375
Asp Leu Leu Tyr Trp Ala Asp Ala His Leu Gly Tyr Ile Glu Tyr Ser
            3380                3385                3390
Asp Leu Glu Gly His His Arg His Thr Val Tyr Asp Gly Ala Leu Pro
            3395                3400                3405
His Pro Phe Ala Ile Thr Ile Phe Glu Asp Thr Ile Tyr Trp Thr Asp
            3410                3415                3420
Trp Asn Thr Arg Thr Val Glu Lys Gly Asn Lys Tyr Asp Gly Ser Asn
3425                3430                3435                3440
Arg Gln Thr Leu Val Asn Thr Thr His Arg Pro Phe Asp Ile His Val
            3445                3450                3455
Tyr His Pro Tyr Arg Gln Pro Ile Val Ser Asn Pro Cys Gly Thr Asn
            3460                3465                3470
Asn Gly Gly Cys Ser His Leu Cys Leu Ile Lys Pro Gly Gly Lys Gly
            3475                3480                3485
Phe Thr Cys Glu Cys Pro Asp Asp Phe Arg Thr Leu Gln Leu Ser Gly
            3490                3495                3500
Ser Thr Tyr Cys Met Pro Met Cys Ser Ser Thr Gln Phe Leu Cys Ala
3505                3510                3515                3520
Asn Asn Glu Lys Cys Ile Pro Ile Trp Trp Lys Cys Asp Gly Gln Lys
            3525                3530                3535
Asp Cys Ser Asp Gly Ser Asp Glu Leu Ala Leu Cys Pro Gln Arg Phe
            3540                3545                3550
```

-continued

```
Cys Arg Leu Gly Gln Phe Gln Cys Ser Asp Gly Asn Cys Thr Ser Pro
            3555                3560                3565
Gln Thr Leu Cys Asn Ala His Gln Asn Cys Pro Asp Gly Ser Asp Glu
    3570                3575                3580
Asp Arg Leu Leu Cys Glu Asn His His Cys Asp Ser Asn Glu Trp Gln
3585                3590                3595                3600
Cys Ala Asn Lys Arg Cys Ile Pro Glu Ser Trp Gln Cys Asp Thr Phe
            3605                3610                3615
Asn Asp Cys Glu Asp Asn Ser Asp Glu Asp Ser Ser His Cys Ala Ser
            3620                3625                3630
Arg Thr Cys Arg Pro Gly Gln Phe Arg Cys Ala Asn Gly Arg Cys Ile
            3635                3640                3645
Pro Gln Ala Trp Lys Cys Asp Val Asp Asn Asp Cys Gly Asp His Ser
            3650                3655                3660
Asp Glu Pro Ile Glu Glu Cys Met Ser Ser Ala His Leu Cys Asp Asn
3665                3670                3675                3680
Phe Thr Glu Phe Ser Cys Lys Thr Asn Tyr Arg Cys Ile Pro Lys Trp
            3685                3690                3695
Ala Val Cys Asn Gly Val Asp Asp Cys Arg Asp Asn Ser Asp Glu Gln
            3700                3705                3710
Gly Cys Glu Glu Arg Thr Cys His Pro Val Gly Asp Phe Arg Cys Lys
            3715                3720                3725
Asn His His Cys Ile Pro Leu Arg Trp Gln Cys Asp Gly Gln Asn Asp
            3730                3735                3740
Cys Gly Asp Asn Ser Asp Glu Glu Asn Cys Ala Pro Arg Glu Cys Thr
3745                3750                3755                3760
Glu Ser Glu Phe Arg Cys Val Asn Gln Gln Cys Ile Pro Ser Arg Trp
            3765                3770                3775
Ile Cys Asp His Tyr Asn Asp Cys Gly Asp Asn Ser Asp Glu Arg Asp
            3780                3785                3790
Cys Glu Met Arg Thr Cys His Pro Glu Tyr Phe Gln Cys Thr Ser Gly
            3795                3800                3805
His Cys Val His Ser Glu Leu Lys Cys Asp Gly Ser Ala Asp Cys Leu
    3810                3815                3820
Asp Ala Ser Asp Glu Ala Asp Cys Pro Thr Arg Phe Pro Asp Gly Ala
3825                3830                3835                3840
Tyr Cys Gln Ala Thr Met Phe Glu Cys Lys Asn His Val Cys Ile Pro
            3845                3850                3855
Pro Tyr Trp Lys Cys Asp Gly Asp Asp Asp Cys Gly Asp Gly Ser Asp
            3860                3865                3870
Glu Glu Leu His Leu Cys Leu Asp Val Pro Cys Asn Ser Pro Asn Arg
            3875                3880                3885
Phe Arg Cys Asp Asn Asn Arg Cys Ile Tyr Ser His Glu Val Cys Asn
            3890                3895                3900
Gly Val Asp Asp Cys Gly Asp Gly Thr Asp Glu Thr Glu Glu His Cys
3905                3910                3915                3920
Arg Lys Pro Thr Pro Lys Pro Cys Thr Glu Tyr Glu Tyr Lys Cys Gly
            3925                3930                3935
Asn Gly His Cys Ile Pro His Asp Asn Val Cys Asp Asp Ala Asp Asp
            3940                3945                3950
Cys Gly Asp Trp Ser Asp Glu Leu Gly Cys Asn Lys Gly Lys Glu Arg
            3955                3960                3965
Thr Cys Ala Glu Asn Ile Cys Glu Gln Asn Cys Thr Gln Leu Asn Glu
```

```
            3970             3975             3980
Gly Gly Phe Ile Cys Ser Cys Thr Ala Gly Phe Glu Thr Asn Val Phe
3985             3990             3995             4000

Asp Arg Thr Ser Cys Leu Asp Ile Asn Glu Cys Glu Gln Phe Gly Thr
            4005             4010             4015

Cys Pro Gln His Cys Arg Asn Thr Lys Gly Ser Tyr Glu Cys Val Cys
            4020             4025             4030

Ala Asp Gly Phe Thr Ser Met Ser Asp Arg Pro Gly Lys Arg Cys Ala
            4035             4040             4045

Ala Glu Gly Ser Ser Pro Leu Leu Leu Pro Asp Asn Val Arg Ile
            4050             4055             4060

Arg Lys Tyr Asn Leu Ser Ser Glu Arg Phe Ser Glu Tyr Leu Gln Asp
4065             4070             4075             4080

Glu Glu Tyr Ile Gln Ala Val Asp Tyr Asp Trp Asp Pro Lys Asp Ile
            4085             4090             4095

Gly Leu Ser Val Val Tyr Tyr Thr Val Arg Gly Glu Gly Ser Arg Phe
            4100             4105             4110

Gly Ala Ile Lys Arg Ala Tyr Ile Pro Asn Phe Glu Ser Gly Arg Asn
            4115             4120             4125

Asn Leu Val Gln Glu Val Asp Leu Lys Leu Lys Tyr Val Met Gln Pro
            4130             4135             4140

Asp Gly Ile Ala Val Asp Trp Val Gly Arg His Ile Tyr Trp Ser Asp
4145             4150             4155             4160

Val Lys Asn Lys Arg Ile Glu Val Ala Lys Leu Asp Gly Arg Tyr Arg
            4165             4170             4175

Lys Trp Leu Ile Ser Thr Asp Leu Asp Gln Pro Ala Ala Ile Ala Val
            4180             4185             4190

Asn Pro Lys Leu Gly Leu Met Phe Trp Thr Asp Trp Gly Lys Glu Pro
            4195             4200             4205

Lys Ile Glu Ser Ala Trp Met Asn Gly Glu Asp Arg Asn Ile Leu Val
            4210             4215             4220

Phe Glu Asp Leu Gly Trp Pro Thr Gly Leu Ser Ile Asp Tyr Leu Asn
4225             4230             4235             4240

Asp Arg Ile Tyr Trp Ser Asp Phe Lys Glu Asp Val Ile Glu Thr Ile
            4245             4250             4255

Lys Tyr Asp Gly Thr Asp Arg Arg Val Ile Ala Lys Glu Ala Met Asn
            4260             4265             4270

Pro Tyr Ser Leu Asp Ile Phe Glu Asp Gln Leu Tyr Trp Ile Ser Lys
            4275             4280             4285

Glu Lys Gly Glu Val Trp Lys Gln Asn Lys Phe Gly Gln Gly Lys Lys
            4290             4295             4300

Glu Lys Thr Leu Val Val Asn Pro Trp Leu Thr Gln Val Arg Ile Phe
4305             4310             4315             4320

His Gln Leu Arg Tyr Asn Lys Ser Val Pro Asn Leu Cys Lys Gln Ile
            4325             4330             4335

Cys Ser His Leu Cys Leu Leu Arg Pro Gly Gly Tyr Ser Cys Ala Cys
            4340             4345             4350

Pro Gln Gly Ser Ser Phe Ile Glu Gly Ser Thr Thr Glu Cys Asp Ala
            4355             4360             4365

Ala Ile Glu Leu Pro Ile Asn Leu Pro Pro Cys Arg Cys Met His
            4370             4375             4380

Gly Gly Asn Cys Tyr Phe Asp Glu Thr Asp Leu Pro Lys Cys Lys Cys
4385             4390             4395             4400
```

-continued

```
Pro Ser Gly Tyr Thr Gly Lys Tyr Cys Glu Met Ala Phe Ser Lys Gly
            4405            4410            4415

Ile Ser Pro Gly Thr Thr Ala Val Ala Val Leu Leu Thr Ile Leu Leu
            4420            4425            4430

Ile Val Ile Gly Ala Leu Ala Ile Ala Gly Phe Phe His Tyr Arg
        4435            4440            4445

Arg Thr Gly Ser Leu Leu Pro Ala Leu Pro Lys Leu Pro Ser Leu Ser
    4450            4455            4460

Ser Leu Val Lys Pro Ser Glu Asn Gly Asn Gly Val Thr Phe Arg Ser
4465            4470            4475            4480

Gly Ala Asp Leu Asn Met Asp Ile Gly Val Ser Gly Phe Gly Pro Glu
            4485            4490            4495

Thr Ala Ile Asp Arg Ser Met Ala Met Ser Glu Asp Phe Val Met Glu
            4500            4505            4510

Met Gly Lys Gln Pro Ile Ile Phe Glu Asn Pro Met Tyr Ser Ala Arg
        4515            4520            4525

Asp Ser Ala Val Lys Val Val Gln Pro Ile Gln Val Thr Val Ser Glu
        4530            4535            4540

Asn Val Asp Asn Lys Asn Tyr Gly Ser Pro Ile Asn Pro Ser Glu Ile
4545            4550            4555            4560

Val Pro Glu Thr Asn Pro Thr Ser Pro Ala Ala Asp Gly Thr Gln Val
            4565            4570            4575

Thr Lys Trp Asn Leu Phe Lys Arg Lys Ser Lys Gln Thr Thr Asn Phe
            4580            4585            4590

Glu Asn Pro Ile Tyr Ala Gln Met Glu Asn Glu Gln Lys Glu Ser Val
        4595            4600            4605

Ala Ala Thr Pro Pro Pro Ser Pro Ser Leu Pro Ala Lys Pro Lys Pro
    4610            4615            4620

Pro Ser Arg Arg Asp Pro Thr Pro Thr Tyr Ser Ala Thr Glu Asp Thr
4625            4630            4635            4640

Phe Lys Asp Thr Ala Asn Leu Val Lys Glu Asp Ser Glu Val
            4645            4650            4655
```

NUCLEIC ACIDS ENCODING HUMAN CALCIUM SENSOR PROTEIN

This application is a continuation-in-part of U.S. Ser. No. 08/344,836 filed Nov. 23, 1994, now abandoned, which is a continuation-in-part of PCT/SE94/00483 filed May 24, 1994 and which designated the U.S.

BACKGROUND OF THE INVENTION

The present invention relates to a cDNA clone encoding a human calcium sensor protein of parathyroid, placental, and kidney tubule cells.

In WO 88/03271 there is described monoclonal antiparathyroid antibodies identifying a parathyroid cell membrane-bound calcium receptor or sensor, crucially involved in calcium regulation of the parathyroid hormone (PTH) release (1,2). The receptor function is essential for maintenance of normal plasma calcium concentrations, and reduced receptor expression within proliferating parathyroid cells of patients with hyperparathyroidism (HPT) results in calcium insensitivity of the PTH secretion and variably severe hypercalcemia (3–6). Reactivity with the antiparathyroid antibodies was also demonstrated for proximal kidney tubule cells and cytotrophoblast cells of the human placenta, and the cytotrophoblasts were demonstrated to exhibit an almost parathyroid-identical regulation of cytoplasmic calcium $[Ca^{2+}i]$(7,8). The antibody-reactive structure was found to exert calcium sensing function also in the cytotrophoblasts, and as these cells constitute part of the syncytium, the calcium sensor was suggested to be actively involved in the calcium homeostasis of the fetus (7,8). It was proposed that the antibody-reactive structure of the proximal kidney tubule cells exerts a similar calcium sensing function, and that the calcium sensor, thus, plays a more universal role in calcium regulation via different organ systems (1,7,9,10).

On HPT patients with hypercalcemia, surgery is-performed to remove one or more of the parathyroid glands. It would be greatly desirable to have alternatives to this surgical procedure as HPT has proven to be a very common disorder and surgery is a relatively costly procedure and sometimes even entails some risks for the patients.

The calcium sensor/receptor has been revealed as a 500 kDa single chain glycoprotein (7). However, the amino acid sequence as well as the corresponding DNA sequences thereof are hitherto unknown.

SUMMARY OF THE INVENTION

Therefore, an object of the present invention was to provide sufficient structural data of the calcium sensor/receptor to enable complete characterization thereof.

In one embodiment, the present invention provides the complete amino acid sequence of the human calcium sensor protein and nucleic acid probes for identifying other novel calcium sensor proteins.

Another object is to use said structural data to design novel treatment methods as well as compounds and compositions for treating calcium related disorders.

In other embodiments, the present invention provides identification of peptide regions within the calcium sensor protein cytoplasmic domain which are homologous to SH2 and SH3 binding motifs involved in signal transduction pathways.

Two important human diseases associated with perturbations of the calcium ion homeostasis are hyperthyroidism and osteoporosis. Thus, in one embodiment cells expressing the calcium sensor protein or a fragment thereof or comprising the cDNA encoding the calcium sensor protein of the present invention may be utilized in an assay to identify molecules which block or enhance the activity of the calcium sensor protein, including signal transduction pathways associated with the activity of the sensor. These molecules will be useful in the treatment of mammalian pathological conditions associated with perturbations in the levels of PTH, vitamins D3 production, estrogen, osteoclast activity or osteoblast activity (therefore, bone resorption and/or formation), calcium secretion and calcium ion homeostasis.

The present invention describes the isolation and characterization of cDNA clones encoding the calcium sensor/receptor in human placenta and Northern blots verifying the presence of the corresponding mRNA within the parathyroid and kidney. Close sequence similarity between the calcium sensor and a rat Heymann nephritis antigen, gp330 (11, 67), suggests that the common calcium sensor of the placenta, the parathyroid and kidney tubule is related to this antigen, represents the human homologue of gp330, and belongs to a family of large glycoproteins with receptor function and calcium binding ability. Therefore, a further object of this invention is to provide diagnostic assays and therapeutic methods based on human gp330.

BRIEF DESCRIPTION OF THE DRAWINGS

FIG. 2. Sequences of two Lys-C peptides (SEQ ID Nos. 1 and 2) isolated by HPLC of the calcium-sensor protein.

FIG. 3. Partial nucleotide sequence (SEQ ID No. 3) and deduced amino acid sequence (SEQ ID No. 4) of the-cDNA clone, pCAS-2, encoding part of the calcium-sensor protein. Portions of the deduced amino acid sequence identical to the peptides 292 and 293 are underlined.

FIG. 4. Alignment of the amino acid sequence of the calcium-sensor protein (SEQ ID No. 4) to corresponding portions of the Heymann antigen (HEYMANN, SEQ ID No. 5), low density lipoprotein receptor (LDL-RC, SEQ ID No. 6), and LDL related receptor protein (LDLRRP, SEQ ID No. 7). Stars denote residues identical between the calcium sensor protein and any of the other sequences. X denotes a position in the Heymann antigen sequence where identity has not been published.

FIG. 6. Complete nucleotide (SEQ ID No. 11) and amino acid (SEQ ID No. 12) sequence of the human calcium sensor 2.8 kb cDNA clone. The transmembrane domain of the sensor is shown in bold type. The three SH3 binding regions are underlined or overlined and the SH2 binding region is shown in strikethru.

FIG. 7. Amino acid sequence of the calcium sensor cytoplasmic domain (SEQ ID No. 13) and comparison of the three calcium sensor SH3 binding regions (SEQ ID Nos. 14–16) to known SH3 binding motifs (SEQ ID Nos. 20–37).

FIG. 9. Comparison of the calcium sensor SH2 binding region (SEQ ID No. 19) with amino acid sequence requirements necessary for interaction with the SH2 region of the p85 regulatory subunit of PI3K (SEQ ID Nos. 38–78).

FIG. 10. Complete nucleotide sequence encoding the human calcium sensor protein (SEQ ID No. 83).

DETAILED DESCRIPTION OF PREFERRED EMBODIMENTS

Figure 1:
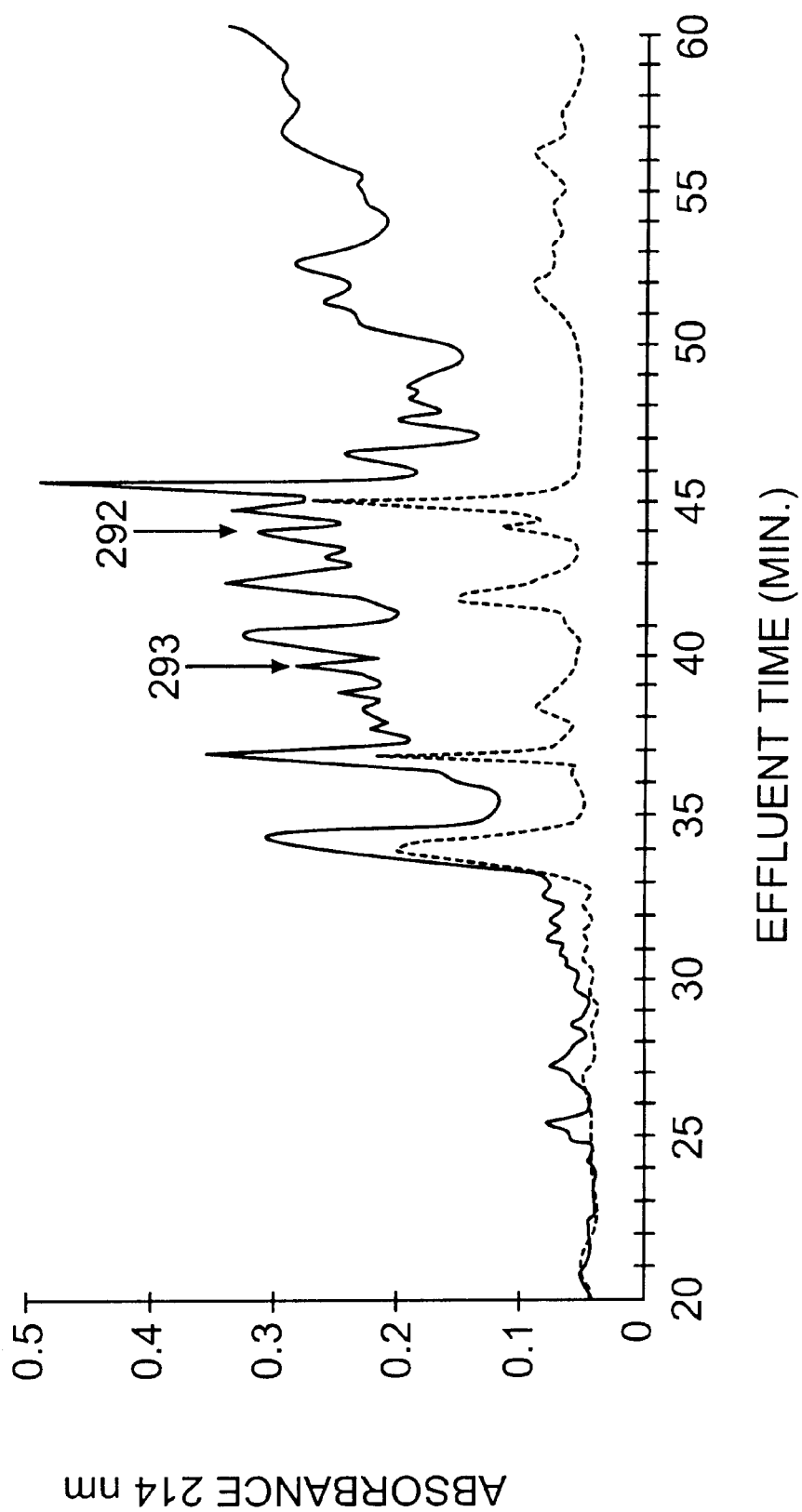
FIG. 1. Isolation by HPLC of peptides obtained after digestion of the calcium sensor protein with Lys-C endoprotease (solid line). Dashed line represents the chromatography of an identical reaction where the calcium-sensor was omitted. The flow rate was kept at 100 µl/min. Two peptide fractions which gave easily interpretable sequences are denoted by arrows.

Unless indicated otherwise herein, the following terms have the indicated meanings.

The term "polypeptide" means a linear array of amino acids connected one to the other by peptide bonds between the α-amino and carboxy groups of adjacent amino acids.

"Substantially purified" is used herein to mean "substantially homogeneous", which is defined as a material which is substantially free of compounds normally associated with it in its natural state (e.g., other proteins or peptides, carbohydrates, lipids). "Substantially purified" is not meant to exclude artificial or synthetic mixtures with other compounds. The term is also not meant to exclude the presence of impurities which do not interfere with biological activity, and which may be present, for example, due to incomplete purification or compounding with a pharmaceutically acceptable preparation.

The term "biologically active polypeptide" means the naturally occurring polypeptide per se as well as biologically active analogues thereof, including synthetically produced polypeptides and analogues thereof, as well as natural and pharmaceutically acceptable salts and pharmaceutically acceptable derivatives thereof. The term "biologically active polypeptide" also encompasses biologically active fragments thereof, as well as "biologically active sequence analogues" thereof. Different forms of the peptide may exist. These variations may be characterized by difference in the nucleotide sequence of the structural gene coding for proteins of identical biological function.

The term "biologically active sequence analogue" includes nonnaturally occurring analogues having single or multiple amino acid substitutions, deletions, additions, or replacements. All such allelic variations, modifications, and analogues resulting in derivatives which retain one or more of the native biologically active properties are included within the scope of this invention.

In this application, nucleotides are indicated by their bases using the following standard one-letter abbreviations:
Guanine G
Adenine A
Thymine T
Cytosine C
Unknown N In this application, amino acid residues are indicated using the following standard one-letter abbreviations:
Alanine A
Cysteine C
Aspartic Acid D
Glutamic Acid E
Phenylalanine F
Glycine G
Histidine H
Isoleucine I
Lysine K
Leucine L
Methionine M
Asparagine N
Proline P
Glutamine Q
Arginine R
Serine S
Threonine T
Valine V
Tryptophan W
Tyrosine Y
Unknown X The term "amino acid" as used herein is meant to denote the above recited natural amino acids and functional equivalents thereof.

Figure 6:
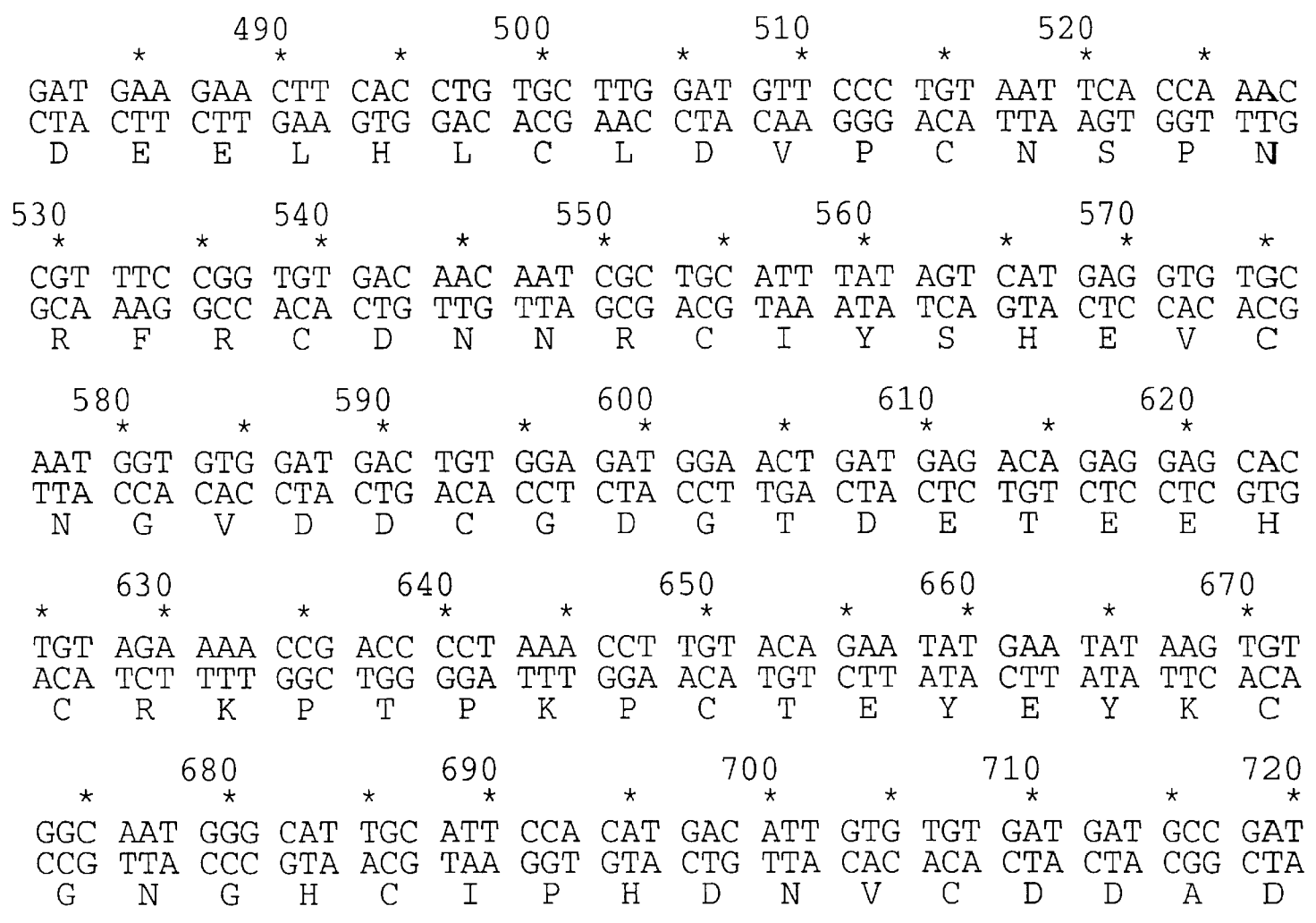

This invention provides an isolated nucleic acid molecule encoding the calcium sensor protein and having a coding sequence comprising the sequence shown in FIG. 3 (SEQ ID No. 3), FIG. 6 (SEQ ID No. 11), or FIG. 10 (SEQ ID No. 83).

Furthermore, this invention provides a vector comprising an isolated nucleic acid molecule encoding the calcium sensor protein or a fragment thereof which encodes functional regions of the sensor.

Moreover, the invention provides a method of preparing calcium sensor protein which comprises inserting a nuleic acid encoding the calcium sensor or a fragment thereof in a suitable vector, inserting the resulting vector in a suitable host cell, recovering the calcium sensor protein produced by the resulting cell, and purifying the calcium sensor protein so recovered. This method for preparing a calcium sensor protein or fragment thereof uses recombinant DNA technology methods which are well known in the art. Alternatively, the calcium sensor protein or a fragment thereof may be prepared using standard solid phase methodology of peptide synthesis.

The present invention also provides antisense nucleic acids which can be used to down regulate or block the expression of the calcium sensor protein either in vitro, ex vivo or in vivo. The down regulation of gene expression can be made at both translational or transcriptional levels. Antisense nucleic acids of the invention are more preferentially RNA fragments capable of specifically hybridizing with all or part of the sequence of SEQ ID. No. 3 or FIG. 6 (SEQ ID No. 11) or the corresponding messenger RNA. These antisense can be synthetic oligonucleotides prepared based on the sequence of SEQ ID No. 3 or FIG. 6(SEQ ID No. 11), optionally modified to improve their stability of selectivity, as disclosed for instance in EP 92574. They can also be DNA sequences whose expression in the cell produces RNA complementary to all or part of the calcium sensor protein mRNA. These antisenses can be prepared by expression of all or part of the sequence of SEQ ID No. 3, FIG. 6 (SEQ ID No. 11) of SEQ ID No. 83 in the opposite orientation (EP 140 308).

Material and Methods

Tissue specimens. Samples of human parathyroid glands were obtained at surgery of patients with primary HPT. Other human tissue specimens (kidney, epididymis, liver, pancreas, adrenal gland, small gut, spleen, lung and striated muscle) were sampled from organs removed at surgery.

Human placental tissue was collected in conjunction with uncomplicated pregnancies at full term. All specimens were immediately quick-frozen in isopentane and stored at −70° C.

Isolation of the calcium sensor protein from human placenta. The 500 kDa calcium sensor protein was isolated and purified, from altogether 25 human placentas, by immunosorbent and ion exchange chromatographies, following a previously described protocol (7). The procedure utilizes two different monoclonal antiparathyroid antibodies (1,7), E11 and G11, known to bind different epitopes of the calcium sensing protein; E11 has displayed no functional effect, while G11 efficiently blocks calcium regulation in both parathyroid and placental cells (1,7). After purification, the calcium sensor protein preparation was subjected to gel chromatography on a Zorbax GF25 gel column (9.2×250 mm), prior to enzymatic digestion.

The biologically active calcium sensor protein of the present invention has been isolated as described. It can also be prepared by chemical synthesis in a recombinant DNA biosystem. Biologically active fragments of the calcium sensor protein can also be prepared using synthetic or recombinant technologies which are known in the art.

Cleavage and sequence determination of isolated peptides. Cleavage of the 500 kDa protein with endoprotease Lys C from *Achromobacter lyticus* generated peptides, which were subjected to separation on a Brownlee microbore $C_4$ column (2.2×30 mm), equilibrated in 5% acetonitrile in 0.02% trifluoroacetic acid. A linear gradient of 5 to 60% acetonitrile in 0.02% trifluoroacetic acid was employed for peptide elution, monitored at 214 nm using Waters 990 diod-array detector (Millipore Corporation, Millford, Mass.). Amino terminal sequences of the peptides were determined in an ABI 470A gas-phase sequenator, equipped with an ABI 120A PTH-amino acid chromatograph (Applied Biosystems, Foster City, Calif., USA).

Oligonucleotide synthesis. oligonucleotides were synthesized using an ABI 381 oligonucleotide synthesizer (Applied Biosystems). The following oligonucleotide mixture was utilized as a probe for screening of the placental cDNA library:

```
                                         (SEQ ID No. 8)
     CCA ATA IAG CTG ATC CTC AAA GAT ATC IAG
         G       G       G       G
     IGA ATA IGG ATT CAT IGC
         G       G
```

The following two oligonucleotides were synthesized for use in PCR reactions:

```
GCG GAATTC GTA ATG CAA CCA GAC GG   (SEQ ID NO. 9)
           C       G   C   T
           G           G
           T           T

ATAGGAATC CTG ATC CTC AAA AAT ATC   (SEQ ID NO. 10)
          G   T   G   G   G
                          T
```

The first nine nucleotides contain an EcoR I. and a BamH I site, respectively, and the remaining nucleotides correspond to amino acid residues 1 to 6 of peptides 293 and to residues 9 to 14 of peptide 292.

Screening of a placental cDNA library with a mixed oligonucleotide probe. A placental 1 gt 11 cDNA library (Clontech, Ca., USA) was plated out to a density of approximately $2 \times 10^5$ plaques within a 20×25 cm agar plate. Replicate filters (Hybond-N+, Amersham) of ten plates were prehybridized in 5×SSPE (SSPE; 120 mM NaCl, 8 mM $NaH_2PO_4$, 0.8 mM EDTA, pH 7.4), 5×Denhart's solution (12), 0.5% SDS, 20 µg/ml single stranded salmon sperm DNA (Sigma Chemical Co., S:t Louis, Ohio). The mixed oligonucleotide probe, endlabeled with $\gamma$-[$^{32}$p]-ATP and polynucleotide kinase (Amersham), was added to the hybridization mixture ($30 \times 10^6$ cpm in 50 ml), and hybridization was carried out over night at 42° C. The filter was washed twice in 2×SSPE and once in 0.1×SSPE, exposed to an autoradiography screen and analysed by a phosphorimager (Molecular Dynamics, Image Count S.W, Sun Valley Calif.).

PCR reaction. Part of the $\lambda$ gt 11 cDNA clone CAS-1 was amplified by PCR using two degenerated probes corresponding to portions of peptides 292 and 293. The following conditions were used: 170 ng template DNA, 1 pmol of each oligonucleotide mixture as primers, dNTP 3mM, Taq-polymerase 0.75 u. The reaction was carried out in 20 µl of 10 mM Tris-HCl, pH 8.0, 1.5 mM $MgCl_2$, 50 mM KCl in a Perkin-Elmer 9600 PCR-machine (Perkin-Elmer, Norwalk, USA). Two cycles of denaturation at 94° C. for 2 min. annealing at 47° C. for 1 min and extension at 72° C. for 1 min 30 sec were followed by 33 cycles of 94° C. for 1 min. 54° C. for 45 sec. 72° C. for 1 min and a final extension at 72° C. for 10 min.

Screening of a placental cDNA library with a PCR-fragment as probe. A placental $\lambda$ ZAP-II cDNA library, was screened with the PCR-fragment from the cDNA clone CAS-1 labeled by random priming as the probe. The screening was carried out as above. $2 \times 10^6$ plaques distributed on ten 20×25 cm agar plates were screened.

Nucleotide sequence determination. The insert of the phage clone CAS-2 was released from the phage vector in the Bluescript+ vector using a helper phage (Stratagene, La Jolla, Calif.). Nucleotide sequence reactions were carried out according to the cycle sequencing procedure, utilizing a kit from Applied Biosystems. Sequences were analyzed in an ABI 373 A DNA sequenator using the Data Collection Program VIII software (Applied Biosystems). Completion of the CAS-2 2.8 kb cDNA sequence was accomplished by the dideoxynucleotide chain-termination method with Sequenase (United States Biochemical) and is shown in FIG. 6 (SEQ ID No. 11). Multiple sequencing analyses were performed on both strands of CAS-2 to confirm the sequence. Amino acid sequence deduced from the cDNA sequence was analyzed by a Macvector DNA/RNA software analysis package (Macintosh).

Database search. The EMBL-31 database in the Intelligenetics format (Intelligenetics Rel.5.4), was searched for sequence similarities to the placental cDNA sequence using the FAST DB algorithm (13).

Imminostaining and Northern blot. Immunohistochemical studies were performed on acetone-fixed, 6 µm thick frozen sections, utilizing the monoclonal antiparathyroid antibodies E11 and G11, at concentrations of 5 µg/ml, together with a mouse peroxidase antiperoxidase technique on human placental, parathyroid, kidney, and epididymis specimens as well as on the other human tissues—see above (1,7). Monoclonal antibodies to collagen-type II were used as negative controls (14).

Total RNA was extracted from tissue samples by the acid phenol/chloroform method. For Northern blot analysis approximately 10 µg of total RNA was electrophoresed in a 1.5%/37% agarose/formaldehyde gel, blotted onto nylon membranes (Qiabrane, Diagen GmbH, Dusseldorf, Germany) and probed with the 2.3 kb clone (see results) labeled by the random priming method.

Hybridizations were performed at 42° C. for 18–24 h in 50% formamide, 4×saline sodium citrate (SSC; 300 mM NaCl, 30 mM Na-citrate, pH 7.0), 2×Denhart's solution, 10% dextran sulfate (Kabi-Pharmacia, Uppsala, Sweden) and 100 µg/ml salmon sperm DNA. Filters were washed at a final stringency of 1×SSC/0.1% SDS for 30 sin at 42° C., and exposed within a phosphorimager as above.

CAS Peptide Binding Analysis: A peptide corresponding to one putative CAS SH3 binding region (ATPPPSPSLPAKPKPPSRR) (SEQ ID No. 18) was synthesized on an ABI model 430A synthesizer using FastMoc$^{tm}$ chemistry. The peptide was HPLC purified and analyzed by mass spectroscopy. 5 mg of the peptide was coupled to 500 ul of Amino Link (Pierce) agarose as described by the supplier. Efficiency of coupling was checked by RP-HPLC of peptide solution before and after coupling and spectrophotometrically at a wavelength of 220 nm. Both methods indicated a coupling efficiency of >70%. The coupled peptide was reacted with 5 ug aliquots of various GST-SH3 fusion proteins at room temperature for 1 hour before the resin was washed extensively with TTBS. The resin was boiled in SDS loading dye and electrophoresed on an SDS-PAGE gel. Binding ability of the various SH3 proteins for the peptide was judged by the relative intensity of the Coomassie blue-stainable bands on the SDS gel. GST protein alone was used alone as a control.

Expression and Purification of GST-SH3 fusion Proteins: Various GST-SH3-containing fusion clones were kind gifts from Dr. I. Gout, Ludwig Inst. for Cancer Research, London, UK. The fusion proteins were all produced by inducing their expression in XL1-blue *E. coli* using 1 mM IPTG. Cells containing the fusion proteins were sonicated in PBS containing 10 mM EDTA and 1% Triton-X 100. After pelleting cell debris, the cleared lysate was applied to a glutathione-Sepharose column (Pharmacia), and the bound fusion protein was eluted with 10 mM reduced glutathione in 50 mM Tris pH 8.0. These purified fusion proteins were then dialyzed extensively against PBS before being used in all subsequent experiments. Protein was quantified by measuring the absorbance at 280 nm followed by characterization by SDS polyacrylamide gel electrophoresis.

RESULTS

Isolation of the Calcium Sensor Protein, Peptide Cleavage and Sequence Determination.

The calcium sensor protein was purified from placental tissue by means of Pectin chromatography, immunosorbent chromatography utilizing the immobilized monoclonal antiparathyroid antibodies, and finally ion exchange chromatography (1,7). The same antibodies were used in a sandwich ELISA to monitor the purification (7). In order to avoid contamination with low molecular peptides, the whole final preparation, consisting of 200 µg of the 500 kDa protein chain (7), was made 6M with regard to guanidine-HCl and applied to a gel chromatography column, equilibrated with 2M guanidine-HCl, 0.1M Tris-Cl, pH 8.5. The column was eluted with the same buffer. Virtually all protein material emerged close to the void volume at the expected position for a protein with a molecular mass of 500 kDa. Separate fractions containing this material were combined and endoproteinase Lys C (1 µg) was added. The digestion was allowed to proceed over night at 37° C. The fragmented protein was reduced by incubation with 0.1% β-mercaptoethanol at 37° C. for 30 min and subsequently alkylated with 4-vinyl pyridine (0.3%) at room temperature for 2 h. The peptide mixture was then applied to a reversed phase C4 column equilibrated in 5% acetonitrile in 0.2% trifluoroacetic acid. Peptides were eluted by a linear gradient of 5–60% acetonitrile in 0.02% trifluoracetic acid (FIG. 1). Due to the large number of peptides, the elution pattern was complex. Several peptide fractions were sequenced in a gas phase sequenator and easily interpretable sequences were obtained for two fractions (FIG. 2, SEQ ID Nos. 1 and 2).

Isolation of a cDNA Clone Encoding the 500 kDa Calcium Sensor.

An oligonucleotide mixture (48 bp) was constructed to encode amino acid residues 2 to 17 of the sequenced peptide 292. To reduce the complexity of the oligonucleotide mixture, five inosine bases were inserted at degenerated positions where no guidance could be obtained from the codon usage in humans. At nine positions, where two bases were possible, one of the bases was suggested with a likelihood exceeding 70% from codon usage, and was therefore used in the oligonucleotide mixture.

The mixed oligonucleotide was radioactively labelled and used as a probe to screen a human placental λ gt 11 cDNA library. Approximately 2×10$^6$ plaques were screened and a single positive clone, CAS-1, was found. The insert of this clone was estimated to 2.3 kb, by restriction mapping. To obtain a recognizable sequence of the clone in a rapid way, an attempt was made to PCR amplify part of the sequence using degenerated oliogonucleotides corresponding to part of peptides 292 and 293 as primers. A distinct DNA fragment of approximately 430 bp was obtained assuming that the peptide 292 is located carboxy-terminal to peptide 293. The fragment was partially sequenced using the oligonucleotide mixture corresponding to peptide 293 as the primer. In one reading frame from the obtained sequence, the sequence VGRHI could be deduced, in excellent agreement with the carboxyterminal 5 amino residues of peptide 293. To obtain a clone with a larger insert a human placental λ ZAP-II cDNA library reported to contain clones with large inserts was screened with the PCR fragment as the probe. From 2×10$^6$ plaques a single clone, CAS-2, was found. The insert of this clone, estimated to 2.8 kb, was released in the Bluescript+vector, using a helper phage. Part of the insert of this clone, pCAS-2, was sequenced using synthetic oligonucleotides as primers (FIG. 3, SEQ ID No. 3). An open reading frame was found containing both peptide 292 and 293. There was perfect agreement between the peptide sequences and the predicted amino acid sequence (SEQ ID No. 4) from the cDNA clone. The complete sequence of the 2.8 kb CAS-2 is shown in FIG. 6 (SEQ ID No. 11). The CAS-2 sequence was extended using standard methodology. All nucleic acid probes were random-primed DNA fragments generated by PCR amplification (Perkin Elmer/Cetus) of appropriate CAS cDNA clones. Probe regions were chosen from existing clones such that each subsequent cDNA library screen should yield overlapping 5'-extended contiguous clones. An extended calcium sensor sequence is shown in SEQ ID No. 17 and the complete human calcium sensor sequence in shown in FIG. 10 (SEQ ID Nos. 83 and 84).

The 500 kDa Placental Calcium Sensor Belongs to the LDL-receptor Superfamily.

Figure 11:
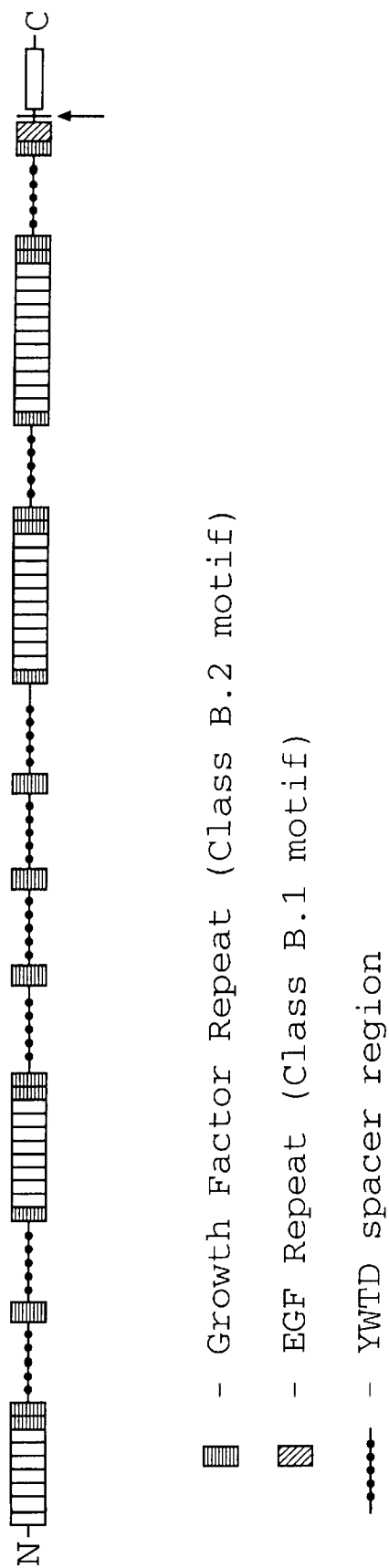
FIG. 11. Structure of human gp330, including the EGF repeat, growth factor repeats and YWTD spacer regions. N depicts the amino terminus of the protein and C the carboxyl-terminus. The arrow indicates the location of the transmembrane region.

A search in a database with the predicted amino acid sequence from FIG. 3 (SEQ ID No 3) revealed that the placental 500 kDa protein is homologous to receptors belonging to the LDL-receptor superfamily. The highest similarity was found with the rat Heymann nephritis antigen (11, 67). FIG. 4 shows an alignment of placental 500 kDa protein sequence to the sequence of the Heymann antigen (SEQ ID No. 5) as well as to two other members of the same protein superfamily, the LDL-receptor (SEQ ID No. 6) and the LDLreceptor-related protein (identical to the α2-macroglobulin receptor, (11,15,16), SEQ ID No. 7). The sequence identity between the placental calcium-sensor and the Heymann antigen gp330 was estimated to be 82% in the region of comparison (236 amino acid residues). The complete sequence of the human calcium sensor protein is shown in FIG. 10. Overall, the identity between rat gp330 and the human homolog is 77%. The structure of human gp330 is shown in FIG. 11. The protein is 4654 amino acids in length and comprises an N-terminal signal peptide of 25 amino acids, a 4397 amino acid extracellular domain, a transmembrane region of 23 amino acids and a C-terminal domain of 209 amino acids. As shown in FIG. 11, the structure of human gp330 closely correlates with that of the rat homolog (FIG. 3 of ref. 67).

Immunohistochemistry and Northern Blot.

The close similarity between the placental 500 kDa calcium-sensor protein and the rat Heymann nephritis antigen prompted the expanded immunohistochemical investigation of the present study. The antiparathyroid antibodies (E11 and G11) were found to stain not only parathyroid, placental and proximal kidney tubule cells but also epididymal cells, as previously demonstrated for antibodies reactive with the Heymann antigen (17–20).

Figure 5:
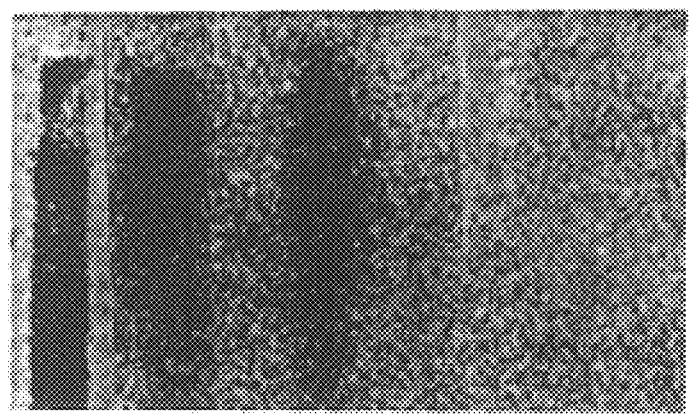
FIG. 5. Northern blot analysis of total RNA from parathyroid adenoma (1), kidney (2), liver (3), placenta (4), pancreas (5), adrenal gland (6), small gut (7). Filters were hybridized with the 2.8 kb pCAS-2 insert probe, and reactions visualized by a phosphorimager. Locations of 28S and 18S ribosomal RNA are indicated.

Northern blot analysis of total RNA (approximately 10 μg/lane) from human kidney, placenta and parathyroid glands with the identified 2.8 kb clone as the probe, revealed one major hybridizing RNA species of approximately 15,000 bases in all these tissues (FIG. 5). Human liver, pancreas, adrenal gland, and small gut (FIG. 5) as well as spleen, lung and striated muscle (not shown) lacked hybridizing species.

Identification of SH2 and SH3 Binding Regions in the Cytoplasmic Domain of the Calcium Sensor:

Src-homology regions 2 and 3 (SH2 and SH3) are conserved sequence motifs consisting of approximately 100 and 60 amino acid residues, respectively, and are found in many eukaryotic proteins with diverse function (42–44). SH3 domains have been identified in several cytoskeleton-associated proteins, such as p80/p85, myosin1b, spectrin, neutrophil NADPH oxidase-associated proteins p47 and p67, and in several yeast proteins important for morphogenesis (i.e., Bem1p and ABP-1), mating (FUS1) or for regulation of ras activity (cdc25 and ste6 (for review see Mussachio et al. (45)). The observation that many SH3-containing proteins are cytoskeleton-associated led to the suggestion that SH3 domains play a role in multimeric protein complex formation at or near cytoplasmic membranes. Some proteins that contain both SH2 and SH3 domains perform the function of adaptor molecules by joining activated receptor tyrosine kinases with p21 ras guanine nucleotide-releasing protein (GNRP). For example, Grb2 and its homologues bind to phosphotyrosine on activated membrane-anchored receptor tyrosine kinases through their SH2 domain and to SOS through their amino- and carboxyterminal SH3 domains (46–50). These processes lead to translocation of SOS to the plasma membrane where ras proteins are interacted with and consequently activated. Thus, SH2/SH3-containing and SH2/SH3-binding proteins are involved in a highly conserved signal transduction pathways from activated receptors.

Figure 8:
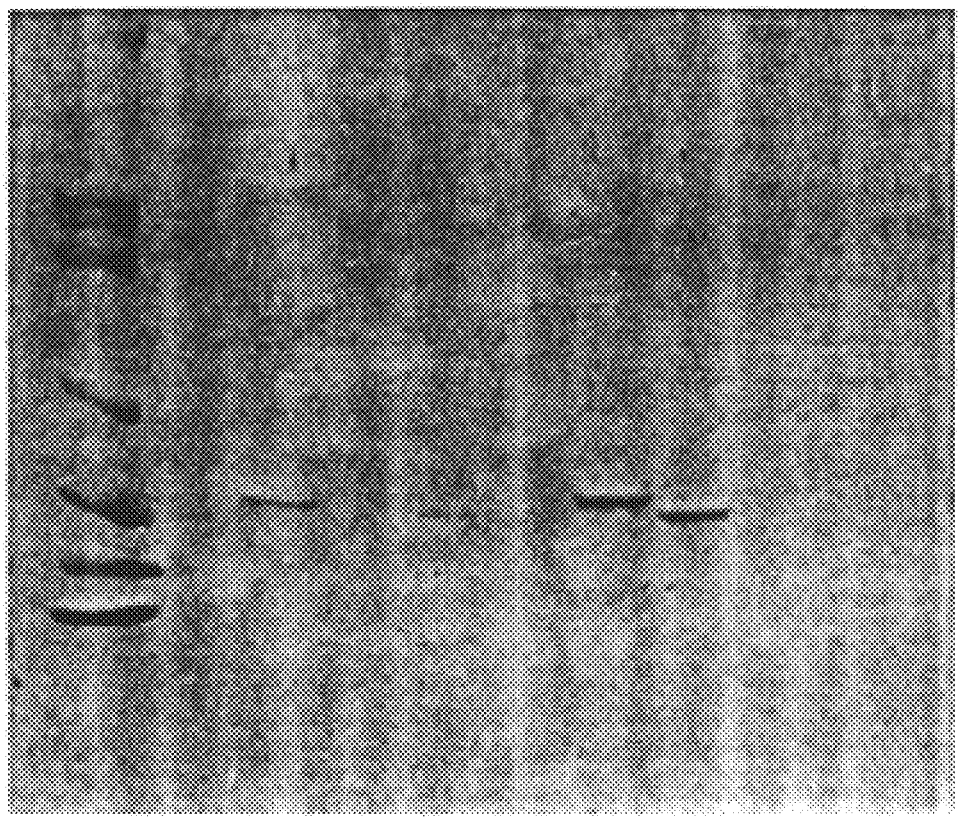
FIG. 8. Comparison of relative binding strengths between a calcium sensor SH3 binding region and various GST fusion proteins comprising an SH3 domain.

Complete nucleic acid sequencing and translation of the 2.8 kb human cDNA clone CAS-2 (FIG. 6) (SEQ ID Nos. 11 and 12) demonstrate the existence of at least three potential SH3 binding regions denoted as CAS-PEP1 (SEQ ID No. 14), CAS-PEP2 (SEQ ID No. 15), and CAS-PEP3 (SEQ ID No. 16) (FIG. 7). All three of these CAS-2 cytoplasmic peptide regions have the required consensus sequence of a SH3-binding region, which is shown together with the CAS peptides in FIG. 7 (53). Further support that the cytoplasmic domain of CAS-2 binds SH3 regions is shown in the evidence in FIG. 8. A region of the CAS-2 cytoplasmic domain (ATPPPSPSLPAKPKPPSRR) (SEQ ID No. 18) that included CAS-PEP1 (PSLPAKP, FIG. 7) was synthesized. The peptide was incubated with various purified GST-SH3 fusion proteins and the relative binding strengths of the fusion proteins was assayed by SDS-PAGE (FIG. 8). The data clearly indicate that several of the SH3-region containing proteins had an affinity for the peptide containing CAS-PEP1, with the following relative order of decreasing affinities: LANE 6: SH3-PI3K (SH3 of p85 subunit of phosphoinositol-3 kinase, (54,55))>LANE 7: SH3-PLC-gamma, (phospholipase-C gamma, (56))>LANE 2: SH3-FYN (src-family soluble tyrosine kinase, (57), >LANE 4: SH3-GRB2, (growth factor receptor binding protein N-terminal SH3) and LANE 5 (C-terminal SH3 of GRB2) (58,59).

Significantly, all of the positive reacting SH3-containing proteins shown in FIG. 8 are intimately associated with signal transduction and stimulation of cell growth (54–59). PI3K contains two SH2 regions and one SH3 region. PI3K is relatively new to the family of signal transducing molecules, but appears to be involved with insulin signaling through the glucose transporter, and is believed to associate directly with the ras protein. PLC-gamma is a well known signaling molecule also containing two SH2 regions and one SH3 region, and is known to hydrolyze membrane lipids to other powerful downstream signaling molecules (eg. IP3 and diacylglycerol) when stimulated by ligand activated growth factor receptors. FYN is a highly characterized member of the src-family of soluble tyrosine kinases known to be intimately associated with cell growth and differentiation. FYN contains one SH2 and one SH3 region, is also known to be stimulated by ligand activated growth factor receptors. GRB2 contains two SH3 regions and one SH2 region, and is known as an adaptor molecule in that it has no known intrinsic enzymatic capabilities. GRB2 molecules are also stimulated by ligand activated growth factor receptors. It is also worth noting that SH3-GAP (GTP-ase activating protein, LANE 3, (60, 61)), and SH3-NCF (neutrophil cytotoxic factor-type 1, LANE 8, or -type 2, lane 9, (62, 63)) had little or no affinity for the peptide containing CAS-PEP1. This evidence supports the specificity of the interaction between the CAS-PEP1 and various SH3 domains. In addition, CAS-PEP1 does not bind a control GST fusion protein as shown in lane 1 of FIG. 8.

The cytoplasmic domain of CAS-2 also comprises a p85-SH2 binding region. Though different SH2 containing proteins all require phosphorylated tyrosine residues for an interaction, it is well established that the amino acid residues surrounding the tyrosine residue dictate the specificity and strength of the interaction (64). FIG. 9 defines those amino acid sequence requirements that are necessary for interaction with the SH2 region of the p85 regulatory subunit of PI3K. The evidence clearly shows that for a binding interaction to take place with the SH2 region of p85, the tyrosine residue must be included in the amino acid sequence motif YXXM (where "X" can be any amino acid), and must have an acidic amino acid residue (D or E) approximately 3–5 residues in either direction of the YXXM motif. This exact amino acid sequence requirement exists in the cytoplasmic domain of CAS-2 (FENPIYAQMENE) (SEQ ID No. 19), and is underlined in the CAS-2 cytoplasmic sequences at the top of FIG. 9.

Altogether, the evidence demonstrates that the cytoplasmic domain of the calcium sensor protein of the invention contains three consensus SH3 binding regions and one potential SH2 recognition region of the type recognized by the SH2 region of p85 and supports an involvement of SH2 and SH3 mediated signal transduction for biological activity of the calcium sensor protein, possibly through PI3K. The potential interaction of PI3K with the calcium sensor protein is even more interesting in light of recent evidence linking the CAS-2 protein to calcium sensing in human parathyroid tissue, given that calcium sensing appears to involve G-protein activation, PKC activation, and inositol phosphate generation, all of which are activities that can be associated with PI3K signal transduction cascades. Therefore, these regions provide useful tools in assays for the identification of compounds that either stimulate or inhibit the signal transduction pathways used by the calcium sensor protein. Using assay techniques known to those skilled in the art, agonists or antagonists which mimic or inhibit the activity of the calcium sensor protein SH2/SH3 regions will be useful for the treatment of diseases that are intimately associated with the sensor, such as primary hyperparathyroidism (HPT) (52) and osteoporosis.

The relation of the calcium sensor protein to the LDL-receptor superfamily of proteins was noted above. All of the members of the LDL-receptor superfamily are 'scavenger' proteins. None of these scavenger proteins have recognized signal transduction regions, and specifically, none of these scavenger proteins contain SH regions. Therefore it was entirely unexpected to identify SH2 and SH3 binding regions active in signal transduction in the calcium sensor protein. The occurrence of these regions is a further indication that the calcium sensor protein is not a scavenger protein, even though it has regions of homology with the LDL-receptor superfamily of scavenger proteins.

Rat Heymann nephritis antigen, gp330, belongs to the LDL receptor superfamily of large, multifunctional glycoproteins (68, 69, 70). Identification of the calcium sensor protein as the human homolog of rat gp330 enables new diagnostic and therapeutic agents for human disease.

Examples of diagnostic and therapeutic uses for gp330, or biologically active fragments thereof, are disclosed in EP 358,977, the entire contents of which are incorporated herein by reference. For example, human gp330, or fragment thereof, may be used in assays for detecting autoantibodies associated with human membranous glomerulonephritis. Examples of suitable assays include immunoassays, such as ELISA. Alternatively, synthetic peptides based on the human gp330 sequence may be used to localize immunodominent B- or T-lymphocyte recognition sites. Therefore, the invention enables detection of gp330 specific autoantibodies and helper, cytotoxic or suppressor T-cells. The invention permits identification of patients who may develop idiopathic autoimmune membranous glomerulonephritis and patients susceptible to autoimmune membranous glomerulonephritis following a renal allograft.

Human gp330 is useful for treatment of human membranous glomerulonephritis according to a variety of methods. For example, gp330 may be coupled to a polyphenol followed by immunization of a patient according to U.S. Pat. No. 4,702,907, the entire contents of which are incorporated herein by reference. Treatment in this manner results in selective immunosupression of antibodies specific for gp330. As an alternative method of treatment, it is also possible to selectively remove gp330-reactive autoantibodies from sera by immobilizing gp330, or fragment thereof, on a solid support and pass the sera over the support, thereby effectively removing autoantibodies characteristic of human membranous glomerulonephritis. Alternatively, human gp330, or a fragment thereof, can be directly administered to a patient in order to perturb formation of immune complexes. Synthetic peptides based on the sequence of human gp330 are also useful therapetically. Administration of immunogenic peptides inhibits activation or function of gp330 specific helper and cytotoxic T-cells.

The structure of human gp330 includes 16 growth factor repeats separated by 8 YWTD spacer regions and 1 epidermal growth factor repeat in the immediate extracellular juxtamembrane region (FIG. 11). Therefore, administration of gp330, or a fragment thereof having growth factor activity, is useful in the treatment of wounds, such as burns and abrasions. Epidermal growth factor is also a potent inhibitor of gastric acid secretion. Therefore, gp330, or a fragment thereof having epidermal growth factor activity, is useful for treatment or prevention of gastric ulcers. Determination of effective amounts of therapeutic agent for administration is within the skill of the practitioner.

Discussion

The important role of the parathyroid as key regulator of the calcium homeostasis has been related to its exquisite capacity to sense and respond to variation in the extracellular $Ca^{2+}$ ion concentration. Essential for recognition of changes in external calcium is a cation receptor or sensor of the parathyroid cell membrane, the presence of which was implicated by a series of in vitro studies on parathyroid cell regulation (9, 10, 21–24). The concept of a cell membrane receptor was further substantiated when monoclinal antiparathyroid antibodies were found to recognize and interfere with the calcium sensing of parathyroid cells (1–6). Another crucial piece of evidence was obtained when cytotrophoblast cells of the human placenta, selected by their reactivity with the antiparathyroid antibodies, displayed parathyroid-like sensing of changes in external calcium, a function which also could be blocked by one of the anti-parathyroid antibodies (7,8). The calcium sensor of the placenta was subsequently isolated by immunosorbent and ion exchange chromatographies and shown to consist of a large glycoprotein of approximately 500 kDa molecular size (7). It was also demonstrated by immunoprecipitation that a protein of the same size reacted with the antiparathyroid antibodies within the parathyroid and kidney tubule cells (to be published, (25).

The parathyroid calcium sensor or receptor is known to have features in common with most other classical receptors for cellular activation, although it exhibits the unusual ability to bind and be activated by divalent cations. Cation binding triggers biphasic rise in $[Ca^{2+}i]$ and concomitant activation of phospholipase C, possibly via a coupled G-protein, with a resulting accumulation of inositol phosphates (2,5,9,10). An initial transient rise in $[Ca^{2+}i]$ is due to inositoltrisphosphate (Ip3)induced mobilization of $Ca^{2+}$ from intracellular sources, while an ensuing steady-state elevation in $[Ca^{2+}i]$ is caused by calcium gating through plasma membrane channels, possibly mediated by increase in inositol-tetraphosphate (Ip4) (9,10,23).

Sequence analysis of a partial cDNA clone and data-base comparison of the deduced amino acid sequence showed that the placental calcium sensor protein belongs to the LDL-receptor superfamily of proteins, and available sequences showed close similarity with the rat Heymann nephritis antigen (11,15,16). This antigen was originally described in the rat as a 330 kDa glycoprotein (gp 330), present within the proximal kidney tubule brush border, and in placental and epididymal cells, but by special staining techniques also demonstrated to occur sparsely on rat kidney glomerular cells, as well as on pneumocytes II in the lung and sporadic cells of the liver and small intestine (17–19). It has later been proposed that the molecular size of the protein was underestimated and actually should be in the range of 500 kDa (20). The Heymann antigen has been revealed as the dominating antigen causing membranous, autoimmune glomerulonephritis in the rat after immunization with a crude tubular protein fraction (17,19). Using anti-gp 330 antibodies a protein with an estimated molecular size larger than 400 kDa has been identified in man (20). The sequence identity of 77% between the human placental 500 kDa calcium sensor protein and the-rat Heymann nephritis antigen indicates that they represent related forms of the calcium sensor protein in two different species. This view is supported by close similarities in tissue distribution of the two proteins, as revealed by the immunohisto-chemistry of the present study. The antibodies E11 and G11, reacting with the calcium sensor protein, thus stain parathyroid cells, proximal kidney tubule cells, placental cytotrophoblasts and also epididymal cells. Furthermore, we have recently reported staining with one of the antiparathyroid antibodies preferentially within coated pits and the base of the proximal tubule microvilli, which equals that previously described with antibodies against the gp 330 protein (19,26). A recognized glycoprotein of similar size within the tubule brush border, renal maltase, has been located mainly to microvillar membranes and not within the coated invaginations (18).

Thus far recognized members of the LDL-receptor superfamily, the LDL-receptor, the LDL-receptor-related protein and the Heymann antigen, have been thought to function as receptors for proteins, but all exhibit functionally important $Ca^{2+}$-binding ability (16,27,28). Thus, $Ca^{2+}$ binding is necessary for the interaction of the LDL-receptor with apo-B (27). The LDL-receptor related protein ($\alpha$2-macroglobulin receptor) is also known to bind $Ca^{2+}$, which induces conformational changes, and $Ca^{2+}$ is necessary for binding of activated $\alpha_2$-macroglobulin to the receptor (16). Recently, the rat Heymann antigen was shown by a blotting technique to interact with $Ca^{2+}$ (28).

The $Ca^{2+}$ binding motifs of the calcium sensor protein remain to be identified. The sensor protein (as well as the Heymann antigen) contains EGF-like modules, like other members of the LDL-receptor superfamily (11,16,27), which may represent putative $Ca^{2+}$ binding sites. Thus, when present in the coagulation factors IX, X and protein C, each EGF-like module is known to bind one $Ca^{2+}$ ion (29–34), and the EGF-like modules have also been demonstrated to mediate $Ca^{2+}$ dependent protein/protein interaction (35). Kinetic data have suggested that the calcium sensor displays positive cooperativity in its interaction with $Ca^{2+}$, a phenomenon which appears essential for the sigmoidal regulation of $[Ca^{2+}i]$ and PTH release, with a steep relation within the physiological range of extracellular calcium (9,10). The positive cooperativity should require multiple binding sites for $Ca^{2+}$, possibly resulting from the repetitive EGF-like modules, generally present in molecules of the LDL-receptor superfamily (11,16,27). However, $Ca^{2+}$ binding to EGF-like domains are known to induce only minor, localized pertubations of the three-dimensional structure (32), and it is possible that the calcium sensor contains also other $Ca^{2+}$ binding sites.

A 43 kDa membrane protein ($\alpha$2-macroglobulin receptor-associated protein, or Heparin-binding protein) (28,36) is known to interact both with the LDL-receptor-related protein and with the rat Heymann antigen in a $Ca^{2+}$ dependent manner (28). No physiological function has yet been assigned to this protein, but it appears also in tissues where the Heymann antigen and the LDL-receptorrelated proteins are not expressed (28). An intriguing observation is the presence of a putative leucine-zipper motif in the aminoterminal part of the 43 kDa protein (36), considering that such motifs have been suggested to influence the opening and closure of membrane ion channels (37). Since the 43 kDa protein interacts with the Heymann antigen, it can be assumed to form a complex also with the calcium sensor protein in a $Ca^{2+}$-dependent manner. Interaction with the 43 kDa protein might be important for the transmission of $Ca^{2+}$ induced conformational changes within the extracellular portion of the molecule to the cell interior. It is also possible that additional proteins interact with the calcium sensor in a $Ca^{2+}$ dependent manner, and that such an interaction is important for the modulation of the sensor response. The mechanisms by which an activated calcium sensor triggers further signaling to the cell interior is unknown, although we have in preliminary experiments utilized immunoprecipitation to isolate a phosphorylated form of the sensor protein in dispersed parathyroid cells loaded with $[^{32}p]$-orthophosphate (unpublished observation).

The calcium sensor protein of the placenta may be involved in maintenance of a feto-maternal $Ca^{2+}$ gradient and placental $Ca^{2+}$ transport, possibly by mediating calcium regulation of the parathyroid hormone related peptide (PTHrP) production and/or 1,25 $(OH)_2D_3$ metabolism (8). Its presence already within the blastocyst (unpublished observation) may indicate a function also as adhesion molecule, or implicate involvement in differentiation or growth regulation, as suggested for the Heymann antigen (38). The function of a calcium sensor within the kidney tubule brush border is less well explored. However, it should be noted that the enzyme 1-$\alpha$-hydroxylase present in the placenta and proximal kidney tubule, is regulated by extracellular calcium, and the calcium sensor might accordingly regulate 1,25 $(OH)_2D_3$ metabolism, but it may possibly also influence $Ca^{2+}$ reabsorption from the glomerular filtrate (7–9). The significance of the presence of the calcium sensor protein on epididymal cells, as well as rat pneumocytes, liver and intestinal cells as implicated by the distribution of the Heymann antigen (18,19), yet remains unknown. It has, however, been proposed that several cell types may exhibit $Ca^{2+}$ sensing ability for regulation of various functions, separate from the general calcium homeostasis, either during development or in the differentiated state (10).

The association with autoimmune nephritis substantiates that the Heymann antigen is an immunogen molecule. This may have implication also in parathyroid disorder, as we have recently reported the presence of circulating parathyroid autoantibodies and induction of class II transplantation antigen in the pathological parathyroid tissue of patients with primary HPT. These findings suggested that autoimmune phenomena may be involved in HPT (39) and autoimmunity has also been implicated in the pathogenesis of rare idiopathic hypoparathyroidism (10). The availability of cDNA clones for the calcium sensor should, enable extended studies on the pathophysiology in parathyroid disorder, and also in vestigation of a possible genetic abberration affecting the calcium sensing function of the parathyroid and kidney tubule in kindreds with familial hypocalciuric hypercalcemia (FHH) (40,41).

The skilled person within this art realizes that the information obtainable from the nucleotide sequences of FIG. 3, FIG. 6 and FIG. 10 can be used for isolating the genomic sequence encoding the calcium sensor. Preferably, an analysis of overlapping cDNA clones in conjunction with PCR techniques is used. The genomic sequence can be obtained from the analysis of overlapping genomic cosmid and/or lambda phage clones.

References

1. Juhlin, C., Holmdahl, R., Johansson, H., Rastad, J., Akerström, G., Klareskog, L., (1987) Proc. Natl. Acad. Sci. USA. 84, 2990–2994.
2. Juhlin, C., Johansson, H., Holmdahl, R., Gylfe, E., Larsson, R., Rastad, J., Akerström, G., Klareskog, L., (1987) Biochem. Biophys. Res. Connun. 143, 570–574.
3. Juhlin, C., Klareskog, L., Nygren, P., Gylfe, E., Ljunghall, S., Rastad, J., Akerström, G., (1988) Endocrinol. 122, 2999–3001.
4. Juhlin, C., Akerström, G., Klareskog, L., Gylfe, E., Holmdahl, R., Johansson, H., Ljunghall, S., Larsson, R., Nygren, P., Rastad, J., (1988) World. J. Surg. 12, 552–558.
5. Gylfe, E., Juhlin, C., Akerström, G., Klareskog, L., Rask, L., Rastad, J., (1990) Cell Calcium. 11, 329–332.
6. Juhlin, C., Rastad, J., Klareskog, L., Grimelius, L., Akerström, G., (1989) Am. J. Pathol. 135, 321–328.
7. Juhlin, C., Lundgren, S., Johansson, H., Lorenzon, J., Rask, L., Larsson, E., Rastad, J., Akerström, G., Klareskog, L., (1990) J. Biol. Chem. 265, 8275–8279.
8. Hellman, P., Ridefelt, P., Juhlin, C., Akerström, G., Rastad, J., Gylfe, E., (1992) Arch. Biochem. Ciophys. 293, 174–180.
9. Akerström, G., Rastad, J., Ljunghall, S., Ridefelt, P., Juhlin, C., Gylfe, E., (1991) World. J. Surg. 15, 672–680.
10. Brown, E. M., (1991) Phys. Rev. 71, 371–411.
11. Raychowdury, R., Niles, J. L., Mc Cluskey, R. T., Smith, J. A., (1989) Science, 244, 1163–1165.
12. Denhardt, D. T., (1966) Biochem. Biophys. Res. Commun. 23, 641–646.
13. Pearson, W. R., Lipman, D. J., (1988) Proc. Natl. Acad. Sci. USA. 85, 2444–2448.
14. Holmdahl, R., Rubin, K., Klareskog, L., Larsson, E., Wigzell, H., (1986) Arthritis. Rheum. 29, 400–410.
15. Yamamoto, T., Davis, C. G., Brown, M. S., Schneider, W. J., Casey, M. L.,Goldstein, J. L., Russel, D. W., (1984) Cell. 39, 27–38.
16. Herz, J., Haman, U., Rogne, S., Myklebost, O., Gausepohl, H., Stanley, K. K.,(1988) EMBO. J. 7, 4119–4127.
17. Chatelet, F., Brianti, E., Ronco, P., Roland, J., Verroust, P., (1986) Am. J. Pathol. 122, 500–511.
18. Chatelet, F., Brianti, E., Ronco, P., Roland, J., Verroust, P., (1986) Am. J. Pathol. 122, 512–519.
19. Kerjaschki, D., Farquhar, M. G., (1984) in Nephrology ed Robinsson R. R., New York Springer-Verlag pp 560–574.
20. Kerjaschki, D., Horvat, R., Binder, S., Susani, M., Dekan, G., Ojha, P. P., Hillermans, P., Ulrich, W., Doninn, U., (1987) Am. J. Pathol. 129, 183–191.
21. Wallfelt, C., Larsson, R., Johansson, H., Rastad, J., Akerström, G., Ljunghall, S., Gylfe, E., (1985) Acta. Physiol. Scand. 124, 239–245.
22. Gylfe, E., Larsson, R., Johansson, H., Nygren, P., Rastad, J., Wallfelt, C., Akerström, G.,(1986) Febs. lett. 205, 132–136.
23. Nemeth, E., Scarpa, A., (1987) J. Biol. Chem. 262, 5188–5196.
24. Gylfe, E., Akerström, G., Juhlin, C., Klareskog, L., Rastad, J., (1990) In: Hormones and Cell Regulation. Eds: Dumont, J. E., Nunez, J., King, R. J. B., John Libhey Eurotext Ltd., London pp 5–15.
25. Lundgren, S., Juhlin, C., Rastad, J., Klareskog, L., Akerström, G., Rask, L., Submitted.
26. Bjerneroth, G., Juhlin, C., Akerström, G., Rastad, J., (1992) J. Submicrosc.Cytol. Pathol. 24, 179–186.
27. Brown, M. S., Goldstein, J. L., (1986) Science. 232, 34–47.
28. Christensen, E. J., Glieman, J., Moestrup, S. K., (1992) J. Histochem. Cytochem.40, 1481–1490.
29. Handford, P. A., Baron, M., Mayhew, M., Willis, A., Beasly, T., Brownlee, G. G., Campbell, I. D., (1990) EMBO J. 9, 475–480.
30. Huang, L. H., Ke, X-H., Sweeny, W., Tam, I. P., (1989) Biochem. Biophys. Res. Commun. 160, 133–139.
31. Persson, E., Selander, M., Linse, S., Drakenberg, T., Ohlin, A. K., Stenflo,J., (1989) J. Biol. Chem. 264, 16897–16904.
32. Ohlin, A. K., Linse, S., Stenflo, J., (1988) J. Biol. Chem. 263, 7411–7417. Urukawa, T.,
33. Ohlin, A. K., Landes, G., Bourdan, P., Oppenheimer, C., Wydro, L., Stenflo, J., (1988) J. Biol. Chem. 263, 19240–19248.
34. Selander—Sunnerhagen, M., Ullner, M., Persson, C., Teleman, O., Stenflo, J., Drakenberg, T., (1992) J. Biol. Chem. 267, 19642–19649.
35. Rebay, I., Fleming, R. J., Felion, R. G., Cherbas, L., Cherbas, P., Artavanis -Tsakonas, S., (1991) Cell. 67, 687–699.
36. Furukawa, T., Ozawa, M., Hvang, R. P., Muramatsu, T., (1990) J. Biochem. 108, 297–302.
37. McCormack, K., Campanelli, I. T., Ramaswami, M., Mathew M. K., Tanoye, M. A., Iverson, L. E., Rudy, B., (1989) Nature. 340, 103.
38. Mendrick, D. L., Chung, D. C., Remcke, H. G., (1990) Exp. Cell. Research. 188, 23–25.
39. Bjerneroth, G., (1992) Comprehensive summaries of Uppsala Disertations from the Faculty of Medicine 360, ISBN. 91-54-2928–9.
40. Marx, S. J., Attie, M. F., Levine, M. A., Spiegel, A. M., Downs, R. W., Lasker, R. D., (1981) Medicine 60, 397–412.
41. Choo, Y-H. W., Brown, E. H., Levi, T., Crowe, G. B., Atkinson, A. B., Arnqvist, H. J., Toss, G., Fuleihan, G. E-H., Seidman, J. G., Seidman, C. E., (1992) Nature Genetics. 1, 298–300.
42. Cantley, L. C., Auger, K. R>, Carpenter, C., Duckworth, B., Graziani, A., Kapeller, R., Ioltoff, S., (1991) *Cell* 64, 281–302
43. Koch, C. A., Anderson, D., Moran, M. F., Elllis, C., Pawson, T. (1991) *Science* 252, 668–74
44. Mayer, B. J., Hamagucchi, M., Hanafusa, H. (1088) *Nature* 332, 272–275
45. Musacchio, A., Gibson, T., Lehto, V. P., Saraste, M. (1992) *Febs Lett* 307, 55–61
46. Clark, S. G., Stern, M. J., Horvitz, H. R. (1992) *Nature* 356, 340–4
47. Lowenstein, E. J., Daly, R. J., Batzer, A. G., Li, W., Margolis, B., Lammers, R., Ullrich, A., Skolnik, E. Y., Bar-Sagi, D., Schlessinger, J. (1992) *Cell* 70, 431–42
48. Chardin, P., Camonis, J. H., Gale, N. W., van Aelst, L., Schlessinger, J., Wigler, M. H., Bar-Sagi, D. (1993) *Science* 260, 1338–43
49. Olivier, J. P., Raabe, T., Henkemeyer, M., Dickson, B., Mbamalu, G., Margolis, B., Schlessinger, J., Hafen,. E., Pawson, T. (1993) *Cell* 73, 179–91
50. Rozakis-Adcock, M., Fernley, R., Wade, J., Pawson, T., Bowtell, D. (1993) *Nature* 363, 83–5
51. Sambrook, J., Fritsch, E. F., Maniatis, T. (1989) *Molecular Cloning: A Laboratory Manual* (Cold Spring Harbor Lab. Press, Plainview, N.Y.).

52. Lundgren, S., Hjalm, G., Hellman, P., Juhlin, C., Rastad, J., Klareskog, L., Akerstrom, G., Rask, L. (1994) *Experimental Cell Research* 212, 001–07
53. Yu, H., Chen, J. K., Feng, S., Dalgarno, D. C., Brauer, A. W., Schreiber, S. L. (1994) *Cell* 76, 933–945
54. Stephens, L. R., Jackson, T. r., Hawkins, P. T. (1993) *Biochimica et Biophysica Acta* 1179, 27–75
55. Dhand, R., Hiles, I., Panayotou, G., Roche, S., Fry, M. J., Gout, I., Totty, N F., Truong, O., Vicendo, P., Yonezawa, K., Kasuga, M., Courtneidge, S. A., Waterfield, M. D. (1994) *The EMBO Journal* 13, (3), 522–533
56. Marshall, I. C. B., Taylor, C. W. (1993) *J. Exp. Biol.* 184, 161–182
57. Prasad, K. V., Janssen, O., Kapeller, R., Raab, M., Cantley, L. C., Rudd, C. E. (1993) *Proc. Natl. Acad. Sci. U.S.A.* 90, 7366–7370
58. Wasenius, V. M., Merilainen, J., Lehto, V. P. (1993) *Gene* 134, 299–300
59. Trahey, M., Wong, G., Halenbeck, R., Rubinfeld, B., Martin, G. A., Ladner, M., Long, C. M., Crosier, W. J., Watt, K., Koths, K., McCormick F. (1988) *Science* 242, 1697–1700
60. Hsieh, C. L., Vogel, U. S., Dixon, R. A., Francke, U. (1989) *Somat. Cell Mol. Genet.* 15, 579–90
61. Kenney, R. T., Leto, T. L. (1990) *Nucleic Acids Res* 18, 7193
62. Francke, U., Hsieh, C. L., Foellmer, B. E., Lomax, K. J., Malech, H. L. Leto, T. L. (1990) *Am J Hum Genet* 47, 483,492
63. Songyang, Z., Shoelson, S. E., Chaudhuri, M., Gish, G., Pawson, T., Haser, W. G., King, F., Roberts, T., Ratnofsky, S., Lechleider, R. J., Neel, B. G.,. Birge, R. B., Fajardo, J. E., Chou, M. M., Hanafusa, H. Schaffhausen, B., Cantley, L. C. (1993) *Cell* 72, 767–778
64. Brown, E. M. (1991) *Physiological Reviews* 71(2), 371–411
65. Brown, E. M. (1993) *Current Opinion in Nephrology and hypertension* 2 541–551
66. Juhlin, C., Akerstrom, G., Klareskog, L., Gylfe, E., Johansson, H., Larsson, R., Ljunghall, S., Nygren, P., Rastad, J. (1988) *World J. Surg.* 12, 552–558
67. Saito, A., Pietromonaco, S., Loo, A., Farquhar, M. (1994) *Proc. Natl. Acad. Sci. USA* 91, 9725–9729.
68. Farquhar, M. et al. (1994) *Ann. N.Y. Acad. Sci.* 737, 96–113.
69. Kounnas, M. et al. (1994) *Ann. N.Y. Acad. Sci.* 737, 114–123.
70. Moestrup, S. et al. (1994) *Ann. N.Y. Acad. Sci.* 737, 124–137.

What is claimed is:

1. An antisense nucleic acid that hybridizes with all of the sequence of either SEQ ID NO:3, SEQ ID NO:11, SEQ ID NO:83, or with an mRNA encoding SEQ ID NO:84, said antisense nucleic acid suitable for use as a probe to specifically detect SEQ ID NO:3, SEQ ID NO:11, SEQ ID NO:83, or an mRNA encoding SEQ ID NO:84.

2. The antisense nucleic acid according to claim 1 wherein said antisense nucleic acid is an RNA.

3. An antisense sequence that hybridizes with all of a nucleic acid encoding a protein comprising an amino acid sequence selected from the group consisting of SEQ ID NO:4, SEQ ID NO:12, and SEQ ID NO:84, wherein said antisense sequence is suitable for use as a probe to specifically detect a nucleic acid encoding a protein comprising an amino acid sequence selected from the group consisting of SEQ ID NO:4, SEQ ID NO:12, and SEQ ID NO:84.

4. An antisense RNA that hybridizes with all of a nucleic acid encoding a protein comprising an amino acid sequence selected from the group consisting of SEQ ID NO:4, SEQ ID NO:12, and SEQ ID NO:84, wherein said antisense sequence is suitable for use as a probe to specifically detect a nucleic acid encoding a protein comprising an amino acid sequence selected from the group consisting of SEQ ID NO:4, SEQ ID NO:12, and SEQ ID NO:84.

* * * * *